(12) United States Patent
Skolnick et al.

(10) Patent No.: US 6,631,332 B2
(45) Date of Patent: Oct. 7, 2003

(54) METHODS FOR USING FUNCTIONAL SITE DESCRIPTORS AND PREDICTING PROTEIN FUNCTION

(75) Inventors: Jeffrey Skolnick, San Diego, CA (US); Jacquelyn S. Fetrow, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/839,821

(22) Filed: Apr. 20, 2001

(65) Prior Publication Data

US 2001/0034580 A1 Oct. 25, 2001

Related U.S. Application Data

(62) Division of application No. 09/322,067, filed on May 27, 1999.
(60) Provisional application No. 60/099,300, filed on Aug. 25, 1998, and provisional application No. 60/120,311, filed on Feb. 16, 1999.

(51) Int. Cl.[7] .................. G01N 33/48; G01N 31/00; G01N 33/00; C12Q 1/00
(52) U.S. Cl. .................. 702/19; 702/27; 435/4; 436/86
(58) Field of Search .................. 435/4; 436/86; 702/19, 27

(56) References Cited

PUBLICATIONS

Skolnick, J. et al., "Monsster: A method of Folding Globular Proteins with a Small Number of Distance Restraints", J. Mol. Biol., vol. 265, pp. 217–241 (Jan. 17, 1997).*
Wallace et al., "Derivation of 3D coordinate templates for searching structural databases: Application to Ser–His–Asp catalytic triads in the serine proteinases and lipases", Protein Science. 1996, vol. 5, pp. 1001–1013, see abstract.
Escalier et al., "Pairwise and multiple identification of three–dimensional common substructures in proteins", Journal of Computational Biology, 1998, vol. 5, No. 1, pp. 41–56.
Clarke et al., "Evidence from cassette mutagenesis for a structure function motif in a protein of unknown structure", Science, Apr. 22, 1988, vol. 240, pp. 521–523.

Viswanadhan et al., "New joint prediction algorithm ($Q_7$–Jasep) improves the prediction of protein secondary structure", Biochemistry, 1991, vol. 30, pp. 11164–11172.
Kalhammer et al., "Ras–binding domain: predicting function versus folding" FEBS Letters. 1997, vol. 414, pp. 599–602.
Chao et al., "Aligning two sequences within a specified diagonal band", CABIOS, 1992, vol. 8, No. 5, pp. 481–487.
Rychlewski et al., "Functional insight from structural predictions: Analysis of the *Escherichia coli* genome" Mar. 1999, vol. 8, pp. 614–624.
Pawlowski et al., "The *Helicobacter pylori* genome: From sequence analysis to structural and functional predictions", Proteins: Structure, Function and Genetics. Jul. 1999, vol. 36, pp. 20–30.
Zhang et al., "From fold predictions to function predictions: Automation of functional site conservation analysis for functional genome predictions", Protein Science. May 1999, vol. 8, pp. 1104–1115.
Holm, et al., "An Evolutionary treasure: Unification of a Broad Set of Aminohydrolases Related to Urease", Proteins: Structure, Function and Genetics 28:72–82 (1997).

* cited by examiner

Primary Examiner—Kenneth R. Horlick
Assistant Examiner—Teresa Strzelecka
(74) Attorney, Agent, or Firm—Fish & Richardson P.C.

(57) ABSTRACT

The present invention concerns methods and systems for predicting the biological function(s) of proteins. The invention is based on the development of functional site descriptors for discrete protein biological functions. Functional site descriptors are geometric representations of protein functional sites in three-dimensional space, and can also include additional parameters, for example, conformational information. Following their development, one or more functional site descriptors (for one or more different biological functions) are used to probe protein structures to determine if such structures contain the functional sites described by the corresponding functional site descriptors. If so, the protein(s) containing the functional site(s) are predicted to have the corresponding biological function(s). In preferred embodiments, a library of functional site descriptors is used to probe inexact protein structures derived by computational methods from amino acid sequence information to predict the biological function(s) of such sequences and of the gene(s) encoding the same.

47 Claims, 13 Drawing Sheets

|  | AVE DIST 322 | STD DEV 324 | MULT 326 |
|---|---|---|---|
| A→B | 3.83 | 0.03 | 2.0 |
| B→C | 10.09 | 0.14 | 2.0 |
| A→C | 7.2 | 0.09 | 2.0 |
| A-1→B | 5.46 | 0.04 | 2.0 |
| A+1→B | 0.00 | 0.00 | 2.0 |
| C-1→A | 6.05 | 0.10 | 2.0 |
| C+1→A | 9.63 | 0.06 | 2.0 |
| B-1→A | 0.00 | 0.00 | 2.0 |
| B+1→A | 5.38 | 0.09 | 2.0 |

*Fig. 8*

```
             1                                                                    50
RNT1_ASPOR   ..........  ...MMYSKLL  TLTTLLLPTA  LALPSLVERA  CDYTCGSNCY
RNF1_FUSMO   ..........  ..........  ..........  .........Q  SATTCGSTNY
RNMS_ASPSA   ..........  ..........  ..........  ........ES  CEYTCGSTCY
RNU2_USTSP   ..........  ..........  ..........  .......CNIP ESTNCGGNVY
RNC2_ASPCL   ..........  ..........  ..........  .........D  CDYTCGSHCY
RNP3_PENBR   ..........  ..........  ..........  .........A  CAATCGTVCY
RNPC_PENCH   ..........  ..........  ..........  .........A  CAATCGSVCY
RNN1_NEUCR   ..........  ..........  ..........  .........A  CMYICGSVCY
RNU1_USTSP   ..........  ..........  ..........  .......QGG  VSVNCGGTYY
RNAS_ASPGI   MVAIKNLVLV  ALTAVTALAV  PSPLEARAVT  WTCLNDQKNP  KTNKYETKRL
RNCL_ASPCL   MVAIKNLVLV  ALTAVTALAM  PSPLEERAAT  WTCMNEQKNP  KTNKYENKRL
RNMG_ASPRE   MVAIKNLFLL  AATAVSVLAA  PSPLDARA.T  WTCINQQLNP  KTNKWEDKRL 51                                                                   100
RNT1_ASPOR   SSSDVSTAQA  AGYQLHEDGE  TVGSNSYPHK  YNN.YEG...  .......FDF
RNF1_FUSMO   SASQVRAAAN  AACQYYQNDD  SAGSTTYPHT  YNN.YEG...  .......FDF
RNMS_ASPSA   WSSDVSAAKA  KGYSLYESGD  TI..DDYPHG  YHD.YEG...  .......FDF
RNU2_USTSP   SNDDINTAIQ  GA...LDDVA  RPDGDNYPHQ  YYD.EAS...  .......EDI
RNC2_ASPCL   SASAVSDAQS  AGYQLESAGQ  SVGRSRYPHQ  YRN.YEG...  .......FNF
RNP3_PENBR   TSSAISSAQA  AGYNLYSTND  DV..SNYPHE  YHN.YEG...  .......FDF
RNPC_PENCH   TSSAISAAQE  AGYDLYSAND  DV..SNYPHE  YRN.YEG...  .......FDF
RNN1_NEUCR   SSSAISAALN  KGYSYYEDGA  TAGSSSYPHR  YNN.YEG...  .......FDF
RNU1_USTSP   SSTQVNRAIN  NA.....KSG  QYSSTGYPHT  YNN.YEG...  .......FDF
RNAS_ASPGI   LYNQNKAESN  SHHAPLSDGK  T..GSSYPHW  FTNGYDGDGK  LPKGRTPIKF
RNCL_ASPCL   LYNQNNAESN  AHHAPLSDGK  T..GSSYPHW  FTNGYDGDGK  ILKGRTPIKW
RNMG_ASPRE   LYSQAKAESN  SHHAPLSDGK  T..GSSYPHW  FTNGYDGNGK  LIKGRTPIKF 101                                                                  150
RNT1_ASPOR   ..S.VSSP..  ..........  ..YYEWPILS  SGDVYS..G.  ...GSPGADR
RNF1_FUSMO   ..P.VDGP..  ..........  ..YQEFPIKS  GG.VYT..G.  ...GSPGADR
RNMS_ASPSA   ..P.VSGT..  ..........  ..YYEYPIMS  DYDVYT..G.  ...GSPGADR
RNU2_USTSP   TLCCGPGS..  ..........  ..WSEFPLVY  NGPYYS..SR  DNYVSPGPDR
RNC2_ASPCL   ..P.VSGN..  ..........  ..YYEWPILS  SGSTYN..G.  ...GGPGADR
RNP3_PENBR   ..P.VSGT..  ..........  ..YYEFPILK  SGKVYT..G.  ...SSPGADR
RNPC_PENCH   ..P.VSGT..  ..........  ..YYEFPILR  SGAVYS..G.  ...NSPGADR
RNN1_NEUCR   ..P.TAKP..  ..........  ..WTEFPILS  SGRVYT..G.  ...GSPGADR
RNU1_USTSP   S.DYCDGP..  ..........  ..YKEYPLKT  SSSGYT..G.  ...GSPGADR
RNAS_ASPGI   GKSDCDRPPK  HSKDGNGKTD  HYLLEFPTFP  DGHDYKFDSK  KPKENPGPAR
RNCL_ASPCL   GNSDCDRPPK  HSKNGDGKND  HYLLEFPTFP  DGHQYNFDSK  KPKEDPGPAR
RNMG_ASPRE   GKADCDRPPK  HSQNGMGKDD  HYLLEFPTFP  DGHDYKFDSK  KPKEDPGPAR 151                               182
RNT1_ASPOR   VVFNENNQ.L  AGVITHTGAS  G.NNFVECT.  ..
RNF1_FUSMO   VVINTNCE.Y  AGAITHTGAS  G.NNFVGCSG  TN
RNMS_ASPSA   VIFNGDDE.L  AGVITHTGAS  G.DDFVACSS  S.
RNU2_USTSP   VIYQTNTGEF  CATVTHTGAA  SYDGFTQCS.  ..
RNC2_ASPCL   VVFNDNDE.L  AGLITHTGAS  G.DGFVACY.  ..
RNP3_PENBR   VIFNDDDE.L  AGVITHTGAS  G.NNFVACT.  ..
RNPC_PENCH   VIFNGNDQ.L  AGVITHTGAS  G.NNFVACD.  ..
RNN1_NEUCR   VIFDSHGN.L  DMLITHNGAS  G.NNFVACM.  ..
RNU1_USTSP   VVYDSNDGTF  CGAITHTGAS  G.NNFVQCSY  ..
RNAS_ASPGI   VIYTYPNKVF  CGIIAHTKEN  Q.GELKLCSH  ..
RNCL_ASPCL   VIYTYPNKVF  CGIVAHTREN  Q.GDLKLCSH  ..
RNMG_ASPRE   VIYTYPNKVF  CGIVAHQRGN  Q.GDLRLCSH  ..
```

Fig. 12/1

|         |         | 1rtu  | 1fus  | 1rms  | AVG    | SD     | Actual | Var | 9mt   |
|---------|---------|-------|-------|-------|--------|--------|--------|-----|-------|
| 30s His | 90sHis  | 15.20 | 16.70 | 15.97 | 15.950 | 0.6577 | 15.9   | 1.5 | 15.63 |
| 30s His | Glu     | 5.36  | 5.84  | 5.71  | 5.637  | 0.2221 | 5.7    | 0.5 | 5.79  |
| 90s His | Glu     | 13.03 | 12.90 | 12.44 | 12.580 | 0.2773 | 12.6   | 1.0 | 11.95 |
| Tyr     | Phe     | 16.69 | 16.40 | 16.62 | 16.580 | 0.1290 | 16.5   | 0.5 | 16.43 |
| Tyr     | Arg     | 10.50 | 10.20 | 10.25 | 10.330 | 0.1473 | 10.3   | 0.5 | 10.29 |
| Phe     | Arg     | 9.61  | 9.34  | 9.40  | 9.450  | 0.1418 | 9.5    | 0.5 | 9.59  |
|         |         |       |       |       |        |        |        |     |       |
| 30s His | Tyr     | 4.87  | 5.02  | 5.13  | 5.007  | 0.1305 | 5.0    | 0.5 | 5.07  |
| 30s His | Phe     | 14.47 | 15.60 | 15.28 | 15.120 | 0.5866 | 15.2   | 1.0 | 15.28 |
| 30s His | Arg     | 10.44 | 11.30 | 10.94 | 10.900 | 0.4366 | 11.0   | 1.0 | 11.16 |
| 90s His | Tyr     | 16.06 | 16.10 | 15.86 | 16.010 | 0.1286 | 15.8   | 1.0 | 15.32 |
| 90s His | Phe     | 4.67  | 4.60  | 4.63  | 4.633  | 0.0351 | 4.6    | 0.5 | 4.64  |
| 90s His | Arg     | 8.72  | 8.79  | 8.50  | 8.670  | 0.1513 | 8.6    | 0.5 | 8.48  |
| Glu     | Tyr     | 7.36  | 7.10  | 7.13  | 7.197  | 0.1422 | 7.2    | 0.5 | 7.24  |
| Glu     | Phe     | 12.17 | 11.80 | 11.77 | 11.900 | 0.2309 | 11.9   | 0.5 | 11.96 |
| Glu     | Arg     | 6.33  | 6.16  | 5.87  | 6.120  | 0.2326 | 6.1    | 0.5 | 6.00  |

Fig. 12/2

METHODS FOR USING FUNCTIONAL SITE DESCRIPTORS AND PREDICTING PROTEIN FUNCTION

RELATED APPLICATIONS

This application is a divisional of U.S. patent applications Ser. No. 09/322,067, now pending, filed on May 27, 1999, which claims the benefit of priority under 35 U.S.C. §119(e) of U.S. Provisional Applications Nos. 60/099,300, filed Aug. 25, 1998, and 60/120,311, filed Feb. 16, 1999. The aforementioned applications are explicitly incorporated herein by reference in their entirety and for all purposes.

GOVERNMENT RIGHTS

The United States government may have certain in rights in the subject matter described and claimed herein by virtue of funding provided pursuant to NIH grant number GM48835.

BACKGROUND OF THE INVENTION

1. Field of the Invention

The present invention concerns methods and systems for predicting the function of proteins. In particular, the invention relates to materials, software, automated systems, and methods for implementing the same in order to predict the function(s) of a protein. Protein function prediction includes the use of functional site descriptors for a particular protein function.

2. Background of the Invention

The following description includes information that may be useful in understanding the present invention. It is not an admission that any of the information provided herein is prior art to the presently claimed invention, nor that any of the publications specifically or implicitly referenced are prior art to that invention.

A central tenet of modern biology is that heritable genetic information resides in a nucleic acid genome, and that the information embodied in such nucleic acids directs cell function. This occurs through the expression of various genes in the genome of an organism and regulation of the expression of such genes. The pattern of which subset of genes in an organism is expressed at a particular time in a particular cell defines the phenotype, and ultimately cell and tissue types. While the least genetically complex organisms, i.e., viruses, contain on the order of 10–50 genes and require components supplied by a cell of another organism in order to reproduce, the genomes of independent, living organisms (i.e., those having a genome that encodes for all the information required for the organism to survive and reproduce) that are the least genetically complex have more than 400 genes (for example, *Mycoplasma genitalium*). More complex, multicellular organisms (e.g., mice or humans) contain genomes believed to be comprised of tens of thousands or more genes, each of which codes for one or more different expression products.

Most organismal genomes are comprised of double-stranded DNA. Each strand of the genomic DNA is comprised of a long polymer of the four deoxyribonucleotide bases A (adenine), T (thymine), G (guanine), and C (cytosine). Double-stranded DNA is formed by the anti-parallel, non-covalent association between two DNA strands. This association is mediated by hydrogen bonding between nucleotide bases, with specific, complementary pairing of A with T and G with C. Each gene in the genomic DNA is expressed by transcription, wherein a single-stranded RNA copy of the gene is transcribed from the double-stranded DNA. The transcribed strand of RNA is complementary to the coding strand of the DNA. RNA is composed of ribonucleotide (rather than deoxyribonucleotide) bases, three of which are similar to those found in DNA: A, G, and C. The fourth RNA ribonucleotide base, uracil (U), substitutes for T found in DNA and is complementary to the A base. Following transcription, the RNAs transcribed from many genes are translated into polypeptides. The particular sequence of the nucleotide bases normally determines what protein, and hence what function(s), a particular gene encodes.

Some genes are transcribed, but not translated; thus, the final gene products of these genes are RNA molecules (for example, ribosomal RNAs, small nuclear PNAs, transfer RNAs, and ribozymes (i.e., RNA molecules having endoribonuclease catalytic activity). However, most RNAs serve as messengers (mRNAs), and these are translated into polypeptides. The particular sequence of the ribonucleotides incorporated into an RNA as it is synthesized is dictated by the gene found in the genomic DNA from which it was transcribed. In the translation of an mRNA, the particular nucleotide sequence determines the particular amino acid sequence of the polypeptide translated therefrom. Briefly, in a coding region of an mRNA (and in its corresponding gene), each nucleotide triplet, or "codon" (of which there are $4^3$, or 64, possibilities) codes for one amino acid, except that three codons code for no amino acids (each being a "stop" translation codon). Thus, the sequence of codons (dictated by the nucleotide sequence of the corresponding gene) specifies the amino acid sequence of a particular protein, and it is the amino acid sequence that ultimately determines the three-dimensional structure of the protein. Significantly, three-dimensional structure dictates the particular biological function(s) of any biomolecule, including proteins.

The elegant simplicity of the foregoing schema is obscured by the complexity and size of the genomes found in living systems. For example, the haploid human genome comprises about $3 \times 10^9$ (three billion) nucleotides spread across 23 chromosomes. However, it is currently estimated that less than 5% of this encodes the approximately 80,000–100,000 different protein-coding genes believed to be encoded by the human genome. Because of its tremendous size, to date only a portion of the human genome has been sequenced and deposited in genome sequence databases, and the positions of many genes and their exact nucleotide sequences remain unknown. Moreover, the biological function(s) of the gene products encoded by many of the genes sequenced so far remain unknown. Similar situations exist with respect to the genomes of many other organisms.

Notwithstanding such complexities, numerous genome sequence efforts designed to determine the exact sequence of the nucleotides found in genomic DNA of various organisms are underway and significant progress has been made. For example, the Human Genome Project began with the specific goal of obtaining the complete sequence of the human genome and determining the biochemical function(s) of each gene. To date, the project has resulted in sequencing a substantial portion of the human genome, and is on track for its scheduled completion in the near future. At least twenty-one other genomes have already been sequenced, including, for example, *M. genitalium, M. jannaschii, H. influenzae, E. coli,* and yeast (*S. cerevisiae*). Significant progress has also been made in sequencing the genomes of model organisms, such as mouse, *C. elegans,* and *D. melanogaster.* Several databases containing genomic information annotated with some functional information are maintained by different organizations, and are accessible via the internet.

Such sequencing projects result in vast amounts of nucleotide sequence information, which is typically deposited in genome sequence databases. However, these raw data (much of it being known only at the cDNA level), being devoid of corresponding information about genes and protein structure or function, are in and of themselves of extremely limited use (Koonin, et al. (1998), Curr. Opin. Struct. Biol., vol. 8:355–363). Thus, the practical exploitation of the vast numbers of sequences in such genome sequence databases is crucially dependent on the ability to identify genes and, for example, the function(s) of gene-encoded proteins.

To maximize the utility of such nucleotide sequence information, it must be interpreted. For example, it is important to understand where each sequence is located in the genome, and what biological function(s), if any, the sequence encodes, i.e., what is the purpose of the sequence or, if transcribed (or transcribed and translated), the resulting product, in a biological system? For example, is the sequence a regulatory region or, if it is transcribed (or transcribed and translated), does the gene product bind to another molecule, regulate a cellular process, or catalyze a chemical reaction?

To answer these questions, significant effort has been directed towards understanding or describing the biological function(s) coded for in each nucleotide sequence. Predicting the function(s) of biomolecules encoded by genes, particularly proteins, is most often done by sequence comparison to known structures. The basis of this approach is the commonly accepted notion that similar sequences must have a common ancestor, and would therefore have similar structures and related functions. Accordingly, algorithms have been developed to analyze what a particular nucleotide sequence encodes, e.g., a regulatory region, an open reading frame (ORF), particularly for protein sequences, or a non-translated RNA. See, e.g., "Frames" (Genetics Computer Group, Madison, Wis.), which is used for identifying ORFs. For sequences predicted or determined to be ORFs, it is possible to determine the amino acid sequence of the protein encoded thereby using simple analytical tools well known in the art. For example, see "Translate" (Genetics Computer Group, Madison, Wis.). However, to date determination of the primary structure of a protein in and of itself provides little, if any, functional information about the protein or its corresponding gene.

A number of methods have been developed in an attempt to glean functional information about a deduced amino acid sequence. The most common computational methods include sequence alignment and analysis of local sequence motifs, although these methods are limited by the extent of sequence similarity between sequences of unknown and known function. Additionally, these methods increasingly fail as sequence identity decreases. Other recently developed computational methods include whole genome comparison (Himmelreich et al., 1997), and analysis of gene clustering (Himmelreich et al., 1997; Tamames et al., 1997). Others have developed experimental methods to analyze protein function on a gemone-wide basis. These methods include, for example, "two hybrid screens" (Fromont-Racine et al., 1997) and genome-wide scanning of gene expression patterns (Ito & Sakaki, 1996).

Sequence alignment is the method most commonly used in attempts to identify protein function from amino acid sequence. In this method, the extent of amino acid sequence identity between an experimental sequence and one or more sequences whose function(s) is(are) known is computed. Alignment methods such as BLAST (Altschul et al., 1990), BLITZ (MPsrch) (Sturrock & Collins, 1993), and FASTA (Pearson & Lipman, 1988) are typically employed for this purpose. Assignment of function is based on the theory that significant sequence identity strongly predicts functional similarity (Fitch, 1970?).

However, because of the frequent lack of substantial sequence similarity among proteins, these methods often fail (Delseny et al., 1997; Dujon, 1996). Additionally, newly discovered amino acid or nucleotide sequences frequently do not match any known or available sequence. Indeed, many protein amino acid sequences (from 30–60% or more) that have been deduced from genome project-derived nucleotide sequence information represent novel protein families with unknown function, and for which no homologous sequence can be identified (Delseny et al., 1997; Dujon, 1996). Furthermore, such conventional sequence alignment methods cannot consistently detect functional and structural similarities, particularly when sequence identity is less than about 25–30%. Hobohm & Sander, 1995. In practice, roughly half of a given genome falls into one of these two categories or no homology, or less than about 25–30% homology, with a known sequence. Bork and Koonin (1998), Nature Genet., vol. 18: 313–318; E. V. Koonin (1997), Curr. Biol., vol. 7:R656–R659. It is also important to understand that matches with 50% or more identity over a 40-amino acid or smaller stretch of sequences often occur by chance, and if other information is lacking, relationships between such proteins are viewed with caution (Pearson, 1996).

In an attempt to overcome some of the problems associated with employing sequence alignments to help predict protein function, several groups have developed databases of short, local sequence patterns (or "motifs") designed to help identify a given function or activity of a protein. These databases, notably "PROSITE" (Bairoch et at., 1997, Nuci. Acid Res., vol. 25:31–36), "Blocks" (Henikoff & Henikoff, 1994, Genomics, vol. 19:97–107), and "PRINTS" (Attwood & Beck, 1994, Nuci. Acids Res., vol. 22:3590–3596), use local sequence information (i.e., the sequence of several contiguous amino acid residues), as opposed to entire amino acid sequences, in order to try to identify sequence patterns that are specific for a given function.

Function prediction based on local sequence signatures, however, is plagued by the deficiencies that also limit the use of sequence alignment algorithms to predict protein function. Specifically, as sequence diversity within protein families increases, conventional databases of local sequence signatures may no longer recognize experimental protein sequences as belonging to a functional family (Fetrow and Skolnick, 1998, J. Mol. Biol., vol. 281:949–968). In proteins that are distantly related in terms of evolution, it is expected that only those residues required for the specific biological function of a protein will be conserved. That conservation will include not only sequence conservation, but also three-dimensional structural conservation (Holm and Sander, 1994, Proteins, vol. 19:165–173). However, local sequence motifs cannot recognize conserved three-dimensional structure—motifs can only recognize local sequence. Consequently, local sequence motifs may fail to be accurate predictors of protein function because function derives from three-dimensional structure. In other words, local sequence motif analysis is limited where function is dependent upon non-local residues, i.e., amino acids disposed in different regions of a protein's primary structure.

Many functional sites in proteins are known to comprise non-local residues. However, these residues are brought into functional association as a result of the protein assuming its folded three-dimensional structure, where different regions of the protein (in terms of linear amino acid sequence) may come together. For example, the three-dimensional structure of urease (a protein involved in nucleotide metabolism) was recently compared to those of adenosine deaminase and phosphotriesterase (Holm & Sander, 1997b), proteins that are also involved in nucleotide metabolism. Previous one-dimensional sequence comparisons failed to detect any relationship between these proteins; however, comparison of their three-dimensional structures showed conservation of active site structure. This same active site geometry was later observed in other nucleotide metabolism enzymes which exhibited an even greater diversity of overall sequence and tertiary structure (Holm & Sander, 1997b). In another example, it was determined that critical cysteine residues in the catalytic domain of ribonucleotide reductases were conserved across kingdom boundaries (Tauer & Benner, 1997). However, sequence alignment analysis did not reveal this relatedness because of the non-local nature of the conserved catalytic cysteine residues.

Various efforts have been made to overcome these limitations by, for example, extending local sequence patterns to include structural information. The goal of including such added information is to improve the ability of local sequence patterns to both detect distantly related proteins and differentiate between true and false positives. See, e.g., Kasuya, A. and Thornton, J. M., *J. Mol. Biol.*, vol. 286: 1673–1691 (1999). Others have postulated that the development of databases of 3D-templates, such as those that currently exist for local protein sequence motifs, may help to identify the functions of new protein structures as they are determined and pinpoint their functionally important regions. For example, Wallace, et al. (*Protein Science,* vol. 5:1001–1013 (1996)) reported the development of a 3D coordinate template for Ser-His-Asp the catalytic triad in serine proteases and triacylglycerol lipases. Initially, those authors selected a single "seed" catalytic triad from α-lyitc proteinase 1lpr (see Bone, et al., *Biochemistry,* vol. 30:10388–10398 (1991)), and coordinate positions were determined for all of the Ser and Asp side chain atoms, as well as for the positions of the atoms in the reference His residue. Root mean square distances (RMSDs) were then determined for all Ser and Asp side chain atoms in a set of serine proteases whose structures were also then known at atomic resolution. This analysis revealed that the positioning of a single oxygen atom in each of the Asp and Ser side chains was highly conserved. Using these data, a 3D template was developed for serine protease activity using the identity of three amino acids, namely Ser, His, and Asp, and the 3D coordinate positions (to an RMSD cut-off of 2 Å) for the functional oxygen atoms in the Ser and Asp side chains and the non-hydrogen atoms of the His side chain. The 3D template was then applied to a test set of high resolution protein structures drawn from the PDB database.

A major shortcoming of the foregoing 3D-template approach (see also Barth, et al. (1993) *Drug Design and Discovery,* vol. 10:297–317; Gregory, et al. (1993), *Protein Eng.,* vol. 6, no. 1:29–35; Artymiuk, et al. (1994), *J. Mol. Biol.,* vol. 243:327–344; and Fischer, et al. (1994), *Protein Sci.,* vol. 3:769–778), however, is that they require detailed knowledge of atomic positions (particularly for side chain atoms) in both the template structures and the test protein structure. This makes these 3D templates applicable only to high-resolution protein structures determined by x-ray crystallography or NMR spectroscopy. Less than atomic resolution structures and inexact models produced by current protein structure prediction algorithms cannot be analyzed by these methods.

In sum, conventional sequence-based function prediction methods fall short in the prediction of protein function from nucleotide or amino acid sequence information, in part because the technology frequently relies only on sequence information. Current structure-based methods said to have some utility for function prediction also fail in the analysis of sequences of unknown function, including genome sequences, because high-resolution structures, and their accompanying high level of atomic detail, are required. As such, there remains a need for better methods for predicting protein structure and function.

The inventions described and claimed herein solve these needs by providing novel methods and systems for predicting protein function from sequence. Various methods described and claimed herein use sequence and structure information and apply this information to protein structures, particularly inexact models of protein structure, that can be computationally derived from protein or nucleic acid sequences. Using their methods, the inventors have discovered that it is not necessary to accurately predict the overall three-dimensional structure of a particular protein of interest in order to predict its function. Instead, prediction of biological function using the methods described and claimed herein requires only an approximation of the three-dimensional orientation of two or more amino acid residues in a region responsible for the particular function of the protein under investigation. As such, this invention overcomes the problems and limitations of the methods previously utilized in an attempt to identify protein function from either sequence or structure. As those in the art will appreciate, such methods can routinely be adapted with respect to various protein functional sites in order to predict protein function. A more detailed description of the invention is provided below.

3. Definitions

The following terms have the following meanings when used herein and in the appended claims. Terms not specifically defined herein have their art recognized meaning.

As used herein, an "amino acid" is a molecule (see FIG. 1) having the structure wherein a central carbon atom (the alpha (α)-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino and carboxylic groups in the dehydration reaction that links one amino acid to another. As a result, when incorporated into a protein, an amino acid is referred to as an "amino acid residue." In the case of naturally occurring proteins, an amino acid residue's R group differentiates the 20 amino acids from which proteins are synthesized, although one or more amino acid residues in a protein may be derivatized or modified following incorporation into protein in biological systems (e.g., by glycosylation and/or by the formation of cystine through the oxidation of the thiol side chains of two non-adjacent cysteine amino acid residues, resulting in a disulfide covalent bond that frequently plays an important role in stabilizing the folded conformation of a protein, etc.). As those in the art will appreciate, non-naturally occurring amino acids can also be incorporated into proteins, particularly those produced by synthetic methods, including solid state and other automated synthesis methods. Examples of such amino acids include, without limitation, α-amino isobutyric acid, 4-amino butyric acid, L-amino butyric acid, 6-amino hexanoic acid, 2-amino isobutyric acid, 3-amino propionic acid, ornithine, norlensine, norvaline, hydroxproline, sarcosine, citralline, cysteic acid, t-butylglyine, t-butylalanine, phenylylycine, cyclohexylalanine, β-alanine, fluoro-amino acids, designer amino acids (e.g., β-methyl amino acids, α-methyl amino acids, Nα-methyl amino acids) and amino acid analogs in general. In addition, when an α-carbon atom has four different groups (as is the case with the 20 amino acids used by biological systems to synthesize proteins, except for glycine, which has two hydrogen atoms bonded to the α carbon atom), two different enantiomeric forms of each amino acid exist, designated D and L. In mammals, only L-amino acids are incorporated into naturally occurring polypeptides. Of course, the instant invention envisions proteins incorporating one or more D- and L- amino acids, as well as proteins comprised of just D- or L-amino acid residues.

Herein, the following abbreviations may be used for the following amino acids (and residues thereof): alanine (Ala, A); arginine (Arg, R); asparagine (Asn, N); aspartic acid (Asp, D); cyteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V). Non-polar (hydrophobic) amino acids include alanine, leucine, isoleucine, valine, proline, phenylalanine, tryptophan, and methionines. Neutral amino acids include glycine, serine, threonine, cysteine, tyrosine, esparagine, and glutamine. Positively charged (basic amino acids include arginine, lysine and histidine. Negatively charged (acidic) amino acids include aspartic acid and glutamic acid.

As used herein, a "β-carbon atom" refers to the carbon atom (if present) in the R group of the side chain of an amino acid (or amino acid residue) that is covalently bonded to the α-carbon atom of that amino acid (or residue). See FIG. 1. For purposes of this invention, glycine is the only naturally occurring amino acid found in mammalian proteins that does not contain a β-carbon atom.

A "biomolecule" refers to any molecule (including synthetic molecules) produced by a cell, found within a cell or organism, or which can be introduced into a cell or organism, or any derivative of such a molecule, and any other molecule capable of performing or having a biological function. Representative examples of biomolecules include nucleic acids and proteins. A "synthetic" biomolecule is one that has been prepared, in whole or part, through the use of one or more synthetic chemical reactions.

"Protein" refers to any polymer of two or more individual amino acids (whether or not naturally occurring) linked via a peptide bond, and occurs when the carboxyl carbon atom of the carboxylic acid group bonded to the α-carbon of one amino acid (or amino acid residue) becomes covalently bound to the amino nitrogen atom of amino group bonded to the α-carbon of an adjacent amino acid. See FIG. 1. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In simplest terms, the polypeptide backbone shall be understood to refer the amino nitrogen atoms, α-carbon atoms, and carboxyl carbon atoms of the protein, although two or more of these atoms (with or without their substituent atoms) may also be represented as a pseudoatom. Indeed, any representation representing a polypeptide backbone that can be used in a functional site descriptor as described herein will be understood to be included within the meaning of the term "polypeptide backbone."

The term "protein" is understood to include the terms "polypeptide" and "peptide" (which, at times, may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the invention and may be referred to herein as "proteins."

In biological systems (be they in vivo or in vitro, including cell-free, systems), the particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (which, for purposes of this invention, is understood to include organelle DNA, for example, mitochondrial DNA and chloroplast DNA). Of course, any type of nucleic acid which constitutes the genome of a particular organism (e.g., double-stranded DNA in the case of most animals and plants, single or double-stranded RNA in the case of some viruses, etc.) is understood to code for the gene product(s) of the particular organism. Messenger RNA is translated on a ribosome, which catalyzes the polymerization of a free amino acid, the particular identity of which is specified by the particular codon (with respect to mRNA, three adjacent A, G, C, or U ribonucleotides in the mRNA's coding region) of the mRNA then being translated, to a nascent polypeptide. Recombinant DNA techniques have enabled the large-scale synthesis of polypeptides (e.g., human insulin, human growth hormone, erythropoietin, granulocyte colony stimulating factor, etc.) having the same primary sequence as when produced naturally in living organisms. In addition, such technology has allowed the synthesis of analogs of these and other proteins, which analogs may contain one or more amino acid deletions, insertions, and/or substitutions as compared to the native proteins. Recombinant DNA technology also enables the synthesis of entirely novel proteins.

In non-biological systems (e.g., those employing solid state synthesis), the primary structure of a protein (which also includes disulfide (cystine) bond locations) can be determined by the user. As a result, polypeptides having a primary structure that duplicates that of a biologically produced protein can be achieved, as can analogs of such proteins. In addition, completely novel polypeptides can also be synthesized, as can protein incorporating non-naturally occurring amino acids.

In a protein, the peptide bonds between adjacent amino acid residues are resonance hybrids of two different electron isomeric structures, wherein a bond between a carbonyl carbon (the carbon atom of the carboxylic acid group of one amino acid after its incorporation into a protein) and a nitrogen atom of the amino group of the α-carbon of the next amino acid places the carbonyl carbon approximately 1.33 Å away from the nitrogen atom of the next amino acid, a distance about midway between the distances that would be expected for a double bond (about 1.25 Å) and a single bond (about 1.45 Å). This partial double bond character prevents free rotation of the carbonyl carbon and amino nitrogen about the bond therebetween under physiological conditions. As a result, the atoms bonded to the carbonyl carbon and amino nitrogen reside in the same plane, and provide discrete regions of structural rigidity, and hence conformational predictability, in proteins.

Beyond the peptide bond, each amino acid residue contributes two additional single covalent bonds to the polypeptide chain. While the peptide bond limits rotational freedom of the carbonyl carbon and the amino nitrogen of adjacent amino acids, the single bonds of each residue (between the α-carbon and carbonyl carbon (the phi ($\phi$) bond) and between the α-carbon and amino nitrogen (the psi ($\psi$) bond) of each amino acid), have greater rotational freedom. For example, the rotational angles for $\phi$ and $\psi$ bonds for certain common regular secondary structures are listed in the following table:

| Structure | Approximate Bond Angle $\phi$ | Approximate Bond Angle $\psi$ | Residues per turn | Helix pitch (Å)[a] |
|---|---|---|---|---|
| Right-handed α-helix (3.6$_{13}$ - helix) | −57 | −47 | 3.6 | 5.4 |
| 3$_{10}$ - helix | +49 | −26 | 3.0 | 6.0 |
| Parallel β-strand | −119 | +113 | 2.0 | 6.4 |
| Antiparallel β-strand | −139 | +135 | 2.0 | 6.8 |

[a]helix pitch refers to the distance between repeating turns on a line drawn parallel to the helix axis. Bond angles associated with other secondary structures are known in the art, or can be determined experimentally using standard techniques.

Similarly, the single bond between a α-carbon and its attached R-group provides limited rotational freedom. Collectively, such structural flexibility enables a number of possible conformations to be assumed at a given region within a polypeptide. As discussed in greater detail below, the particular conformation actually assumed depends on thermodynamic considerations, with the lowest energy conformation being preferred.

In addition to primary structure, proteins also have secondary, tertiary, and, in multisubunit proteins, quaternary structure. Secondary structure refers to local conformation of the polypeptide chain, with reference to the covalently linked atoms of the peptide bonds and α-carbon linkages that string the amino acids of the protein together. Side chain groups are not typically included in such descriptions. Representative examples of secondary structures include α helices, parallel and anti-parallel β structures, and structural motifs such as helix-turn-helix, β-α-β, the leucine zipper, the zinc finger, the β-barrel, and the immunoglobulin fold. Movement of such domains relative to each other often relates to biological function and, in proteins having more than one function, different binding or effector sites can be located in different domains. Tertiary structure concerns the total three-dimensional structure of a protein, including the spatial relationships of amino acid side chains and the geometric relationship of different regions of the protein. Quaternary structure relates to the structure and non-covalent association of different polypeptide subunits in a multisubunit protein.

A "functional site" refers to any site in a protein that has a function. Representative examples include active sites (i.e., those sites in catalytic proteins where catalysis occurs), protein-protein interaction sites, sites for chemical modification (e.g., glycosylation and phosphorylation sites), and ligand binding sites. Ligand binding sites include, but are not limited to, metal binding sites, co-factor binding sites, antigen binding sites, substrate channels and tunnels, and substrate binding sites. In an enzyme, a ligand binding site that is a substrate binding site may also be an active site.

A "pseudoatom" refers to a position in three dimensional space (represented typically by an x, y, and z coordinate set) that represents the average (or weighted average) position of two or more atoms in a protein or amino acid. Representative examples of a pseudoatom include an amino acid side chain center of mass and the center of mass (or, alternatively, the average position) of an α-carbon atom and the carboxyl atom bonded thereto.

A "reduced model" refers to a three-dimensional structural model of a protein wherein fewer than all heavy atoms (e.g., carbon, oxygen, nitrogen, and sulfur atoms) of the protein are represented. For example, a reduced model might consist of just the α-carbon atoms of the protein, with each amino acid connected to the subsequent amino acid by a virtual bond. Other examples of reduced protein models include those in which only the α-carbon atoms and side chain centers of mass of each amino acid are represented, or where only the polypeptide backbone is represented.

A "geometric constraint" refers to a spatial representation of an atom or group of atoms (e.g., an amino acid, the R-group of an amino acid, the center of mass of an R-group of an amino acid, a pseudoatom, etc.). Accordingly, such a constraint can be represented by coordinates in three dimensions, for example, as having a certain position, or range of positions, along x, y, and z coordinates (i.e., a "coordinate set"). Alternatively, a geometric constraint can be represented as a distance, or range of distances, between a particular atom (or group of atoms, etc.) and one or more other atoms (or groups of atoms, etc.). Geometric constraints can also be represented by various types of angles, including the angle of bonds (particularly covalent bonds, e.g., $\phi$ bonds and $\psi$ bonds) between atoms in an amino acid residue, between atoms in different amino acid residues, and between atoms in an amino acid residue of a protein and another molecule, e.g., a ligand, with ranges for each angle being preferred.

A "conformational constraint" refers to the presence of a particular protein conformation, for example, an α-helix, parallel and antiparallel β strands, leucine zipper, zinc finger, etc. In addition, conformational constraints can include amino acid sequence information without additional structural information. As an example, "—C—X—X—C—" is a conformational constraint indicating that two cysteine residues must be separated by two other amino acid residues, the identities of each of which are irrelevant in the context of this particular constraint.

An "identity constraint" refers to a constraint of a functional site descriptor that indicates the identity of an amino acid residue at a particular location in a protein. (determined by counting the number of amino acid residues in the protein from its amino terminus up to and including the residue in question). As those in the art will appreciate, comparison between related proteins may reveal that the identity of a particular amino acid residue at a given amino acid position in a protein is not entirely conserved, i.e., different amino acid residues may be present at a particular amino acid position in related proteins. In such instances or, alternatively, when an artisan desires to relax the constraint, two or more alternative amino acid residue identities can be provided for a particular identity constraint of a functional site descriptor. Of course, in such cases the invention also envisions different functional site descriptors for the particular biological function that differ by employing different amino acid residue identities (or sets of identities) for the corresponding position. For example, where it is determined by sequence alignment that related proteins have one of two amino acid residues at a particular position in the functional site, a single functional site descriptor therefor may specify the two alternatives. Alternatively, two different functional site descriptors may be generated that differ only with respect to the identity constraint at that position. Similar strategies can be employed with regard to other constraints used in a functional site descriptor according to the invention.

To "relax" a constraint refers to the inclusion of a user-defined variance therein. The degree of relaxation will depend on the particular constraint and its application. As those in the art will appreciate, functional site descriptors for the same biological function can be developed wherein different degrees of relaxation for one or more constraints are what differentiate one such descriptor from another.

Protein structures useful in the practice of the invention can be of different quality. The highest quality determination methods are experimental structure prediction methods based on x-ray crystallography and NMR spectroscopy. In x-ray crystallography, "high resolution" structures are those wherein atomic positions are determined at a resolution of about 2 Å or less, and enable the determination of the three-dimensional positioning of each atom (or each non-hydrogen atom) of a protein. "Medium resolution" structures are those wherein atomic positioning is determined at about the 2–4 Å level, while "low resolution" structures are those wherein the atomic positioning is determined in about the 4–8 Å range. Herein, protein structures that have been determined by x-ray crystallography or NMR may be referred to as "experimental structures," as compared to those determined by computational methods, i.e., derived from the application of one or more computer algorithms to a primary amino acid sequence to predict protein structure.

As alluded to above, protein structures can also be determined entirely by computational methods, including, but not limited to, homology modeling, threading, and ab initio methods. Often, models produced by such computational methods are "reduced" models, i.e., the predicted structures (or "models") do not include all non-hydrogen atoms in the protein. Indeed, many reduced models only predict structures that show the polypeptide backbone of the protein, and such models are preferred in the practice of the invention. Of course, it is understood that once a protein structure based on a reduced model has been generated, all or a portion of it may be further refined to include additional predicted detail, up to including all atom positions.

Computational methods usually produce lower quality structures than experimental methods, and the models produced by computational methods are often called "inexact models." While not necessary in order to practice the instant methods the precision of these predicted models can be determined using a benchmark set of proteins whose structures are already known. The predicted model for each biomolecule may then be compared to a corresponding experimentally determined structure. The difference between the predicted model and the experimentally determined structure is quantified via a measure called "root mean square deviation" (RMSD). A model having an RMSD of about 2.0 Å or less as compared to a corresponding experimentally determined structure is considered "high quality". Frequently, predicted models have an RMSD of about 2.0 Å to about 6.0 Å when compared to one or more experimentally determined structures, and are called "inexact models". As those in the art will appreciate, RMSDs can also be determined for one or more atomic positions when two or experimental structures have been generated for the same protein.

SUMMARY OF THE INVENTION

The object of this invention is to enable one or more functions of a protein to be predicted from structural information, for example, from computationally derived models of protein structure (including inexact models) produced from deduced primary amino acid sequences, for example, as may be derived from nucleotide sequence of a novel gene obtained in the course of genome sequencing projects.

The present invention comprises a number of objects, aspects, and embodiments.

One aspect of the invention concerns functional site descriptors (FSDS) that define spatial configurations for protein functional sites that correspond with particular biological functions. It is known that function derives from structure. A functional site descriptor according to the invention provides three-dimensional representation of protein functional site. In some embodiments, the functional site represented by an FSD is a ligand binding domain (e.g., a domain that binds a ligand, for example, a substrate, a co-factor, or an antigen), while in other embodiments, the functional site is a protein-protein interaction site or domain. In certain preferred embodiments, the functional site is an enzymatic active site. Particularly preferred embodiments concern functional sites other than a divalent metal ion binding site.

A functional site descriptor typically comprises a set of geometric constraints for one or more atoms in each of two or more amino acid residues comprising a functional site of a protein. Preferably, at least one of said two or more amino acid residues is also identified as a particular amino acid residue or set of amino acid residues. In preferred embodiments, the said one or more atoms is selected from the group consisting of amide nitrogens, α-carbons, carbonyl carbons, and carbonyl oxygens within a polypeptide backbone, β-carbons of amino acid residues, and pseudoatoms. In particularly preferred embodiments, at least one of said one or more atoms is an amide nitrogen, an α-carbon, a β-carbon, or a carbonyl oxygen within a polypeptide backbone.

In certain embodiments, a functional site descriptor represents 3, 4, 5, 6, 7, 8, 9, 10, 11, 12, 13, 14, or 15 amino acid residues (or sets of residues) that comprise the corresponding the functional site. While an FSD may include one or more identity constraints with respect to any amino acid, such constraints preferably make reference to naturally occurring amino acids, particularly naturally occurring L amino acids, including those selected from the group consisting of Ala, Arg, Asn, Asp, Cys, Gln, Glu, Gly, His, Ile, Leu, Lys, Met, Phe, Pro, Ser, Thr, Trp, Tyr, and Val.

The geometric constraints of an FSD preferably are selected from the group consisting of an atomic position specified by a set of three dimensional coordinates, an interatomic distance (or range of interatomic distances), and an interatomic bond angle (or range of interatomic bond angles). When a geometric constraint refers to atomic position, reference is typically made to a set of three dimensional coordinates. Such constraints preferably relate to RMSDs, particularly those that allow the atomic position to vary within a preselected RMSD, for example, by an amount of less than about 3 Å, less than about 2.5 Å, less than about 2.0 Å, less than about 1.5 Å, and less than about 1.0 Å.

Other geometric constraints concern interatomic distances, preferably interatomic distance ranges, or interatomic bond angles range preferably interatomic bond angle ranges.

In some embodiments, an FSD can also include one or more conformational constraints that refer to the presence of a particular secondary structure, for example, a helix, or location, for example, near the amino or carboxy terminus of a protein.

In preferred embodiments, an FSD refers to at least one atom from each of 4, 5, 6, 7, 8, 9, 10, 11, 12, 13, 14, or 15 amino acid residues that comprise the corresponding functional site. In many embodiments, all of the atoms for which geometric constraints are provided comprise a part of the polypeptide backbone and are selected from the group consisting of α-carbons, amide nitrogens, carbonyl carbons, and carbonyl oxygens. Of course, one or more of such atoms can be a pseudoatom. Representative examples of pseudoatoms are centers of mass, such as may be derived from at least two atoms, such as two or more atoms from one amino acid residue or two or more atoms from at least two amino acid residues of the protein.

Particularly preferred FSDs are those comprising multiple geometric constraints. Representative examples of such FSDs are a three atom functional site descriptor, a four atom functional site descriptor, a five atom functional site descriptor, a six atom functional site descriptor, a seven atom functional site descriptor, an eight atom functional site descriptor, a nine atom functional site descriptor, a ten atom functional site descriptor, an eleven atom functional site descriptor, a twelve atom functional site descriptor, a thirteen atom functional site descriptor, a fourteen atom functional site descriptor, and a fifteen atom functional site descriptor.

Preferably, FSDs according to the invention are implemented in electronic form.

Certain embodiments of the invention also concern libraries of FSDs, in electronic or other form. Preferably, such a library comprises at least two functional site descriptors for at least one of the biological functions represented by the library.

Another aspect of the invention concerns methods of identifying a protein as having a particular biological function. Such methods may also be referred to as function screening methods. Typically, such methods comprise applying a functional site descriptor according to the invention to a structure of a protein and determining whether the protein has the biological function. This determination is made if application of the functional site descriptor reveals that a portion of the structure of the protein matches, or satisfies, the constraints of the functional site descriptor.

In some embodiments of such methods, the structure(s) to which one or more FSDs is(are) applied is(are) of high resolution. High resolution structures can be obtained by a variety of methods, including x-ray crystallography and nuclear magnetic resonance.

Preferred embodiments involve application of one or more FSDs to predicted protein structures, especially inexact, three dimensional structural protein models. Such models can be generated by a variety of techniques, including by application of an ab initio folding program, a threading program, or a homology modeling program.

FSDs can be applied to a protein structures derived from any organism, be they prokaryotic or eukaryotic. Prokaryotic organisms the proteins of which may be screened according to the instant methods include bacteria. Eukaryotic organisms include plants and animals, particularly those of medical or agricultural import. A representative class is mammals, including bovine, canine, equine, feline, ovine, porcine, and primate animals, as well as humans. The methods may also be applied to study viral protein function.

In certain embodiments, the methods of the invention are practiced using plurality of functional site descriptors and/or
  a plurality of proteins structures, of the same or different proteins, preferably to a plurality of structures for a plurality of proteins.

Another aspect of the invention concerns methods of making FSDs for functional sites of proteins (other than divalent metal ion binding sites), which FSDs can then be applied to inexact, three dimensional structural proteins models.

Yet another aspect concerns computer program products comprising a computer useable medium having computer program logic recorded thereon for creating a functional site descriptor for use in predicting a biological function of a protein. Such computer program logic preferably comprises computer program code logic configured to perform a series of operations, including determining a set of geometric constraints for a functional site associated with a biological function of a protein; modifying one or more geometric constraints of said set of geometric constraints to produce a modified set of geometric constraints; comparing said modified set of geometric constraints to a data set of functional sites correlated with said biological function to determine whether said modified set of geometric constraint compares favorably with said data set of functional sites correlated with said biological function and, if so; comparing said modified set of geometric constraint(s) to a data set of functional sites not correlated with said biological function to determine whether said modified set of geometric constraints compares favorably with said data set of functional sites not correlated with said biological function and, if so; repeating said modifying and comparing operations to modify one or more of said geometric constraints of said set of geometric constraints to an extent that said modified set of geometric constraints compares favorably with said data set of functional sites correlated with said biological function without encompassing a predetermined amount of data sets not correlated with said biological function.

In preferred embodiments, the operation of determining a set of geometric constraints of a functional site correlated with a biological function of a protein comprises receiving said set of geometric constraints from at least one of the group of a data set of predetermined geometric constraints or from user input. When modifying one or more geometric constraints of said set of geometric constraints to produce a modified set of geometric constraints, a predetermined variance can be associated with one or more of the geometric constraints to adjust the same.

In preferred embodiments, the operation of modifying one or more geometric constraints of said set of geometric constraints to produce a modified set of geometric constraints comprises computing an average value for a geometric constraint within the set of geometric constraints by determining values for said geometric constraint from two different proteins having functional sites that correlate with said biological function, and calculating said average value; computing a standard deviation with respect to such geometric constraint; and applying a multiplier to said computed standard deviation to generate said modified geometry.

Other features and advantages of the invention will be apparent from the following description of the preferred embodiments thereof, and from the claims.

BRIEF DESCRIPTION OF THE FIGURES

FIG. 6, which comprises FIGS. 6A, 6B and 6C: Residue 84 is the primary residue and residue 3 is the secondary residue in FIGS. 6A and 6B. The primary and secondary residues are more generally designated as "A" and "B", respectively, as shown in FIG. 6C.

FIG. 8 is a diagram illustrating an example data set for a functional site descriptor according to one embodiment of the invention. In this figure, A is the primary residue, B is the secondary residue, and C is the tertiary residue, as also illustrated in FIG. 6C.

FIG. 12/1 shows an alignment of 12 amino acid sequences, as well as the constraint sets for an FSD. FIG. 12/2 shows the values of the distance parameters from an analysis of three T1 ribonucleases.

DETAILED DESCRIPTION

Figure 1:
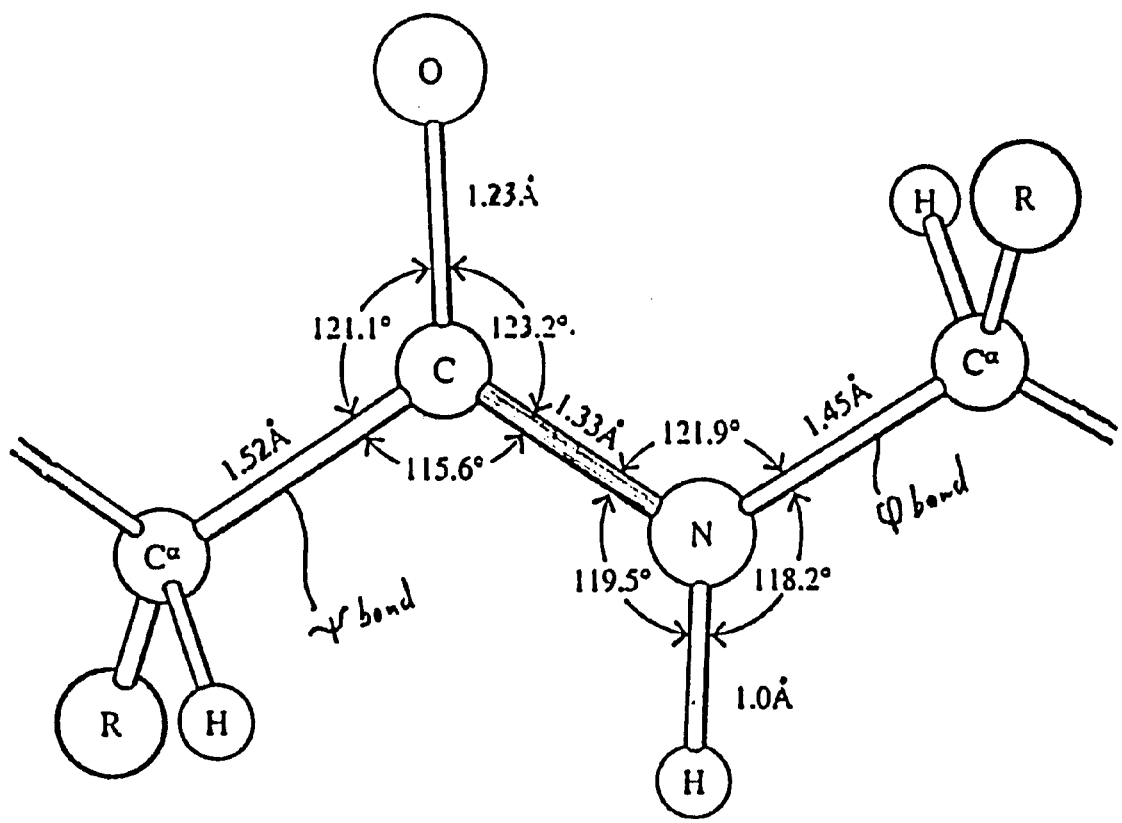
FIG. 1 illustrates the structure and geometry of a polypeptide backbone. All atoms between the two α-carbon atoms of two adjacent amino acid residues are shown. The peptide bond between the carbonyl carbin of one amino acid residue and the amide nitrogen of the adjacent amino acid is shaded. The dimensions and bond angles shown are averages observed crystallographically in amino acids and shall peptides. (Ramachandran, et al. (1974) *Biochim. Biophys. Acta.,* 359:298–302). The position of the ψ and Ø bonds are also shown.

According to the invention, one or more functional site descriptors, preferably relaxed functional site descriptors, can be developed for a biomolecule functional site having a specific biological function. Libraries of such descriptors (preferably implemented in electronic form) can be used to probe for or evaluate the activity or function associated with the functional site descriptor in one or more protein structures. Advantageously, such protein structures may be represented as inexact structural models. As a result, the instant invention has many applications. For example, the invention can be used to identify or screen for a novel function in one or more proteins, to confirm a previously identified or suspected function of a protein, or to provide further information about a specific functional site in a protein. Such additional information includes, but is not limited to, information about specific active site residues, substrate Specificity, or regulatory processes.

Descriptors of protein functional sites, termed "functional site descriptors," are defined based on various constraints (or "parameters"), including, but not limited to, atomic or molecular geometry and residue identity. Preferably, such parameters are derived from functional sites of proteins of known, high-resolution structure. The descriptors of the invention thus enable identification of functional sites not only from experimentally determined structures, but, significantly, also from predicted structures, including inexact protein models predicted by ab initio folding algorithms, threading algorithms, homology modeling algorithms, or other protein structure prediction algorithms.

Functional Site Descriptors

Functional site descriptors define a spatial configuration for a protein functional site that corresponds to a biological function. Functional site descriptors according to the invention comprise, at a minimum, a spatial representation or configuration of at least two atoms, or groups of atoms. By way of example, a functional site descriptor may be prepared using the interatomic distance, or preferably, a range of interatomic distances, between the α-carbon atoms of two amino acid residues known or suspected to be involved in the catalysis carried out by a particular enzyme. Alternatively, such a configuration can be represented in three dimensions using x, y, and z coordinates to identify the position, or range of positions, that a particular atom may have relative to other functionally important residues.

The identity of each functionally important amino acid residue, distance (or range of distances) between atoms or pseudoatoms, coordinate set, or other parameter represents a constraint with respect to the particular functional site descriptor. Preferably, a functional site descriptor will include one or more identity constraints, for example, the identity of a particular amino acid residue (or set of amino acid residues) located or predicted to be located at a particular position in a protein, in addition to a set of two or more geometric constraints. As those in the art will appreciate, other information can also be included for a particular functional site descriptor, for example, information regarding bond angles (or bond angle ranges), secondary structure information, amino acid sequence, etc. Whether, and to what extent, such or other information is included in a particular functional site descriptor is within the discretion of those in the art given the particular context.

A variety of functional site descriptors can be developed in accordance herewith, and they can be used in a variety of applications, some of which are described herein and others which will be apparent to those skilled in the art upon review of the instant specification. Certain preferred embodiments employ RMSDs for one or more atoms or pseudoatoms of each of two or more amino acid residues identified as comprising at least a portion of the functional site corresponding to the particular functional site descriptor. Other preferred embodiments utilize interatomic distances (particularly distance ranges) between atoms (or pseudoatoms) of different amino acid residues as geometric constraints. For example, distances between one or more atoms (e.g., α-carbon atoms, α-carbon atoms and β-carbon atoms, α-carbon atoms and pseudoatoms representing side chain centers of mass) of two or more amino acid residues identified as comprising a part of the particular functional site can be employed as geometric constraints. In other embodiments, a functional site descriptor comprises a mixture of geometric constraints, some of which are based on RMSDs, while others address interatomic distance ranges. Indeed, the particular composition of constraints in a given functional site descriptor is left to the discretion of the artisan. Moreover, a plurality (i.e., two or more) functional site descriptors comprising different constraints can be developed for the same function, and they may be used in combination, alternatively, or in some variation thereof in practicing certain of the methods of the invention.

With regard to functional site descriptors for active sites of enzymatic proteins, a functional site descriptor can be prepared as follows: For example, it is preferred to identify at least two, and preferably three or more (e.g., 3, 4, 5, 6, 7, 8, 9, 10, 11, 12, 13, 14, 15, 16, 17, 18, 19, or 20), amino acid residue positions, and the amino acid residue(s) at those positions, known or suspected to be involved in the enzyme's catalytic activity or maintenance of the active site. After the key positions and residues are identified (for each amino acid residue, its respective "residue identity constraint"), their location is determined in the three dimensional structure of at least one, and preferably 2, 3, 4, 5, or more proteins, known to possess the particular catalytic activity. Of course, other active site residues could also be employed in this process, although it is preferred to use the catalytic or structurally conserved residues because of their tendency to be conserved across evolutionary distances.

After the locations (and hence identities) of the particular key amino acid residues in the functional site descriptor are determined (each of these being identity constraints, at least one of which will ultimately be used in the functional site descriptor), a set of geometric constraints that relates each of them to at least one, and preferably all, of the others in the descriptor is developed. As those in the art will appreciate, when the positions of such residues are identified in two or more distinct proteins having the same catalytic activity, the positions of these residues, and particularly the positions of the atoms (or pseudoatoms) of these residues, will often vary slightly due to atomic and molecular movement inherent in complex structures. Such variances can be represented as geometric constraints, expressed as RMSDs. An RMSD defines the three dimensional location of a particular atom or pseudoatom within a particular range in one or more of x, y, and z coordinates. RSMDs useful in the practice of the invention are most frequently less than about 10 Å, preferably less than about 5 Å, even more preferably less than about 3 Å, and even more preferably less than about 2.5 Å to about 0.5 Å. While RSMDs as small as about 0.1 Å can be used, they are less preferred.

In other embodiments of the invention, the geometric constraints used to define spatial representations of atoms or pseudoatoms of a functional site descriptor utilize distances between one or more atoms of key amino acid residues relative to each other. For example, a distance constraint between two α-carbon atoms will typically include the average distance between the two atoms as well as the standard deviation for such distance. In preferred embodiments, the range of distances for any particular spatial or geometric constraint is maximized, but preferably only to the extent that specificity toward identification of the desired functional sites is maintained. In practice, it has been found in most cases that the standard deviation for a particular distance or other geometric constraint can be increased by a multiple. In preferred embodiments, a user-defined, pre-selected multiple selected from the group consisting of 0.5 to 10 in increments of 0.1 may be applied to one or more geometric constraints of a functional site descriptor.

In addition, it is preferred that distance and other spatial or geometric constraints be represented as ranges (i.e., an RMSD or minimum and maximum allowed distance between two atoms, molecules, residues, side chains, or other positions in coordinate space).

For example, a functional site descriptor for an active site of an enzyme may comprise one, and preferably two, three, or more primary residue identity constraints (e.g., the allowed identities of three amino acids having a role in the enzyme's catalytic function). Such a descriptor might also be composed of at least three distance constraints, namely the distance ranges between the three amino acids comprising the primary residue identity constraints.

Figure 5:
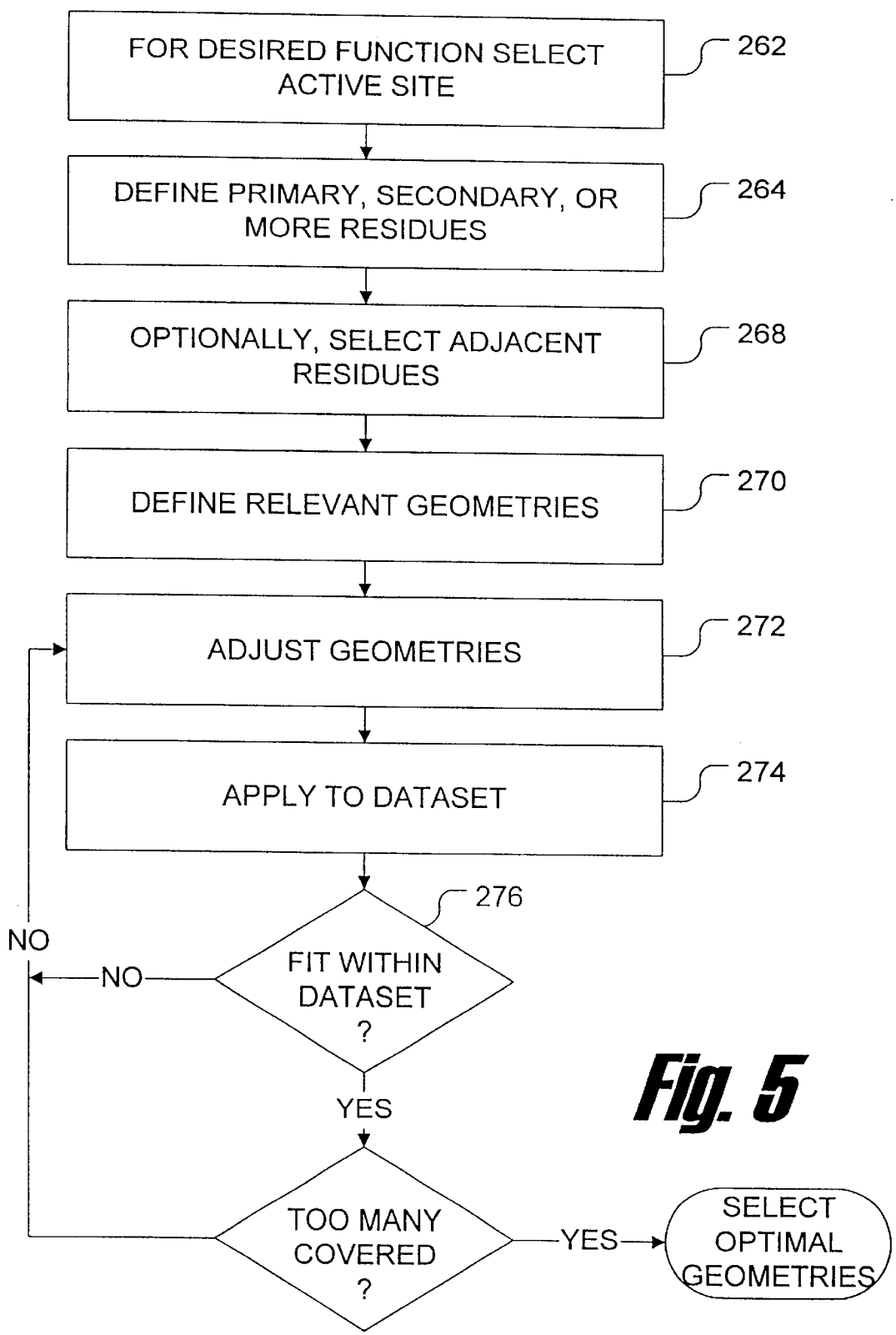
FIG. 5 is an operational flow diagram illustrating a method for creating a functional site descriptor according to one embodiment of the invention.

When necessary or desirable to achieve further functional site selectivity and specificity, additional distance and/or residue identity constraints may be employed. For example, functional site descriptors comprising two to about 50 or more geometric constraints can be developed for a particular biological function. In many embodiments, the number of geometric constraints in a functional site descriptor is from about 4–25, often from about 5–20. For example, a so-called "9-distance" constraint set for an enzyme active site that correlates with a biological function can be employed in conjunction with three primary residue identity constraints (illustrated, for example, in FIG. 5). In this example, the functional site descriptor comprises the distance ranges between the α-carbon atoms of the three amino acids making up the primary residue identity constraints (three distance constraints) and six additional distance ranges. The three primary residues are designated A, B, and C for purposes of the geometric constraints. The additional distance ranges could be determined by identifying the positions of the α-carbon atoms of the amino acids immediately before and after each of the three amino acids of the primary residue identity constraint according to primary sequence, as illustrated in FIG. 5. In such case, the additional residues could be designated as A−1 and A+1, B−1 and B+1, and C−1 and C+1, for residues that immediately precede and follow residues A, B, and C (as determined by amino acid position in the primary sequence of the protein), respectively. In this example, after identifying these positions, or the ranges for these positions, six or more different distance ranges are determined between these secondary α-carbons and the primary α-carbons and/or other of the secondary α-carbons. If two or more structures are examined for purposes of obtaining these distances, it is often useful to calculate the standard deviation in these distances for purposes of establishing distance ranges. In preferred embodiments, the ranges are increased by applying a multiplier to the upper and/or lower end of the calculated standard deviation range. This multiplier can be any number, although it preferably is between about 0.5 and 10. Often, a suitable multiplier will be 2.0. As those in the art will appreciate, the number of constraints included in a particular functional site descriptor will vary depending upon the number desired or required to distinguish the particular descriptor from descriptors (or structures) for, or which correlate with, other biological functions. Preferably, a functional site descriptor according to the invention will comprise the fewest constraints possible to achieve the selectivity and specificity desired for the particular functional site descriptor. Of course, after a particular descriptor has been defined, additional information may become known which will facilitate or necessitate further refinement, or inclusion of one or more additional constraints, of the descriptor. Preferably, a functional site descriptor will allow all proteins having the particular biological function that corresponds to the descriptor to be identified in the set of proteins being examined ("selectivity"), without identifying proteins that do not have the function ("specificity").

Figure 4:
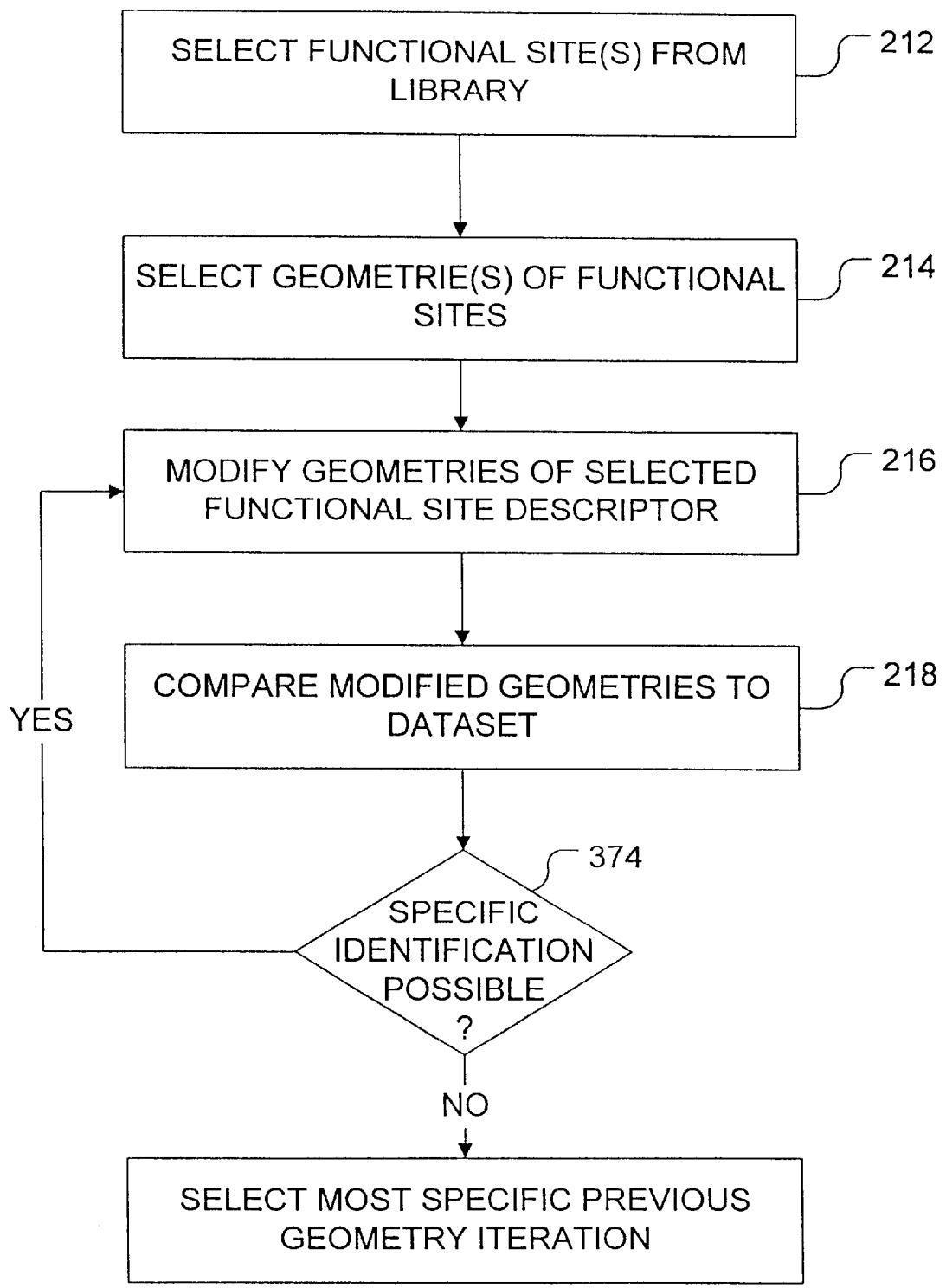
FIG. 4 is an operational flow diagram illustrating a process for creating a functional site descriptor for a given function according to one embodiment of the invention.

Functional site descriptors according to the invention can be produced, for example, by the following steps, as outlined in FIG. 4. Initially, the functionally and structurally important residues are identified (step 212). This could be done, for example, by a search of the scientific literature regarding a particular biomolecule to provide biochemical evidence about which residues are or may be important for a particular biological function of such biomolecule. This information could also be obtained via scientific experiment or other analysis. For example, identification of residues which are important or required for a biological activity can be identified by, for example, site directed mutagenesis experiments.

Next, one, and preferably more, proteins are selected that possess the particular function and for which an experimentally determined three dimensional structure (preferably a high resolution structure) is known. The putative functionally important residues are identified in the known three-dimensional structure(s), and the relative geometries (e.g., distances, angles) between atoms or group of atoms, for example, the α-carbons of each of the functionally important amino acids of a protein, are recorded. In some cases, it may also be desirable to record spatial information with respect to other moieties, for example, the distances (or distance ranges) between side chain centers of mass of these or other amino acids in the protein. If available, other structural information, such as secondary structural information, may also be included in the descriptor if there is evidence for the importance of such information. However, it is preferred not to include such information unless it is required to provide the requisite selectivity and specificity for the particular functional site descriptor. Structural superposition and multiple sequence alignment may help identify other residues that might be important in the particular biological function under consideration, but these procedures are generally used only where experimental evidence suggests a functional significance.

The functional site descriptor building procedure is iterative. After identification of conserved residues (or sets of residues), another analysis may be performed to determine the relative functional importance of the conserved residues (or sets of residues) within the structures. As those in the art will appreciate, in a functional site descriptor for a protein, the aim is to use only those residues known to be functionally important or conserved across one or more proteins exhibiting the function or activity of interest. Moreover, it is desirable to use the minimum number of possible parameters in the descriptor, it being understood that the descriptor should be sensitive enough to enable the identification of corresponding functional sites in biomolecules while at the same time having the specificity to detect only those sites and not others having a similar configuration but lacking the desired biological function in other biomolecules.

Once a set of identity, geometric, and/or conformational constraints (it being understood that other constraint types can also be included, if desired, in a particular descriptor) for a specific function have been determined, they are preferably implemented in electronic form as described below. One or more of these descriptors can then be used to probe (preferably via computer) one or more experimentally determined protein structures for sets of residues that satisfy, or match, the specified constraints. Experimentally determined protein structures could be, for example, those determined by x-ray crystallography or NMR spectroscopy, which might be stored in a repository, such as Brookhaven PDB (Abola et al., 1987). The constraints are preferably implemented stepwise, so that structures that are eliminated by each criterion may be evaluated at each step along the way.

If a constraint set adopted as a functional site descriptor for a particular biological function misses or fails to identify any protein within the experimentally determined structures known or suspected to exhibit the particular biological function under investigation, the structure of the missed protein, particularly the structure of the functional site correlated with the desired biological function, is analyzed. One or more of the constraints comprising the functional site descriptor is then modified or relaxed so that the biomolecule exhibiting the function is correctly identified upon re-testing. "Relaxation" of a functional site descriptor constraint or parameter, e.g., the distance between the α-carbons of two functionally important amino acids, refers to the range of numbers embodied by the particular parameter. Ideally, such relaxation should not degrade the performance of the functional site descriptor in identifying proteins having the desired biological function on high resolution structures. For example, if the initial functional site descriptor for a particular enzymatic activity fails to identify an enzyme in the selected structural database known to exhibit the desired biological function because one or more of the atoms selected as being relevant to that function lies at a distance beyond that allowed for by one or more constraints of the functional site descriptor, the constraint set for the descriptor is modified to include such a distance. Indeed, it is preferred if one or more or all members of the constraint set are adjusted to allow, in the case of spatial constraints (e.g., distance constraints, bond angle constraints, etc.), the greatest possible latitude between relevant atoms (or groups of atoms, etc.) without leading to the identification of proteins lacking the desired function but exhibiting a related structure.

In addition, even if a particular functional site descriptor is determined to have the requisite selectivity and specificity for its target biological function, it may be still be desirable to further relax one or more of the constraints of the descriptor, so long s the desired level of selectivity and specificity are maintained. For example, in application to further experimentally determined or modeled structures, it may be necessary or desirable to further relax one or more constraints in the descriptor to accommodate ambiguities inherent in medium, low-resolution, or inexact models. Thus, the extent of parameter relaxation may be ascertained by testing against various structures, for example, against exact structures (i.e., high-resolution experimentally determined models) and against inexact, predicted models of protein structures. As those in the art will appreciate, it is desirable to relax one or more parameters of a functional site descriptor to the maximum extent possible, in other words, to identify all biomolecules of known structure having the desired function without identifying a biomolecule known not to have (or that does not have) the desired function. As the structures of more biomolecules having the known biological function are identified, existing functional site descriptors can be probed against such structures, and refined, or relaxed (or perhaps both, on a parameter-by-parameter basis), if needed or desired.

If the functional site descriptor selects one or more proteins not known to display the function, then the structure of any such "false positive" example is compared to the known functional sites. In such cases, there are two possible outcomes. In the first case, the functional descriptor has identified a functional site that was not previously recognized in the protein. In the second case, the functional descriptor has incorrectly identified a functional site. In this second case, one or more constraints of the functional site descriptor are modified (for example, in the case of distance constraints, one or more distance constraints is adjusted by altering the interatomic distance ranges between relevant atoms or groups or groups of atoms to eliminate the false positives. Various sequence, structural, and experimental analysis are utilized to distinguish between these two cases.

Using the methods described above and elsewhere herein, a putative functional site descriptor is generated. Preferably, the descriptor is validated for selectivity and specificity using a test set of proteins, some of which possess the biological function corresponding to the descriptor, and some of which do not. This descriptor may be applied to experimentally determined or modeled structures.

Proteins

Under physiological conditions, each protein assumes a "native conformation," a unique secondary and tertiary (and quaternary conformation in the case of multisubunit proteins) conformation dictated by the protein's primary structure. The folding of a protein typically is spontaneous and under the control of non-covalent forces, and results in the lowest free energy state kinetically available under the particular pH, temperature, and ionic strength conditions. Disulfide bonds are typically formed after folding occurs, and serve to stabilize the native conformation. However, it is known that proteins having unrelated biological function or sequence can have similar patterns of secondary structure in the tertiary structure of different domains.

General protein folding parameters play an important role in predicting protein folding, and are based on observations that a protein's native conformation is spontaneously assumed by non-covalent interactions, although interactions with other proteins, for example, chaperoning, may be required for the proper folding of some proteins. Non-covalent interactions are weak bonding forces having bond strengths that range from about 4 to about 29 kcal/mol, which exceed the average kinetic energy of molecules at 37° C. (about 0.6 kcal/mol). In contrast, covalent bonds have bond strengths of least about 50 kcal/mol. While individually weak, the large number of non-covalent interactions in a polypeptide having more than several amino acids add up to a large thermodynamic force favoring folding.

Protein folding parameters include, among others, those relating to relative hydrophobicity, i.e., preference for the hydrophobic environment of a non-polar solvent. See *Textbook of Biochemistry with Clinical Correlations*, $3^{rd}$ Ed., ed. Devlin, T. M., Wiley-Liss, p. 30 (1992)). Hydrophobic interactions are believed to occur not because of attractive forces between non-polar groups, but from interactions between such groups and the water in which they are, or otherwise would be, dissolved. The salvation shell (a highly ordered, and therefore thermodynamically disfavored, arrangement of water molecules around a non-polar group) around a single residue is reduced when another non-polar residue becomes positioned nearby during folding, releasing water in the salvation shell into the bulk solvent and thereby increasing the entropy of water solvent. It is estimated that approximately one-third of the ordered water molecules in an unfolded protein's salvation shell are lost into the bulk solvent upon formation of a secondary structure, and that about another one-third of original salvation water molecules are lost when a protein having a secondary structure folds into its tertiary structure.

Amino acid residues preferring hydrophobic environments tend to be "buried," i.e., those found at least about 95% of the time within the interior of a folded protein, although positioning on the exterior surface of a globular protein can occur by placing the more polar components of the amino acid near the exterior surface. The clustering of two or more non-polar side chains on the exterior surface are generally associated with a biological function, e.g., a substrate or ligand binding site. Polar amino acids are typically found on the exterior surface of globular proteins, where water stabilizes the residue's polarity. Positioning of an amino acid having a charged side chain in a globular protein's interior typically correlates with a structural or functional role for that residue with respect to biological function of the protein.

Another important protein folding parameter concerns hydrogen bond formation. A hydrogen bond (having bonding energies between about 1 to about 7 kcal/mol) is formed through the sharing of a hydrogen atom between two electronegative atoms, to one of which the hydrogen is covalently bonded (the hydrogen bond "donor"). Hydrogen bond strength depends primarily on the distance between the hydrogen bond donor and acceptor atoms, with high bond energies occurring when the donor and acceptor atoms are from about 2.7 Å to about 3.1 Å apart. Also contributing to hydrogen bond strength is bond geometry. Bonds having high energies typically have the donor, hydrogen, and acceptors disposed in a colinear fashion. The dielectric constant of the medium surrounding the bond can also influence bond strength.

Electrostatic interactions (positive and negative) between charged amino acid residues also play a role in protein folding and substrate binding. The strength of these interactions varies directly with the charge on each ion and inversely with the solvent's dielectric constant and distance between the charges.

Other forces to consider in protein folding concern van der Waals forces, which involve both attractive and repulsive forces that depend on the distances between atoms. Attraction is believed to occur through induction of a complementary dipole in the electron density of adjacent atoms when electron orbitals approach at close distances. The repulsive component, also called steric hindrance, occurs at closer distances when neighboring atoms' electron orbitals begin to overlap. With regard to these forces, the most favorable interaction occurs at the van der Waals distance, which is the sum of the van der Waals radii for the two atoms. Van der Waals distances range from about 2.8 Å to about 4.1 Å. While individual van der Waals interactions usually have an energy less than 1 kcal/mol, the sum of these energies for even a protein of modest size is significant, and thus these interactions significantly impact protein folding and stability, and, ultimately, function.

Yet another interaction playing a role in protein folding and function concerns that which occurs when two or more aromatic rings approach each other such that the plane of the π electron orbitals of the aromatic rings overlap. Such interactions can have attractive, non-covalent forces of up to about 6 kcal/mol.

Other factors to consider in determining folding of proteins include the presence or absence of co-factors such as metals (e.g., $Zn^{2+}$, $Ca^{2+}$, etc.), as well as other consideration known in the art.

Thermodynamic and kinetic considerations control the protein folding process. Without being tied to a particular theory, it is believed that folding begins through short range non-covalent interactions between several adjacent (as determined by primary structure) amino acid side chain groups and the polypeptide chain to which they are covalently linked. These interactions initiate folding of small regions of secondary structure, as certain R groups have a propensity to form α-helices, β structures, and sharp, turns or bends in the polypeptide backbone. Medium and long range interactions between more distant regions of the protein then come into play as these distant regions become more proximate as the protein folds.

As discussed herein, functional site descriptors according to the invention can be developed for any biological function of a protein. Such functions include, but are not limited to, catalysis, ligand binding, and protein-protein interaction. Typically, a protein biological function is carried our, or provided for, by one or more specific sites or regions of a protein, and the functionality of such sites are dictated by the three-dimensional structure of the protein.

Functional sites of a particular interest in the context of this invention include enzyme active sites, ligand binding sites, and protein-protein interaction sites. Preferred ligand binding sites include substrate binding sites, antigen binding sites, and co-factor binding sites.

As the identification and classification of novel genes and their corresponding genes is of particular relevance in ongoing efforts to sequence the genomes of various organisms, this instant invention has significant scientific and commercial utility. At present, more than 180 different enzymatic activities have been classified, and are listed by enzyme name in the following table. The particular classification of an enzyme listed in the following table is defined in accordance with the enzyme classification system described in *Enzyme Nomenclature,* NC-IUBMB, Academic Press, New York, N.Y. (1992).

| E.C. Number | Enzyme Name |
| --- | --- |
| 1.1.1.2 | Alcohol dehydrogenase (NADP+) |
| 1.1.1.21 | Aldehyde reductase |
| 1.1.1.27 | L-lactate dehydrogenase |
| 1.1.1.28 | D-lactate dehydrogenase |
| 1.1.1.29 | Glycerate dehydrogenase |
| 1.1.1.34 | HMG-CoA reductase |
| 1.1.1.42 | Isocitrate dehydrogenase (NADP+) |
| 1.1.1.49 | Glucose-6-phosphate 1-dehydrogenase |
| 1.1.1.50 | 3-alpha-hydroxysteroid dehydrogenase (B-specific) |
| 1.1.1.53 | 3-alpha(or 20-beta) -hydroxysteroid dehydrogenase |
| 1.1.1.62 | Estradiol 17 beta-dehydrogenase |
| 1.1.1.95 | Phosphoglycerate dehydrogenase |
| 1.1.1.159 | 7-alpha-hydroxysteroid dehydrogenase |
| 1.1.1.184 | Carbonyl reductase (NADPH) |

-continued

| E.C. Number | Enzyme Name |
| --- | --- |
| 1.1.1.206 | Tropine dehydrogenase |
| 1.1.1.236 | Tropinone reductase |
| 1.1.1.252 | Tetrahydroxynaphthalene reductase |
| 1.1.3.7 | Aryl-alcohol oxidase |
| 1.1.3.15 | (S)-2-hydroxy-acid oxidase |
| 1.1.99.8 | Alcohol dehydrogenase (acceptor) |
| 1.2.1.2 | Formate dehydrogenase |
| 1.2.1.5 | Aldehyde dehydrogenase (NAD(P)+) |
| 1.2.1.8 | Betaine-aldehyde dehydrogenase |
| 1.2.1.12 | Glyceraldehyde 3-phosphate dehydrogegnase (phosphorylating) |
| 1.2.3.3 | Pyruvate oxidase |
| 1.3.99.2 | Butyryl-CoA dehydrogenase |
| 1.4.1.2 | Glutamate deydrogeanse |
| 1.4.1.3 | Glutamate dehydrogenase (NAD(P)+) |
| 1.4.3.3 | D-amino acid oxidase |
| 1.4.3.6 | Amine oxidase (copper-containing) |
| 1.5.1.3 | Dihydrofolate reductase |
| 1.6.4.2 | Glutathione reductase (NADPH) |
| 1.6.4.8 | Trypanothione reductase |
| 1.6.99.7 | Dihydropteridine reductase |
| 1.8.1.4 | Dihydrolipoamide dehydrogenase |
| 1.11.1.1 | NADH peroxidase |
| 1.11.1.6 | Catalase |
| 1.11.1.7 | Peroxidase |
| 1.11.1.10 | Chloride peroxidase |
| 1.11.1.11 | L-ascorbate peroxidase |
| 1.14.14.1 | Aromatase |
| 1.14.99.7 | Squalene epoxidase |
| 2.1.1.45 | Thymidylate synthase |
| 2.1.1.60 | Calmodulin |
| 2.1.1.63 | Methylated-DNA--[protein]-cysteine S-methyltransferase |
| 2.1.1.73 | Site-specific DNA-methyltransferase (cytosine-specific) |
| 2.1.2.2 | Phosphorbosylglycinamide formyltransferase |
| 2.1.3.3 | Ornithine carbamoyltransferase |
| 2.2.1.1 | Transketolase |
| 2.3.1.12 | Dihydrolipoamide S-acetyltransferase |
| 2.3.1.28 | Chloramphenicol O-acetyltransferase |
| 2.3.1.39 | [Acyl-carrier protein] S-malonyltransferase |
| 2.3.1.41 | 3-oxoacyl-[acyl-carrier protein] synthase |
| 2.3.1.61 | Dihydrolipoamide S-succinyltransferase |
| 2.3.2.13 | Protein-glutamine gamma-glutamyltransferase |
| 2.4.1.1 | Phosphorylase |
| 2.4.2.10 | Orotate phosphoribosyltransferase |
| *2.4.2.14 | Amidophosphoribosyltransferase |
| 2.4.2.29 | Queuine tRNA-ribosyltransferase |
| 2.4.2.30 | NAD(+) ADP-ribosyltransferase |
| 2.5.1.1 | Dimethylallyltransferase |
| 2.5.1.7 | UDP-N-acetylglucosamine 1-carboxyvinyltransferase |
| 2.5.1.10 | Geranyltranstransferase |
| 2.5.1.18 | Glutathione transferase |
| *2.6.1.1 | Aspartate aminotransferase |
| *2.6.1.16 | Glucosamine--fructose-6-phosphate aminotransferase (isomerizin) |
| 2.7.1.11 | 6-phosphofructokinase |
| 2.7.1.21 | Thymidine kinase |
| 2.7.1.30 | Glycerol kinase |
| 2.7.1.37 | Protein kinase |
| 2.7.1.38 | Phosphorylase kinase |
| 2.7.1.40 | Pyruvate kinase |
| 2.7.1.69 | Protein-N(PI)-phosphohistidine-sugar phosphotransferase |
| 2.7.1.105 | 6-phosphofructo-2-kinase |
| 2.7.1.112 | Protein-tyrosine kinase |
| 2.7.1.117 | [Myosin light-chain] kinase |
| 2.7.1.123 | Calcium/calmodulin-dependent protein kinase |
| 2.7.2.3 | Phosphoglycerate kinase |
| 2.7.3.3 | Arginine kinase |
| 2.7.4.6 | Nucleoside-diphosphate kinase |
| 2.7.4.8 | Guanylate kinase |
| 2.7.7.6 | DNA-directed RNA polymerase |
| 2.7.7.7 | DNA-directed DNA polymerase |
| 2.7.7.10 | UTP--heoxe-1-phosphate uridylytransferase |
| 2.7.7.48 | RNA-directed RNA polymerase |
| 2.7.7.49 | RNA-directed DNA polymerase |

-continued

| E.C. Number | Enzyme Name |
|---|---|
| 2.7.7.50 | mRNA guanylyltransferase |
| 2.8.1.1 | Thiosulfate sulfurtransferase |
| 2.8.3.12 | Glutaconate CoA-transferase |
| 3.1.1.1 | Carboxylesterase |
| 3.1.1.3 | Triacylglycerol lipase |
| 3.1.1.4 | Phospholipase A2 |
| 3.1.1.45 | Carboxymethylenebutenolidase |
| 3.1.1.47 | 2-acetyl-1-alkylglycerophosphocholine esterase |
| 3.1.3.2 | Acid phosphatase |
| 3.1.3.11 | Fructose-bisphosphatase |
| 3.1.3.16 | Serine/threonine specific protein phosphatase |
| 3.1.3.46 | Fructose-2,6-bisphosphate 2-phosphatase |
| *3.1.3.48 | Protein-tyrosine-phosphatase |
| 3.1.4.11 | 1-phosphatidylinositol-4,5-bisphosphate phosphodiesterase |
| 3.1.11.2 | Exodeoxyribonuclease III |
| 3.1.21.4 | Type II site-specific deoxyribonuclease |
| 3.1.25.1 | Deoxyribonuclease (pyrimidine dimer) |
| 3.1.26.4 | Ribonuclease H |
| 3.1.27.3 | Ribonuclease T1 |
| 3.1.27.4 | Ribonuclease U2 |
| 3.2.1.1 | Alpha-amylase |
| 3.2.1.2 | Beta-amylase |
| 3.2.1.4 | Cellulase |
| 3.2.1.8 | Endo-1,4-beta-xylanase |
| 3.2.1.14 | Chitinase |
| 3.2.1.17 | Lysozyme |
| 3.2.1.18 | Exo-alpha-sialidase |
| 3.2.1.21 | Beta-glucosidase |
| 3.2.1.23 | Beta-galactosidase |
| 3.2.1.85 | 6-phospho-beta-galactosidase |
| 3.2.1.122 | Alpha glucosidase |
| 3.2.2.1 | Purine nucleosidase |
| 3.2.2.22 | rRNA N-glycosidase |
| 3.4.11.1 | Leucyl aminopeptidase |
| 3.4.11.5 | Prolyl aminopeptidase |
| 3.4.13.19 | Dehydropeptidase I |
| 3.4.16.6 | Carboxypeptidase D |
| 3.4.17.2 | Carboxypeptidase B |
| 3.4.19.3 | Pyroglutamyl-peptidase I |
| 3.4.21.1 | Chymotrypsin |
| 3.4.21.4 | Trypsin |
| 3.4.21.5 | Thrombin |
| 3.4.21.32 | Brachyurin |
| 3.4.21.35 | Tissue kallikrein |
| 3.4.21.62 | Subtilisin |
| 3.4.21.66 | Thermitase |
| 3.4.21.81 | Streptogrisin B |
| 3.4.21.82 | Glutamyl endopeptidase II |
| 3.4.21.88 | Repressor lexA |
| 3.4.22.2 | Papain |
| 3.4.22.28 | Picornain 3C |
| 3.4.23.16 | Retropepsin |
| 3.4.23.20 | Penicillopepsin |
| 3.4.24.27 | Thermolysin |
| 3.4.24.46 | Adamalysin |
| 3.5.1.1 | Asparaginase |
| 3.5.1.5 | Urease |
| 3.5.1.31 | Formylmethionine deformylase |
| 3.5.1.38 | Glutaminase-(asparagin-)ase |
| 3.5.1.59 | N-carbamoylsarcosine amidase |
| 3.5.3.3 | Creatinase |
| 3.5.4.4 | Adenosine deaminase |
| 3.6.1.1 | Inorganic pyrophosphatase |
| 3.6.1.7 | Acylphosphatase |
| 3.6.1.23 | dUTP pyrophosphatase |
| 3.6.1.34 | H(+)-transporting ATP synthase |
| 3.6.1.36 | H/K ATPase |
| 3.6.1.38 | Ca ATPase |
| 3.8.1.5 | Haloalkane dehalogenase |
| 4.1.1.1 | Pyruvate decarboxylase |
| 4.1.1.7 | Benzoylformate decarboxylase |
| 4.1.1.31 | Phosphoenolpyruvate carboxylase |
| 4.1.2.13 | Fructose-biphosphate aldolase |
| 4.1.2.14 | 2-dehydro-3-deoxyphosphogluconate aldolase |
| 4.1.2.17 | L-fuculose-phosphate aldolase |
| 4.1.3.3 | N-acetylneuraminate lyase |

-continued

| E.C. Number | Enzyme Name |
|---|---|
| 4.1.3.7 | Citrate (si)-synthase |
| 4.2.1.1 | Carbonate dehydratase |
| 4.2.1.2 | Fumarate hydratase |
| 4.2.1.11 | Phosphopyruvate hydratase |
| 4.2.1.24 | Porphobilinogen synthase |
| 4.2.1.39 | Gluconate dehydratase |
| 4.2.1.51 | Prephenate dehydratase |
| 4.2.1.52 | Dihydrodipicolinate synthase |
| 4.2.1.60 | 3-hydroxydecanoyl-[acyl-carrier protein] dehydratase |
| 4.2.99.13 | DNA-(apurinic or apyrimidinic site) lyase |
| 4.3.2.1 | Argininosuccinate lyase |
| 4.6.1.2 | Guanylate cyclase |
| 5.1.1.7 | Diaminopimelate epimerase |
| 5.1.2.2 | Mandelate racemase |
| 5.3.1.1 | Triosephosphate isomerase |
| 5.3.1.5 | Xylose isomerase |
| 5.3.1.10 | Glucosamine-6-phosphate isomerase |
| 5.3.3.1 | Steroid delta-isomerase |
| 5.3.3.10 | 5-carboxymethyl-2-hydroxymuconate delta-isomerase |
| 5.3.99.3 | prostaglandin endoperoxide synthase |
| 5.4.2.1 | Phosphoglycerate mutase |
| 5.4.2.2 | Phosphoglucomutase |
| 5.4.99.5 | Chorismate mutase |
| 5.5.1.1 | Muconate cycloisomerase |
| 5.99.1.2 | DNA topoisomerase |
| 5.99.1.3 | DNA topoisomerase (ATP-hydrolysing) |
| 6.2.1.5 | Succinate--CoA ligase (ADP-forming) |
| 6.3.4.4 | Adenylosuccinate synthase |
| 6.3.4.14 | Biotin carboxylase |
| 6.3.5.2 | GMP synthase (glutamine-hydrolysing) |
| 6.3.5.5 | Carbamoyl-phosphate synthase (glutamine-hydrolysing) |
| 6.4.1.2 | Acetyl-CoA carboxylase |

As will be appreciated by those in the art, the instant invention embodies functional site descriptors prepared for the enzymatic activities of the enzyme classes listed above, as well as for other protein activities and functions, whether now known or later discovered.

Structural Determination

Protein structures can be determined by a variety of experimental or computational methods, several of which are described below.

A. Experimental Analyses of Biomolecule Structure

Protein structure can be assessed experimentally by any method capable of producing at least low resolution structures. Such methods currently include x-ray crystallography and nuclear magnetic resonance (NMR) spectroscopy. Structures elucidated by these methods are of varying quality. For the production of functional descriptors according to the invention described herein, high resolution or high quality structures are desirable. Such high quality structures are can also easily be probed for functional sites using the functional descriptors described herein. However, the inventors have discovered that functional site descriptors can also be applied to predict the function in lower quality structures elucidated experimentally, such as low-resolution x-ray crystal structures, in addition to models produced purely by computational methods.

(i) X-ray crystallography

X-ray crystallography is one method for protein structural evaluation, and is based on the diffraction of X-ray radiation of a characteristic wavelength by electron clouds surrounding the atomic nuclei in the crystal. X-ray crystallography uses crystals of purified biomolecules (but these frequently include solvent components, co-factors, substrates, or other ligands) to determine near atomic resolution of the atoms making up the particular biomolecule. Techniques for crystal growth are known in the art, and typically vary from biomolecule to biomolecule. Automated crystal growth techniques are also known.

Small molecules, i.e., those having a molecular weight of less than about 2,000 daltons (D), typically crystallize with fewer than several (frequently two) solvent components, with the atoms of the small molecule occupying a large majority, even greater than 90%, of the crystal volume. However, proteins are typically much larger (typically having molecular weights of 30,000–200,000 D), and when packaged into crystal lattice points, leave much larger gaps for inclusion of other molecules in the crystal. Thus, protein crystals typically contain 40–60% solvent. As a result, protein crystals have dynamic flexibility that can cause disorder in X-ray diffraction studies and allow an observed electron density to be matched by more than local conformation. Dynamic disorder can be reduced or eliminated by lowering the environmental temperature of the crystal during X-ray bombardment. Remaining static disorder is due to one or more rigid static molecular conformations.

Detection of diffracted radiation enables the use of mathematical equations (e.g., Fourier synthesis) to generate three-dimensional electron density maps of the diffracted biomolecule. Multiple diffractions are required to make such determinations, with the number of reflections correlating positively with the resolution desired. Low numbers of reflections typically do not provide the requisite information to determine atomic positioning, although the position of a polypeptide chain in individual protein molecules can often be fitted to the electron density map. Structures resulting from these types of crystallographic data are often termed low resolution structures. The fitting of a protein's amino acid sequence (for example, the primary structure of a protein solved by deducing the amino acid sequence encoded by a nucleic acid (e.g., a cDNA sequence) encoding the protein) to the determined electron density patterns allows the protein's structure to be refined. Larger numbers of reflections and/or increasing refinement produces a higher resolution protein structure.

It is important to note that while techniques such as X-ray diffraction provide substantial information about protein structure, to date they provide only limited information about mechanisms of action. For X-ray crystallography, this is due to the fact that the devined structures depict time-averaged atomic coordinates of atoms, and atoms which undergo rapid dynamic fluctuation in solution. Indeed, on average the atoms in a protein are believed to oscillate over 0.7 Å per picosecond. To date, approximately 2,000 non-redundant protein crystal structures have been solved.

ii. Nuclear magnetic resonance (NMR) spectroscopy

Nuclear magnetic resonance (NMR) currently enables determination of the solution conformation (rather than crystal structure) of biomolecules. Typically only small molecules, for example proteins of less that about 100–150 amino acids, are amenable to these techniques. However, recent advances have lead to the experimental elucidation of the solution structures of larger proteins, using such techniques as isotopic labeling. The advantage of NMR spectroscopy over x-ray crystallography is that the structure is determined in solution, rather than in a crystal lattice, where lattice neighbor interactions can alter the protein structure. The disadvantage of NMR spectroscopy is that the NMR structure is not as detailed or as accurate as a crystal structure. Generally, biomolecule structures determined by NMR spectroscopy are of moderate resolution compared relative to those determined by crystallography.

NMR uses radio frequency radiation to examine the environment of magnetic atomic nuclei in a homogeneous magnetic field pulsed with a specific radio frequency. These pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space.

Protein structures can be determined by performing a number of two- (and sometimes 3- or 4-) dimensional NMR experiments and using the resulting information as constraints in a series of protein folding simulations. See Protein NMR Spectroscopy, Principles and Practice, J. Cavanagh, et al., Academic Press, San Diego, 1996, for a discussion of the many techniques associated with NMR spectroscopy.

Other Spectroscopic Techniques

Other techniques useful in studying biomolecule structure include circular dichroism (CD), fluorescence, and ultraviolet-visible absorbance spectroscopy. See Physical Biochemistry: Applications to Biochemistry and Molecular Biology, $2^{nd}$ ed., W.H. Freeman & Co., New York, N.Y., 1982 for descriptions of these techniques. Such methods currently do not provide atomic level structural detail about biomolecules.

As described herein, experimentally solved biomolecule structures, particularly those solved to high resolution, are used to generate and validate functional site descriptors produced in accordance with the instant methods. As the number of experimentally solved structures increases over time, new functional site descriptors can be created. In addition, functional site descriptors produced in accordance with the invention prior to the solution of such structures can be modified, if necessary. Therefore, certain embodiments of the invention concern the periodic validation, potential modification, and novel creation of one or more of functional site descriptors. These updates are performed through comparison to newly described biomolecules having specified biological function(s), for which three dimensional structures have been elucidated, preferably experimentally (as opposed to prediction) to high resolution.

B. Methods for Producing Predicted Models of Biomolecule Structure

While production of functional site descriptors preferably involves comparisons of a putative descriptor to one or more experimentally solved structures, the inventors have discovered that such descriptors can be used to identify the function(s) of a protein, for example, an enzymatic protein, using, in some embodiments, a predicted three-dimensional model thereof. Indeed, inexact models produced by a prediction algorithm (representative examples of which are described in greater detail below, or which are later developed) can be used as the structures against which functional site descriptors according to the invention are probed. Of course, exact models and experimentally solved structures (particularly high and medium resolution structures) can also be used for such purposes.

i. Homology Modeling Techniques

Some methods for predicting structures of proteins involve homology modeling. Homology modeling is applied to amino acid sequences that are evolutionarily related, i.e., they are homologous, such that their residue sequences can be aligned with some confidence. In one example of this method, the sequence of a protein whose structure has not been experimentally determined is aligned to the sequence of a protein whose structure is known using one of the standard sequence alignment algorithms (Altschul, et al. (1990), *J. Mol. Biol., vol.* 215:403–410; Needleman and Wunsch (1970), *J. Mol. Biol., vol.* 48:443–453; Pearson and Lipman (1988), *Proc. Natl. Acad. Sci. USA, vol.* 85:2444–2448). Homology modeling algorithms, for example, Homology (Molecular Simulations, Inc.), build the sequence of the protein whose structure is not known onto the structure of the known protein. The result is a predicted model for the sequence whose structure has not been experimentally determined. Such a predicted structure is termed a "homology model".

ii. Threading Algorithms

In an inverse folding approach to protein structure prediction, one "threads" a probe amino acid sequence through different template structures and attempts to find the most compatible structure for a given sequence. In certain embodiments, sequence-to-structure alignments are performed by a "local-global" version of the Smith-Waterman dynamic programming algorithm (Waterman, 1995). In such embodiments, alignments are ranked by one or more, preferably three, different scoring methods. In a three method approach (Jaroszewski et al., 1997), the first scoring method can be based on a sequence-sequence type of scoring. In this sequence-based method, the Gonnet mutation matrix can be used to optimize gap penalties, as described by Vogt and Argos (Vogt et al., 1995). The second method can use a sequence-structure scoring method based on the pseudo-energy from the probe sequence "mounted" in the structural environment in the template structure. The pseudo-energy term reflects the statistical propensity of successive amino acid pairs (from the probe sequence) to be found in particular secondary structures within the template structure. The third scoring method can concern structure-structure comparisons, whereby information from the known template structure(s) is(are) compared to the predicted secondary structure of the probe sequence. A particularly preferred secondary structure prediction scheme uses a nearest neighbor algorithm.

After computing scores for the sequence-to-structure alignments, the statistical significance of the each score is preferably determined by fitting the distribution of scores to an extreme value distribution, and the raw score is compared to the chance of obtaining the same score when comparing two unrelated sequences (Jaroszewski et al., 1997).

Once the alignment of the probe sequence-to-template structure has been determined, a three-dimensional model is built. A representative example of automated modeling tools include Modeller4 (Tripos Associates, St. Louis). Such tools preferably produce all non-hydrogen atom coordinate files for the three-dimensional model built from the sequence-to-structure alignment provided by the threading algorithm.

The final predicted structure is only as good as the sequence alignment produced by the threading algorithm, and local misalignments may occur in threading predictions and sequence alignments. The problem can be overcome in at least some cases by allowing for small errors in the alignments and by using not just the threading prediction with the highest score (i.e., the optimum alignment), but a number of top ranking, alternative threading-based structure predictions for the same sequence. Use of the conservation profile analysis further increases confidence in threading-based structure predictions by seeking consistency in the sequence alignments; thereby reducing the chances of accidental matches.

When a threading algorithm is used in the practice of this invention, typically the sequence of a protein whose function is being evaluated is "threaded" through a large database of proteins whose structures have been experimentally elucidated by, for example, x-ray crystallography or NMR spectroscopy. A number of sequence-to-structure alignments are produced for each sequence. Each of these alignments is scanned for the occurrence and conservation of the known functional site residues identified for the functional descriptor (see FIG. 8). If the functional site residues are conserved, a three dimensional structural model is produced from the sequence-to-structure alignment using a modeling tool, such as Modeller4 (Tripos Associates, St. Louis). The functional descriptor is then used to probe each model to determine the presence or absence of the functional site.

iii. Ab Initio Structure Modeling

Another computational approach to protein structure elucidation involves ab initio prediction. Such procedures generally have two parts: 1) parameter derivation using information extracted from multiple sequence alignment; and 2) structure assembly (or "folding") and refinement. As those in the art will appreciate, any conventional or later-developed ab initio biomolecule structure prediction algorithm can be used in connection with this aspect of the invention.

In certain preferred embodiments of the invention, the "MONSSTER" (Modeling Of New Structures from Secondary and Tertiary Restraints) ab initio folding algorithm is used to produce inexact models of protein structures. The MONSSTER algorithm uses a high coordination lattice-based α-carbon representation for the folding of proteins (Skolnick et al., 1997) and is modified to incorporate the expected accuracy and precision of the predicted tertiary structures (Ortiz et al., 1997). Parameters for ab initio folding, including predicted secondary and tertiary structure information, is extracted from multiple sequence alignment analysis.

When using the MONSSTER ab initio structure prediction algorithm in the practice of this invention, a number of independent simulated annealing simulations from a fully extended initial conformation should be carried out (assembly runs) for each biomolecule, particularly when the biomolecule is a protein. Structures generated by these assembly runs are then clustered, and an example low energy structure from each cluster is subjected to a low temperature, isothermal refinement. The predicted fold preferably is that of lowest average energy, although in some embodiments, several of the next lowest energy structures are also examined.

In certain preferred embodiments of the invention, inexact protein structure models generated by ab initio prediction methods can be utilized for functional analysis using functional site descriptors. Preferably, functional site descriptors are tested and validated on a series of correctly and incorrectly folded structures produced during the assembly and isothermal runs for various proteins.

Other Uses of Predicted Models in the Instant Invention

As those in the art will appreciate, functional site descriptors can also be used for purposes other than predicting biomolecule function. For example, functional site descriptors can be used to validate or confirm the accuracy of biomolecule structures predicted using the methods described herein or other structure prediction methods. For example, if a biomolecule is predicted to have a particular structure, successful application of one or more functional site descriptors thereto to identify one or more functional sites in the biomolecule validates the predicted fold. Such validation can be further confirmed by experimental demonstration of the particular biological function by the biomolecule. Alternatively, further confirmation of a correct structure prediction by such methods can be derived by the functional site descriptor-mediated identification of two or more functional sites (for example, the substrate binding site and a cofactor binding site) on a biomolecule.

Computer-Implemented Embodiments of the Invention

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the present invention described elsewhere in this document. Various computer-based systems, methods and implementations in accordance with the above-described technology are now presented.

As introduced above, the inventors have introduced the concept of a functional site descriptor to help identify molecular functions, as well as techniques for creating functional site descriptors for various functional sites of known molecules, or of known molecular functions. The inventors have further conceived and reduced to practice techniques for utilizing one or more known functional site descriptors to predict functions in a given molecular model.

Figure 2:
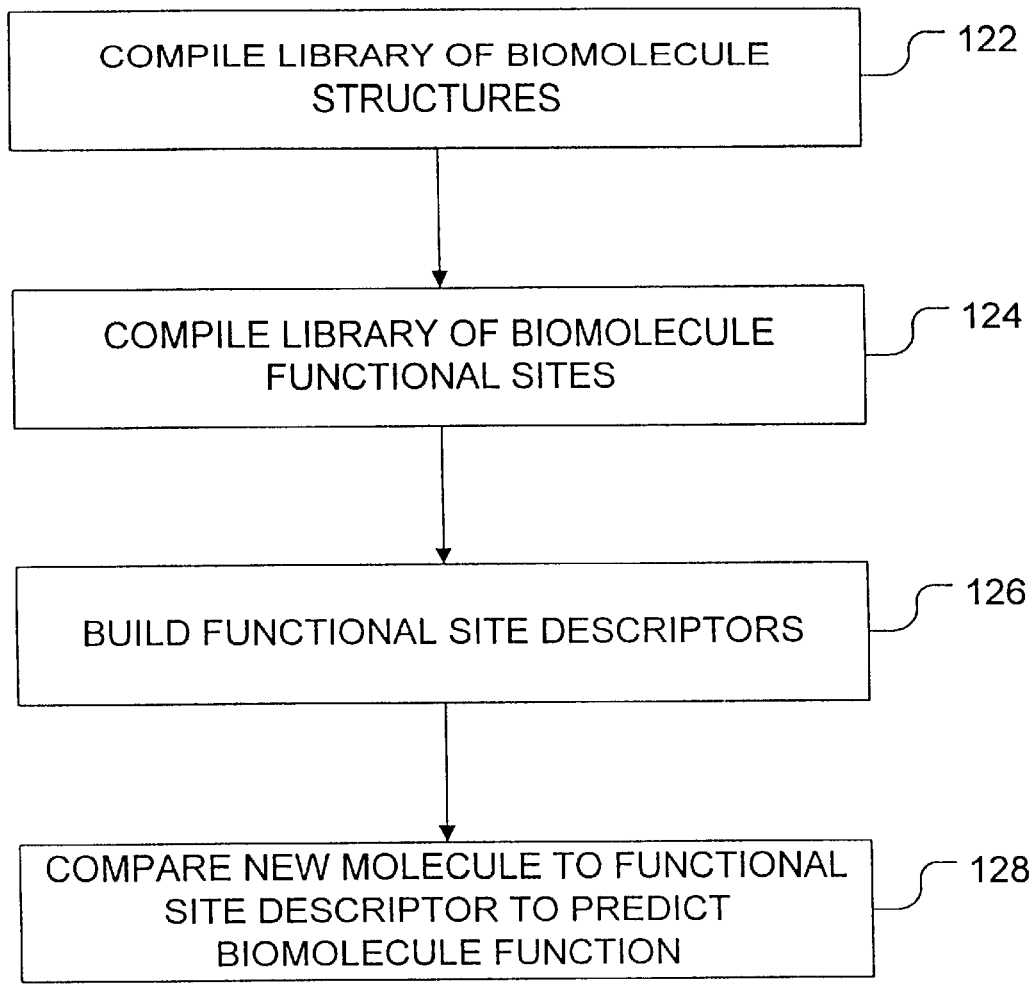
FIG. 2 is an operational flow diagram generally illustrating a process for preparing a functional site descriptor for a given molecular function, and using the functional site descriptor to determine whether a given molecular model should exhibit the functional properties associated with the functional site descriptor according to one embodiment of the invention.

FIG. 2 is an operational flow diagram generally illustrating a process for creating a functional site descriptor for a given molecular function, and using the functional site descriptor to determine whether a given molecular model should exhibit the functional properties associated with the functional site descriptor according to one embodiment of the invention. Referring now to FIG. 2, in step 122, a library of known molecular structures is compiled. To a certain extent, there are libraries already in existence and available to many scientists in which known molecular structures for proteins and other biomolecules are catalogued. In accordance with one aspect of the invention, such known and existing libraries can be utilized. These libraries can be further augmented or supplemented as additional molecular structures are identified and characterized. The embodiment described in the context of FIG. 2 concerns a biomolecule that is a protein, particularly an enzyme the catalytic activity of which (at least with regard to the representative biomolecular function herein described) is defined by a known active site.

In step 124, a protein structure library is utilized to build a library of known functional sites. These functional sites (referred to as active sites in the instant case) are comprised of a group of two or more residues in a molecular structure (e.g., folded protein in the case of proteins) that are known to perform or correlate with a given function or activity for that biomolecule (here, a protein). Thus, as a result of step 124, a library or database of known active sites (or other functional sites) and their descriptions can be created and maintained. Such descriptions preferably concern the geometric, or three-dimensional, relationships between two or more elements of these functional sites. In particularly preferred embodiments, such relationships are expressed as interatomic distance ranges, and may or may not include information regarding bond angles (or bond angle ranges), between adjacent atoms. In addition, such descriptions include the identity of the atom, or molecule, at a particular location. For example, representations of amino acid residues used to describe a functional site descriptor for a particular catalytic function will include the identity of the residue at the particular position. As those in the art will appreciate in certain embodiments, the identity of the residue of a particular position in the active site (or other functional site) may not be universally conserved across all members of the particular enzyme (or other biomolecule) class. Thus, in such cases it is preferred that the identity parameter be relaxed and include residues known to reside at that position. In addition, as those in the art will appreciate, the representation of a particular amino acid residue (in cases where the biomolecule is a protein) can be accomplished in different ways. For example, the α-carbon of the residues selected as comprising the active site descriptor may be used. Alternatively, or in addition, the mean center of mass of the side chain of the particular residues may be selected. Of course, other representations or combinations of elements can also be used, and are left to the discretion of the artisan.

In step 126, a group of one or more active sites from the known active site database or library are used to construct a functional site descriptor. The functional site descriptor in one embodiment is a somewhat generalized model or description of the active sites or functional sites associated with a particular molecular function. Preferably, in one embodiment, the functional site descriptor is general enough to describe or to help identify functional sites having a given function in numerous different and alternative molecules, without being so broad or generic as to identify functional sites having different functions. The manner in which functional site descriptors can be created according to one or more embodiments are described in detail below. Furthermore, it is preferable that functional site descriptors can be created for numerous molecular functions.

In step 128, a molecular structure of a new molecule (or a known molecule having one or more functions that are not known) is compared to one or more functional site descriptors to predict the function of the molecule. In one embodiment, the functional site descriptor is broad enough to generally identify the function in all potential manifestations the functional site can have for various molecular structures. On the other hand, it is preferred that the functional site descriptor is not so broad as to encompass alternative functions. With these constraints, a positive comparison between the functional site descriptor and a site in the molecular structure indicate that the molecule under study exhibits the biological function associated with the functional site descriptor. As such, the functional site descriptor can be used to identify a given function in a molecular structure. Techniques for using a functional site descriptor to predict a biological function in a biomolecule, particularly those whose structure is known by molecular modeling, are also described in detail below.

Figure 3:
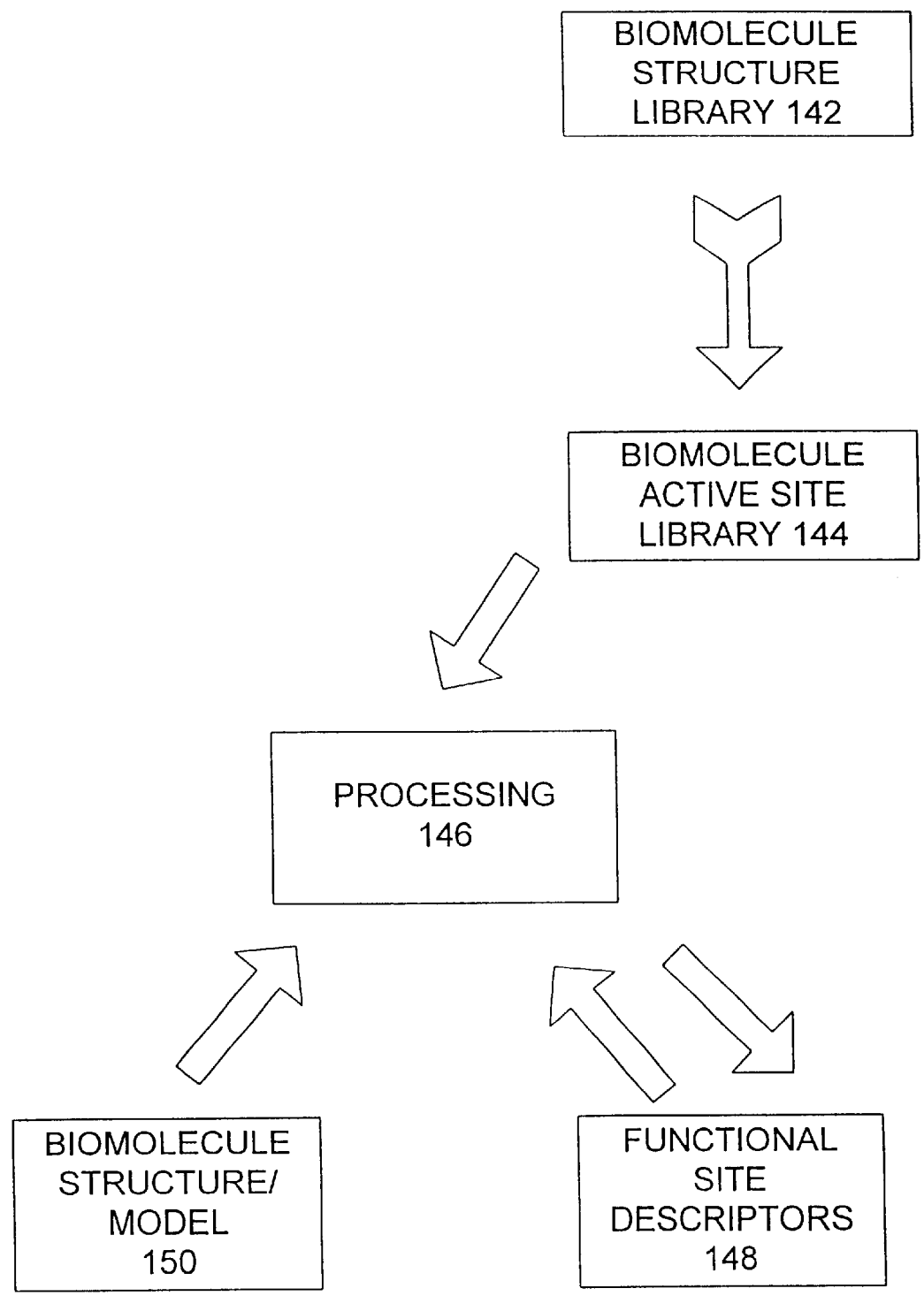
FIG. 3 is a functional block diagram generally illustrating functionality that can be associated with the various processes and techniques for generating functional site descriptors and using functional site descriptors to predict molecular function according to one embodiment of the invention.

FIG. 3 is a functional block diagram generally illustrating functionality that can be associated with the various processes and techniques for generating functional site descriptors and using functional site descriptors to predict molecular function according to various embodiments of the invention. Generally speaking, FIG. 3 is a functional block diagram intended only to exemplify functionality of one or more embodiments described herein. FIG. 3 is not intended to, and should not be construed as, implying a particular physical, logical, or structural architecture for implementing a computer-based system to carry out the functionality described herein. In fact, it will be apparent to one of ordinary skill in the art after reading this detailed description how to implement the various features and aspects of the invention using various alternative architectures, including alternative combinations and configurations of computer software and hardware.

Referring now to FIG. 3, the process begins with a collection or library of known molecular structures as indicated by block 142. As stated, these known structures can come from generally available scientific libraries cataloging known molecular structures and/or from the scientific literature. The library will contain at least one known structure. Preferably the library will contain two or more (e.g. 3, 4, 5, 6, 7, 8, 9) structures known to possess or be responsible for the particular biological function to be described or represented by the particular functional site descriptor. It will also be appreciated that more than one functional site descriptor can be developed in accordance herewith with respect to a particular biological function.

From the library of known structures 142, a subset of known functional sites 144 (here, for purposes of illustration only, active sites) can be determined. As stated with regard to catalytic activities of enzymes, the known functional sites are a collection of two or more amino acid residues that define the particular activity. Of course, other atoms and molecules can be used to describe other types of functional sites. In addition, there may be more than one functional site for a given molecular structure, and there is preferably more than one function accounted for in the known data set 144. Preferably, known data set 144 is a computer-based data set wherein the information is stored electronically and accessible by a computing system. In some embodiments, as illustrated in more detail below, the data describing the functional sites is a three-dimensional data representation indicating the residues that make up the active site and a spatial relationship between those residues. Specifics regarding how the data are stored and compiled are somewhat secondary, as will be readily understood by one of ordinary skill in the art after reading this description.

Processing system 146 utilizes the data representations of the functional site(s) to create one or more functional site descriptors 148. Preferably, one functional site descriptor is provided for each function associated with a group of functional sites. Processing system 146 can be implemented, for example, as a general purpose processing system. After reading this description, and the further description of the functionality performed by this processing system, one of ordinary skill in the art will understand how to specify and implement a processing system to carry out the described functionality. In one embodiment, processing system 146 is implemented as a Pentium®-based processing system with the appropriate user interfaces and peripheral devices.

To predict the functionality of a given molecular structure, the processor-based system 146 compares one or more functional site descriptors 148 with the subject molecular structure 150 to determine if there is a match. If there is a match, this provides an indication that the subject molecular structure 150 has the biological function identified as being associated with the matching functional site descriptor 148. In preferred embodiments of such automated implementation of one or more functional site descriptors, the computer-band system will identify which biological function(s) is(are) possessed by the biomolecule(s) under study. The particular output of such results can be implemented in any fashion desired by the user.

Having thus generally described creating and using one or more functional site descriptors to predict molecular function, the details of generating functional site descriptors and using functional site descriptors to predict molecular function is now described in greater detail according to one embodiment of the invention. FIG. 4 is an operational flow diagram illustrating a process for building a functional site descriptor for a given function according to one embodiment of the invention. Referring now to FIG. 4, in step 212, a group of preferably two or more functional sites are selected from a library of known functional sites 144. Preferably, all of the functional sites selected are those functional sites that are known to be associated with a particular biological function of interest.

In step 214, the geometries of the selected functional sites are determined. That is, as further described in detail below, in some embodiments the atoms or molecules (e.g., amino acid residues in the case of proteins, particularly with regard to active sites) associated with the selected functional site and the spatial orientation of the residues relative to one another is determined. In one embodiment, this determination can be made in advance and stored in a database, such as a database of known functional sites 144. Thus, as a result of steps 212 and 214, data representations of selected functional sites are available for use by a processing system in creating a functional site descriptor.

In step 216, one or more geometric parameters of the selected functional sites is modified, or "relaxed." More specifically, in certain preferred embodiments, a delta, or range of possible geometries (for example, distances between the a-carbon atoms of amino acid residues), is applied to a parameter of one or more selected functional site geometries. In step 218, the modified functional site geometry is compared to the a functional site geometry data set to determine whether this broadened, or relaxed, geometry still compares favorably with the data set of known geometries in its ability to specifically identify biomolecules having the desired biological function.

If the comparison is favorable, one or more geometric parameters can be further modified or broadened until it is broadened so much that the comparison is no longer favorable because biomolecules known not to possess the particular biological function are identified as having the function. This process is illustrated by step 374 and the flow line from step 374 to step 216. Further details regarding an example decision making process for determining when the appropriate level of broadening or relaxation is described below.

FIG. 5 is an operational flow diagram illustrating a method for creating a functional site descriptor according to one embodiment of the invention. Referring now to FIG. 5, in step 262, a group of preferably two or more functional site geometries is selected from the known library of functional sites.

In preferred embodiments, the functional site geometries are described by N residues and the group of geometries is selected from among structures that are known to have the desired function. In particular embodiments with respect to enzyme active sites, three residues are preferably utilized; however, after reading this description it will become apparent to one of ordinary skill in the art how different numbers of residues can be utilized depending on the goals of the system implementation.

Figure 6A:
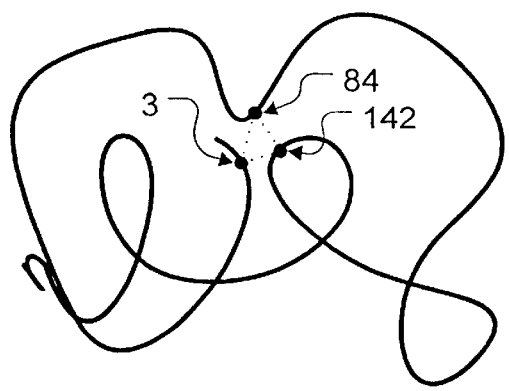
FIGS. 6A, 6B, and 6C, illustrates residues of a hypothetical active site descriptor (designated by numbers 3, 84, 142 as shown in FIG. 6A), adjacent residues (designated by numbers 2 and 4 for the residue designated as 3, 83 and 85 as shown in FIG. 6B for the residue designated as 84, and 141 and 143 for the residue designated as 142), and geometries (here, distance ranges, indicated by dotted and hatched lines) among the residues according to one embodiment of the invention.
Figure 6B:
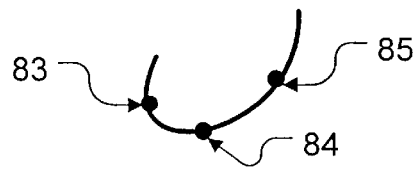
Figure 6C:
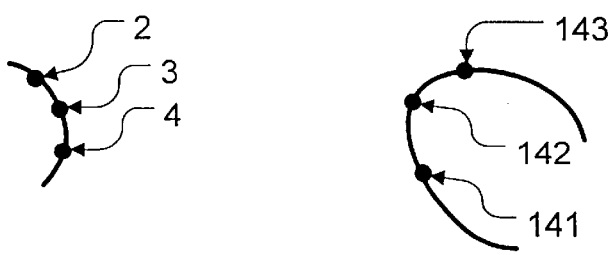
Figure 6C:
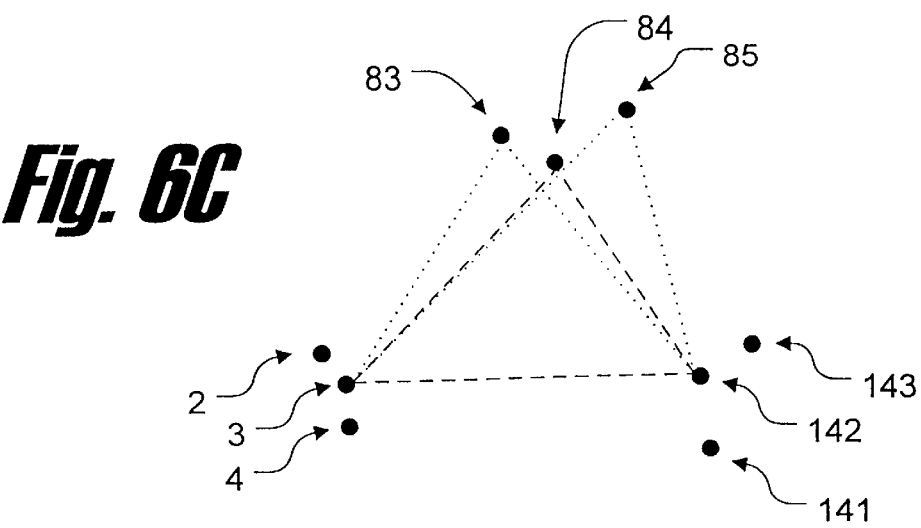

FIG. 6, which comprises FIGS. 6A, 6B, and 6C, is a diagram illustrating residues of a hypothetical enzyme active site descriptor, adjacent residues, and geometries among the residues according to preferred embodiments of the invention. Referring now to FIG. 6A, the active site descriptor is illustrated as being comprised of three residues identified for purposes of illustration only as 3, 84, and 142, which numbers correspond to amino acid position in the hypothetical protein depicted in this figure. Amino acid identity at each of those positions has not been provided in this example. For discussion purposes, residue 84 is identified as being the primary residue.

Returning now to FIG. 5, in step 264, the primary, secondary, tertiary, . . . n-ary residues are defined and identified. That is, each of the N residues that make up the functional site descriptor are identified as being primary, secondary, and so on. The selection of which residue is identified as primary can be made somewhat arbitrarily; however, it is preferred that a residue of importance is selected as the primary residue. In the biochemical arts, a biochemist can typically predict, for example, a residue that would go through a covalent change during catalysis. If so, it is preferred that this residue be identified as the primary residue. If there is more than one residue that is known or predicted to go through a covalent change during catalysis, either of these residues is preferably selected as the primary residue. Alternatively, two descriptors, each naming a different primary residue (but otherwise comprising the same parameters), can be generated.

In preferred embodiments, additional residues adjacent to the primary, secondary, tertiary, etc. residues that make up the functional site descriptor are selected, as described in step 268. As those in the art will appreciate, an "adjacent" residue refers to a residue that is either x+1 or x−1 in the primary amino acid sequence if the protein, where x is the amino acid position of the primary, secondary, etc. residue, as the case may be.

FIG. 6b illustrates residues that are immediately adjacent to the residues making up the active site descriptor. Specifically, in the example illustrated in FIG. 6B, residue 84 has adjacent residues 83 and 85. Residue 3 has adjacent residues 2 and 4. Similarly, residue 142 has adjacent residues 141 and 143.

Referring again to FIG. 5, in step 270, relative geometries among the residues and the adjacent residues are defined. That is, the spatial relationship between or among the residues is determined and defined. Preferably, the relationship among one or more adjacent residues in relation to other primary, secondary, etc. and/or adjacent residues is also utilized in determining relevant geometries. Where only two or three residues are utilized, and adjacent residues are not utilized, a two-dimensional spatial representation is sufficient from a mathematical perspective. However, as will become more apparent after reading the detailed description below, such a two-dimensional data set may not be sufficient to uniquely define a desired biological function. Thus, the data set used to defined the relevant geometries is a three-dimensional data set sufficient to define a three-dimensional relationship among the various residues comprising the functional site descriptor, and preferably includes at least some spatial information with regard to one or more adjacent residues.

In particularly preferred embodiments of active site descriptors according to the invention, a nine-distance data set that describes nine distances among the various residues and adjacent residues is utilized. FIG. 6C is a diagram illustrating an example of these nine distances for the example residues illustrated in FIG. 6B. After reading this description, it will become apparent to one of ordinary skill in the art how to implement the invention using M-distances, where M ranges from as few as 2 to 15 or more, and ultimately is limited only by the number of parameters in the functional site descriptor between which distances (preferably distance ranges) are desired to be included, for example, to distinguish biomolecules having the desired function from those known not to possess that function.

FIG. 6C illustrates residue pairings for purposes of determining distance geometries between α-carbon atoms of amino acid residues in a hypothetical active site. The residue pairs of this "9-distance" set of geometric constraints depicted are: 84-142, 84-3, 3-142, 83-3, 85-3, 141-84, 143-84 2-84, and 4-84. As will be appreciated, in the particular circumstance, more or fewer geometric constraints can also be utilized. Using this technique, a data set defining the residues of a functional site can be defined with relative specificity. In fact, in many instances, interatomic distances of various biomolecules are known to accuracies on the angstrom level. Having defined a geometric parameter of a functional site descriptor to this level of specificity, this geometry will likely only match the active site of the particular molecule for which it is created. However, as stated above, one goal in creating a functional site descriptor is to create a descriptor that is broad enough to allow it to match or fall within the active sites for the same function for many different molecules. That is, for each molecule that performs a particular function, there is functional site geometry for that function. However, exact duplication of spatial, geometric, and other parameters is not necessarily required for duplicate biological function.

Therefore, in step 272 of FIG. 5, the geometry of a determined active site descriptor is broadened. In one embodiment, one or more geometric or other parameters of a functional site descriptor (e.g., an active site descriptor) is broadened by adding a delta, which, in the hypothetical under discussion, is preferably a plus or minus uncertainty level, or range, in the distances between the residues selected to comprise the functional site descriptor. As a result, this new site descriptor is defined, in part, by a plurality of distances, wherein each distance has associated therewith a level of uncertainty. In step 274, this functional site descriptor having relaxed geometric parameters is compared with one or more functional sites in the data set of known functional sites to determine if the relaxed descriptor accurately identifies all biomolecules in the data set known to have the particular biological function correlated with the descriptor.

Preferably, the functional site descriptor is also compared with biomolecules known not to exhibit the functionality associated with that functional site. That is, the descriptor is also compared to structures or molecules known not to have that function. If the functional site descriptor known to have a specified function matches or compares favorably to only biomolecules known to have the particular function, and not to biomolecules known not to have that function, the geometric parameters (or other parameters comprising the functional site descriptor) can be expanded (or relaxed) further. For example, in one aspect, the delta associated with one or more interatomic distances, and preferably all of such distances in a given functional site descriptor, can be expanded by a specified amount, i.e., by a "multiplier." Once the parameters of the descriptor have been so expanded, the functional site descriptor can be applied again to the data set to determine whether it matches a sufficient number of the existing active sites known to have this function, without encompassing structures that are known not to have this function. This is illustrated by steps 272 and 274 and the flow line between steps 276 and 272 in FIG. 5.

As stated above with reference to FIG. 5, in creating a functional site descriptor in step 272, geometries are adjusted to define a functional site descriptor that is broad enough to encompass active sites exhibiting the same functionality yet not so broad as to encompass active sites that do not have the desired functionality.

Figure 7:
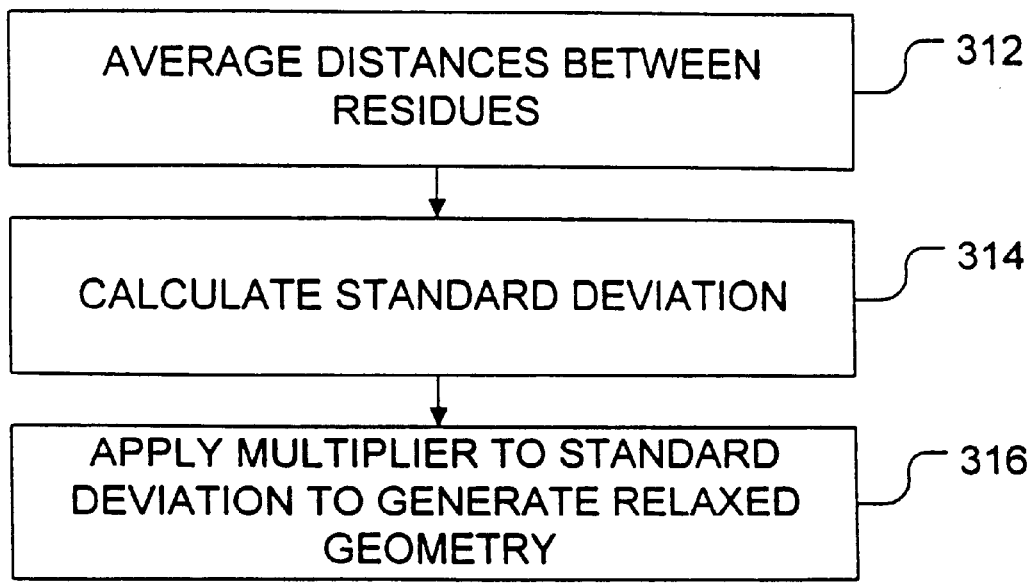
FIG. 7 is an operational flow diagram illustrating one example process for adjusting distance geometries according to one embodiment of the invention.

FIG. 7 is an operational flow diagram illustrating a process for adjusting one or more geometric distance parameters of a functional site descriptor according to the invention. Thus, in step 312, one or more, and preferably all, of the distances between residues of the functional site descriptor are averaged by comparing such distances (or mean distances) in known structures having the particular biological function correlated with the particular functional site descriptor.

In step 314, a standard deviation for each distance parameter is then calculated. In step 316, a multiplier is applied to the standard deviation to further relax the parameter geometry. Preferably, in some embodiments, each standard deviation is multiplied by the selected multiplier, and the distance between a residue pair is defined as the average distance between that residue pair across the group, plus or minus the standard deviation multiplied by the multiplier.

As stated above, such a relaxed functional site descriptor can then be applied to the data set to determine how many known active sites can be positively identified by the particular functional site descriptor. As also described above, this comparison can be performed in an integrated fashion, and one or more of the parameters of the descriptor can be broadened on subsequent iterations to encompass additional biomolecules in the data set known to have the desired biological function. Preferably, in the embodiment described with reference to FIG. 6, the broadening can be accomplished by increasing the multiplier by which standard deviations are multiplied. Of course, different multipliers can be applied to different distance parameters, as those in the art will appreciate.

In one embodiment, the multiplier chosen is the same for each distance in the data set. This simplifies computation in that a complete iteration can be formed by merely adjusting a single multiplier and applying that multiplier across the board. However, after reading this description, it will become apparent to one of ordinary skill in the art that alternative embodiments can be implemented wherein a different multiplier can be selected and applied for each distance in the descriptor. In performing the iterations to broaden the one or more geometric parameters of the descriptor, these multipliers can be changed by varying amounts to optimize the fit of the functional site descriptor to the data set. Indeed, as additional biomolecules are identified as having the desired function, particularly those where the corresponding structures have been experimentally solved, this process can be further iterated to further refine the particular functional site descriptor.

FIG. 8 is a diagram illustrating an example data set for geometric constraints of a "9 distance" functional site descriptor developed in accordance with instant process. This descriptor describes the active site of phospholipase A2. The data set in FIG. 8 is illustrated in tabular form for ease of description. The rows in FIG. 8 correspond to the distance parameters (written as average distances plus or minus a standard deviation multiplied by a multiplier (here, 2.0)) of the functional site descriptor (here, for the active site for enzymes having phospholipase activity). For the embodiment described above where nine distances make up the active site, there are preferably nine distances illustrated by the referenced characters A→B, B→C, A→C, A−1→B, A+1B, C−1→A, C+1→A, B−1→A, B+1→A. The columns in FIG. 8 provide the pertinent data for each residue pair distance. In the example illustrated in FIG. 8, these include the average distances 322 for the residue pairs, the standard deviation 324 of these distances among the data set, and the multiplier 326 used to broaden the geometry to the desired breadth. multiplier 326 used to broaden the geometry to the desired breadth.

Figure 9:
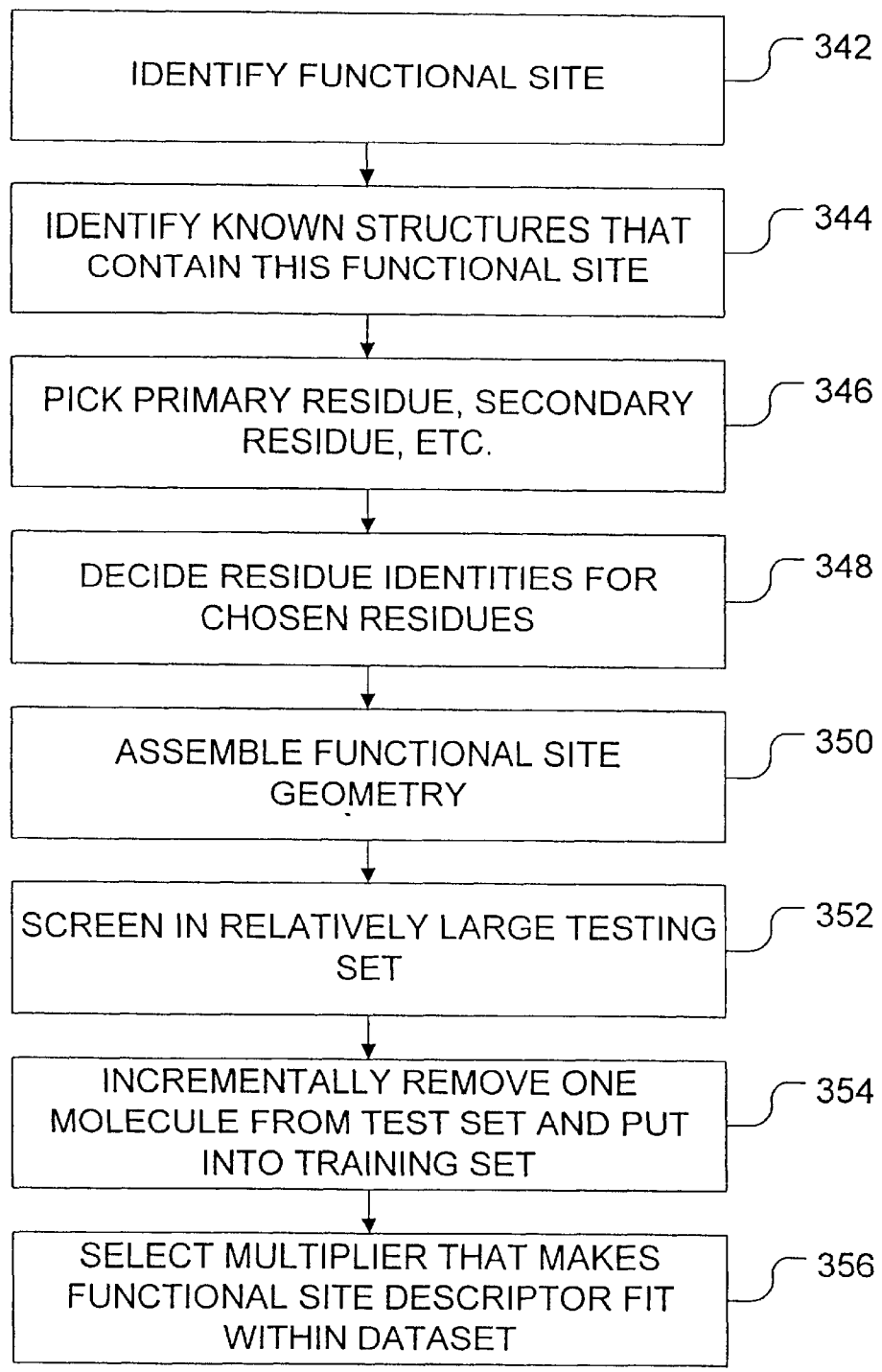
FIG. 9 is an operational flow diagram illustrating selection of a multiplier to be used in determining how much relaxation can be used with regard to one or more of the geometries (e.g., distance range) used in a given functional site descriptor, for example, an active site descriptor.

Preferably, in one embodiment, the functional site descriptor is created with a process that includes steps of training the data set to enhance the results. FIG. 9 is an operational flow diagram illustrating a process for creating a functional site descriptor including techniques for training the data set according to one embodiment of the invention. Referring now to FIG. 9, in a 342, a functional site geometry having a known function is selected. The primary, secondary, tertiary and so on residues are identified within that functional site geometry. This is illustrated by step 344. In a step 346, the identity(ies) for each residue is(are) chosen. Preferably, these choices are made based on an analysis of existing structures or other information relating to the particular biological function under consideration.

Known structures or molecules that possess the particular biological function can be selected as a test group for creating and refining the functional site descriptor, as illustrated by step 348. In step 350, the distance geometries are calculated. In preferred embodiments, this is accomplished as described above, whereby the distances between selected residue pairs are computed, averaged for the data set, and adjusted based on the standard deviation multiplied by some multiplier. Multipliers typically are in the range of about 0.1 to 100 for distance geometries, with multipliers of 1.0, 1.5, and 2.0 being particularly preferred.

In step 352, the functional site descriptor is screened against a relatively large testing set. The testing set includes molecules of structures known to contain the active site of interest, as well as molecules or structures that are known to not contain that active site. Preferably, as described above, the screening is done with gradually increasing the relaxation of one or more of the parameters of the descriptor (e.g., by increasing a distance geometry multiplier) in an iterative fashion. To train the data set, in a step 354, one molecule is removed from the test set and put into a training set upon each iteration. In step 356, the iterative process continues until the functional site descriptor comprises parameters that fit well within the data set. This training process is referred to in the computer arts as jack-knife training.

Having thus described the techniques for creating a functional site descriptor according to the invention, the discussion now turns in a non-limiting fashion to utilizing a functional site descriptor or a group of functional site descriptors (i.e., a library of functional site descriptors), to identify a biological function encoded by a novel nucleotide sequence, or biomolecule for which this function has not previously been identified.

Figure 10:
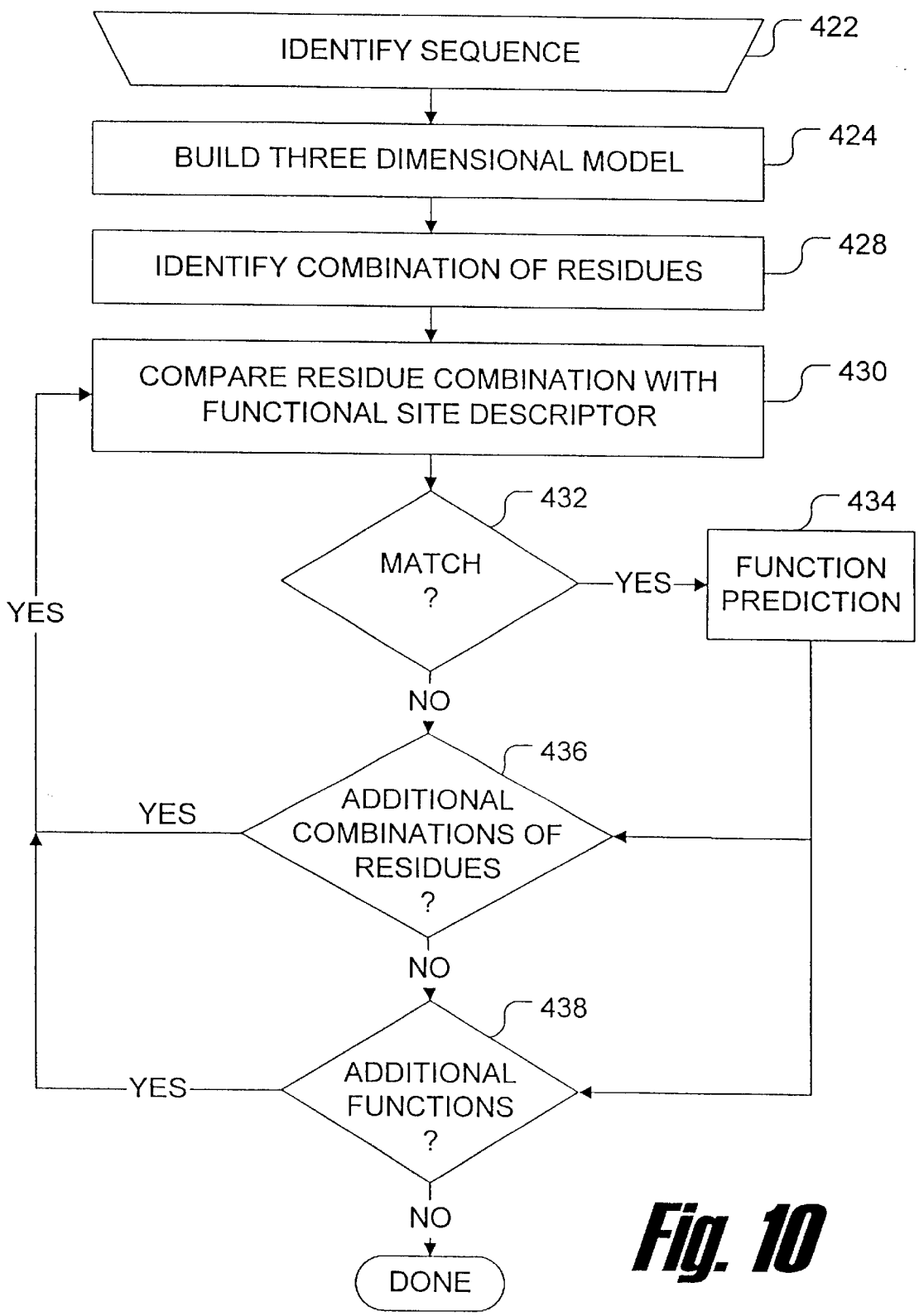
FIG. 10 is an operational flow diagram illustrating a process for utilizing one or more functional site descriptors to determine whether a nucleotide or amino acid sequence encodes such function(s).

FIG. 10 is an operational flow diagram illustrating a process for utilizing a functional site descriptor to determine whether a nucleotide and/or amino acid sequence encodes a particular biological function. In step 422, the sequence for testing is identified. This sequence can be a new sequence that has just been identified, or an existing sequence. If the sequence is a nucleotide sequence, the amino acid sequence is deduced using standard algorithms before proceeding to the next step. The biomolecule encoded thereby (e.g., a protein, enzyme, ribozyme, etc.) may be naturally occurring, completely synthetic, or anything in between. For purposes of illustration, FIG. 10 assumes that the sequence encodes a naturally occurring protein, for example, an enzyme. In step 424, a three-dimensional model of the enzyme having that primary sequence is created, for example, by application of a threading, ab initio, or other protein folding algorithm. As those in the art will appreciate, any algorithm useful in generating three-dimensional structural models can be used, e.g., homology modeling, threading or ab initio folding algorithms.

In a step 428, a residue combination that includes the residues associated with the functional site geometry (or of the functional site descriptor) of the subject function are identified from the three-dimensional folded sequence. For example, if the active site descriptor for the functional site under consideration includes three residues, a Cys, Cys, and a Pro residue, the combinations of the cys, cys, and pro residues are identified within the folded sequence. Initial filtering can be performed to screen out combinations that obviously are not of the appropriate geometry to fall within the geometry associated with the active site descriptor.

In a step 430, the identified residue combination is compared with the functional site descriptor to determine whether there is a match. If there is a match, the subject folded sequence can be predicted to have the desired function as illustrated by steps 432 and 434. Additional residue combinations can be compared with the functional site descriptor to determine whether these additional combinations match the functional site descriptor. This is illustrated by step 436. Once the residue combinations have been identified for the functional site descriptor, the process can be repeated for other functional site descriptors and other combinations of residues that may comprise other functional sites in that protein. This is illustrated by step 438.

Figure 11:
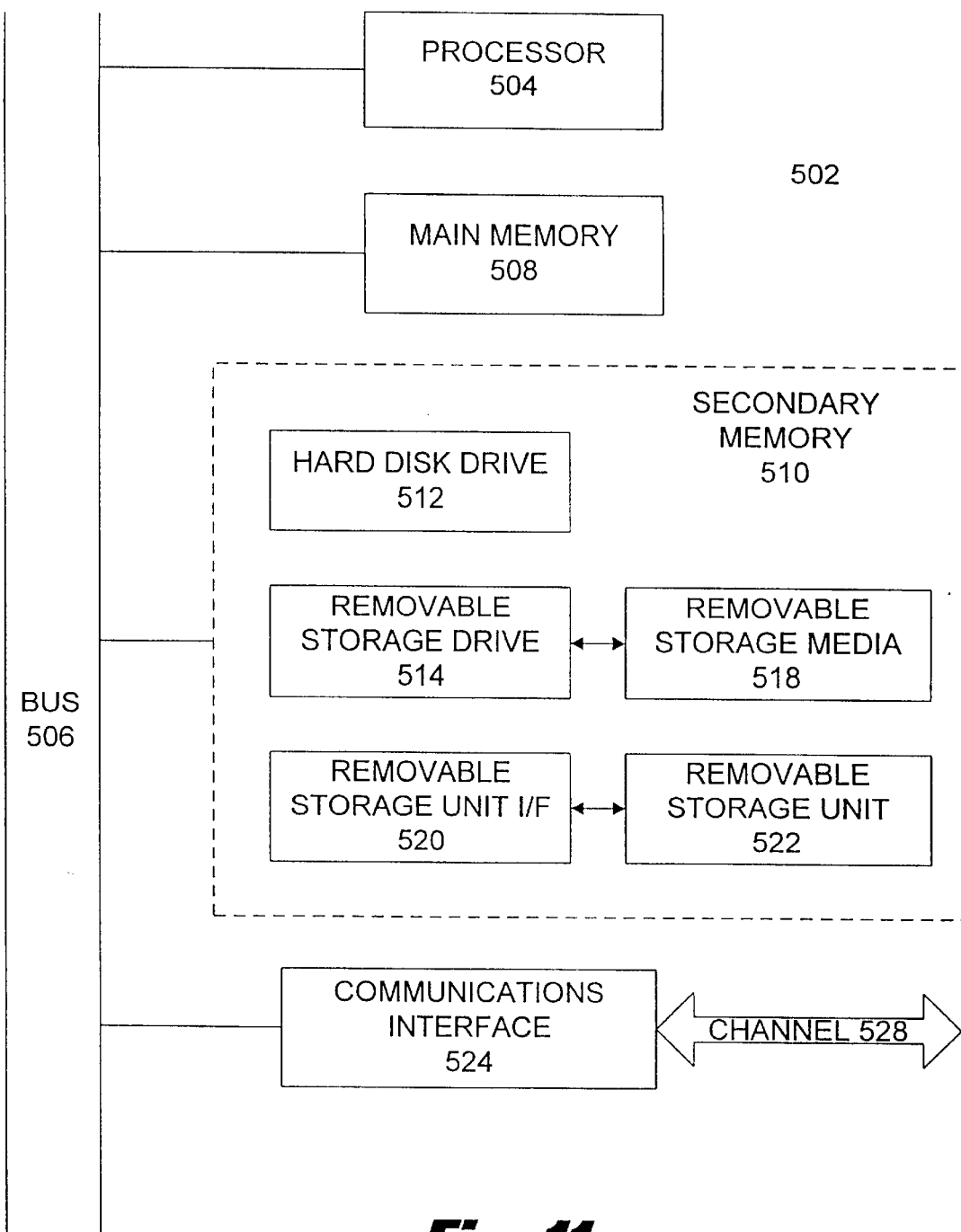
FIG. 11 is a block diagram illustrating an example processor-based system according to one embodiment of the invention.

The various embodiments, aspects, and features of the invention described above may be implemented using hardware, software, or a combination thereof and may be implemented using a computing system having one or more processors. In fact, in one embodiment, these elements are implemented using a processor-based system capable of carrying out the functionality described with respect thereto. An example processor-based system 502 is shown in FIG. 11. The computer system 502 includes one or more processors, such as processor 504. The processor 504 is connected to a communication bus 506. Various software embodiments are described in terms of this example computer system. The embodiments, features and functionality of the invention as described above are not dependent on a particular computer system or processor architecture or on a particular operating system. In fact, given the instant description, it will be apparent to a person of ordinary skill in the relevant art how to implement the invention using other computer or processor systems and/or architectures.

Processor-based system 502 can include a main memory 508, preferably random access memory (RAM), and can also include a secondary memory 510. The secondary memory 510 can include, for example, a hard disk drive 512 and/or a removable storage drive 514, representing a floppy disk drive, a magnetic tape drive, an optical disk drive, etc. The removable storage drive 514 reads from and/or writes to a removable storage medium 518. Removable storage media 518 represents a floppy disk, magnetic tape, optical disk, etc. which is read by and written to by removable storage drive 514. As will be appreciated, the removable storage media 518 includes a computer usable storage medium having stored therein computer software and/or data.

In alternative embodiments, secondary memory 510 may include other similar means for allowing computer programs or other instructions to be loaded into computer system 502. Such means can include, for example, a removable storage unit 522 and an interface 520. Examples of such can include a program cartridge and cartridge interface (such as that found in video game devices), a removable memory chip (such as an EPROM, or PROM) and associated socket, and other removable storage units 522 and interfaces 520 which allow software and data to be transferred from the removable storage unit 518 to computer system 502.

Computer system 502 can also include a communications interface 524. Communications interface 524 allows software and data to be transferred between computer system 502 and external devices. Examples of communications interface 524 can include a modem, a network interface (such as, for example, an Ethernet card), a communications port, a PCMCIA slot and card, etc. Software and data transferred via communications interface 524 are in the form of signals which can be electronic, electromagnetic, optical or other signals capable of being received by communications interface 524. These signals are provided to communications interface via a channel 528. This channel 528 carries signals and can be implemented using a wireless medium, wire or cable, fiber optics, or other communications medium. Some examples of a channel can include a phone line, a cellular phone link, an RF link, a network interface, and other communications channels.

In this document, the terms "computer program medium" and "computer usable medium" are used to generally refer to media such as removable storage device 518, a disk capable of installation in disk drive 512, and signals on channel 528. These computer program products are means for providing software or program instructions to computer system 502.

Computer programs (also called computer control logic) are stored in main memory 508 and/or secondary memory 510. Computer programs can also be received via communications interface 524. Such computer programs, when executed, enable the computer system 502 to perform the features of the present invention as discussed herein. In particular, the computer programs, when executed, enable the processor 504 to perform the features of the present invention. Accordingly, such computer programs represent controllers of the computer system 502.

In an embodiment where the elements are implemented using software, the software may be stored in, or transmitted via, a computer program product and loaded into computer system 502 using removable storage drive 514, hard drive 512 or communications interface 524. The control logic (software), when executed by the processor 504, causes the processor 504 to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to persons skilled in the relevant art(s). In yet another embodiment, elements are implemented using a combination of both hardware and software.

EXAMPLES

The following examples are provided to illustrate the practice of preferred embodiments of the instant invention, and in no way limit the scope of the invention.

Example 1

Sequence-To-Structure-To-Function Prediction of Oxidoreductase Activity of Glutaredoxins/ Thioredoxins and the RNA Hydrolytic Activity of the T1 Ribonucleases (a) Introduction In this example, the active sites responsible for the disulfide oxidoreductase activity of the glutaredoxin/thioredoxin family in *E. coli* and the RNA hydrolytic activity of the T1 ribonuclease family are described as functional site descriptors. Then, these descriptors are shown to correctly identify the appropriate active site (for example, that enabling oxidoreductase catalytic activity) in a library of high resolution protein structures produced by X-ray crystallography or NMR spectroscopy, most of which proteins had previously been identified as having other activities, but not oxidoreductase or ribonuclease activity. Next, these functional site descriptors are used to screen for and successfully identify active sites in low-to-moderate resolution structures predicted by ab initio folding or threading algorithms. Also described is the prediction of a function of a yeast protein whose three-dimensional structure was predicted using a threading algorithm. These results, described in greater detail below, demonstrate that low-to-moderate resolution structures produced by tertiary structure prediction algorithms can be used to identify a functional site, e.g., an active site, in a predicted three-dimensional biomolecule structure derived from a deduced primary structure determined from a nucleotide sequence. Automation of these methods, in conjunction with libraries of functional site descriptors, enables the large scale functional screening of nucleotide or protein sequence databases, first by predicting one or more three-dimensional structures from one or more sequences, then by identifying functional sites, e.g., active site, in the predicted structure(s).

(b) Difficulties with Local Sequence Motif for Identifying Protein Function

As discussed above, local sequence signatures correlated with function become increasingly less specific as the number of sequences within a protein family increases. Examination of the 1152 patterns in the Prosite database (Release 13.0, November 1995), 908 (79%) of the patterns were specific for their sequences, using the set of true and false positives and negatives identified by the Prosite developers. However, as the number of observed instances of a local sequence motif increased, the number of false positives also increased. For example, with respect to 10.5% of the patterns, 90–99% of the selected sequences were true positives. However, for the remaining 10.5% of the patterns, less than 90% of the selected sequences were true positives.

Ambiguity of local sequence motif-mediated identification of protein function also occurs in other local sequence motif databases, e.g., Blocks and Prints. For example, the Sep. 10, 1997, release of the Prosite database lists ill true positives, five false positives, and one false negative for the thioredoxin sequence signature PS00194. The five false positives, YNC4_CAEEL and the POLG proteins from four poxviruses) are not identified by the thioredoxin sequence signature in the Blocks or Prints databases, as shown in Table 1, below.

TABLE 1

Classification of possible thioredoxin sequences by the Prosite, Prints and Blocks motif databases.

| | Sequence recognized by: | | |
|---|---|---|---|
| | Prosite | Prints | Blocks |
| A. Probable false positives found by Prosite | | | |
| YNC4_CAEEL | X | | |
| POLG_PVYC | X | | |
| POLG_PVYN | X | | |
| POLG_PVYHU | X | | |
| POLG_PVYO | X | | |
| B. Sequences found by keyword search of SwissProt for "thioredoxin" | | | |
| DSBC_HAEIN | | | X |
| THIO_CHLLT | | X(2)* | X |
| THIO_CHRVI | | X | X |
| THIO_RHORU | | X | |
| YX09_MYCTU | | X | |
| Y039_MYCTU | | | |
| YB59_HAEIN | | | X |
| C. Sequences with some experimental evidence | | | |
| YME3_THIFE** | | | X |

Prosite: recent Prosite database online (thioredoxin examples updated 9/10/97)
Prints: search of OWL26.0 database
Blocks: search of SwissProt32
*Prints uses three different sequence signatures to recognize the thioredoxins. "2" means that this sequence was recognized by only two of the three signatures.
**A plasmid in *E. coli* expressing this gene product complements a thioredoxin mutant, providing experimental evidence that this protein may be a glutaredoxin or thioredoxin.

Database searches revealed that other protein sequences suspected of belonging to the thioredoxin family are not found by the Prosite, Blocks, and Prints local sequence motifs for thioredoxin. For example, a keyword search of SwissProt via the Sequence Retrieval System (SRS) at EMBL) using the term "thioredoxin" revealed seven additional sequences (see Table 1, above) that were identified as thioredoxins or probable thioredoxins by the depositors of those sequences. These sequences were variously classified by Prosite, Prints, and Blocks. One sequence in SwissProt, Y039_MYCTU, is not identified as a thioredoxin by any of these local sequence motif databases.

Experimental evidence reveals that other proteins also belong to the thioredoxin family, but are often not identified by the motif databases (Table 1C). For example, YME3_THIFFE is a predicted 9.0 kD protein in the MOBE 3' region (ORF 8) in *Thiobacillus ferrooxidans*. A clone containing this gene complements an *E. coli* thioredoxin mutant, providing experimental evidence that this protein falls into the glutaredoxin/thioredoxin family. In addition, a BLAST search of a non-redundant sequence database (Genbank CDS translations, PDB, SwissProt, and PIR; using YME3_THIFE as the search sequence identified two significant matches (to a periplasmic hydrogenase from *D. vulgaris* (PHFL_DESVO) and ORF-R5 from Anabaena) and two potential matches (one of which is GLRX_METTH, a glutaredoxin-like protein from *Methanobacterium thermoautotrophicum*). A sequence alignment between GLRX_METTH and YME3_THIFE shows conservation of the active site cysteines. Thus, even though YME3_THIFE has weak sequence similarity to known thioredoxins, and experimental evidence supports such an assignment, the sequence is not identified as such by a comparison with the local sequence motifs of the Prosite database because it contains only a portion of either the glutaredoxin or thioredoxin Prosite local sequence motifs. The YME3_THIFE sequence is also not identified as a thioredoxin by Prints, although it classified as a glutaredoxin by the Blocks database.

(c) Disulfide Oxidoreductase Functional Site Descriptor

The glutaredoxin/thioredoxin protein family is comprised of small proteins that catalyze thiol-disulfide exchange reactions via a redox-active pair of cysteines in the active site (Yang & Wells, 1991a; Yang & Wells, 1991b). While glutaredoxins and thioredoxins catalyze similar reactions, they are distinguished by their differential reactivity. Glutaredoxins contain a glutathione binding site, are reduced by glutathione (which is itself reduced by glutathione reductase), and are essential for the glutathione-dependent synthesis of deoxyribonucleotides by ribonucleotide reductase (Holmgren & Aslund, 1995). In contrast, thioredoxins are reduced directly by the flavoprotein, thioredoxin reductase, and act as more general disulfide reductases (Holmgren & Bjornstedt, 1995). Ultimately, however, reducing equivalents for both proteins come from NADPH. Protein disulfide isomerases (PDIS) have been found to contain a thioredoxin-like domain and thus also have a similar activity (Kemmink et al., 1997; Kemmink et al., 1995).

The active site of the redoxin family contains three invariant residues: two cysteines and a cis-proline. Mutagenesis experiments have shown that the two cysteines separated by two residues are essential for significant protein function. The side chains of these two residues are oxidized and reduced during the reaction (Bushweller et al., 1992; Yang & Wells, 1991b). These two cysteines are located at the N-terminus of an a-helix. Another unique feature of the redoxin family is the presence of a cis-proline located close to the two cysteines in folded, three-dimensional structures, but not in the primary structures, i.e., the one-dimensional representations of the amino acid sequences. While this proline is structurally conserved in all glutaredoxin and thioredoxin structures (Katti et al., 1995) and is invariant in aligned sequences of known glutaredoxins and thioredoxins, its functional importance is unknown. Other residues, particularly charged residues, have been shown to be important for the specific thiol ionization characteristics of the cysteines, but are not essential and can vary within the protein family (Dyson et al., 1997).

The functional site descriptor for the disulfide oxidoreductase activity (i.e., a biological function) of the glutaredoxin/thioredoxin family was built as follows using the three amino acids discussed above: the structure of the active site was taken from the three-dimensional structural comparison of bacteriophage T4 glutaredoxin, 1aaz (Eklund et al., 1992), human thioredoxin, 4trx (Forman-Kay et al., 1990), and disulfide bond formation protein, 1dsb (Martin et al., 1993). The the active sites of these three proteins can be aligned the α-carbon distances of the two cysteine amino acids and the cis-proline amino acid of the functional site descriptor appearing in FIG. 12. The following disulfide oxidoreductase functional site descriptor was thus developed: two cysteines separated by two residues and an α-carbon distance of 5.5+/−0.5 Å. These cysteines must be close to a proline residue. Specifically, the α-carbon distance from Cys(i) to the proline is 8.5+/−1.5 Å and that from Cys(i+3) to the proline is 6.0+/−1.0 Å. These three sets of distances comprise the distances-only functional site descriptor for the glutaredoxin/thioredoxin family. There is some evidence that the cysteines must be at the N-terminus of a helix because of the effect of the helix macrodipole on the sulfhydryl ionization (Kortemme & Creighton, 1995; Kortemme & Creighton, 1996); however, this evidence is disputed (Dyson, et al., 1997), so this characteristic is applied only if necessary. Below is a table listing a "9 distance" geometric constraint set for the disulfide oxidoreductase functional site descriptor.

TABLE 2

Disulfide oxidoreductase FSO

| | AVE DIST | STD DEV | MULT |
|---|---|---|---|
| A→B | 5.39 | 0.18 | 2.0 |
| B→C | 5.76 | 0.54 | 2.0 |
| A→C | 8.37 | 1.19 | 2.0 |
| A − 1→B | 7.96 | 0.62 | 2.0 |
| A + 1→B | 5.31 | 0.16 | 2.0 |
| C − 1→A | 8.10 | 1.18 | 2.0 |
| C + 1→A | 11.97 | 1.15 | 2.0 |
| B − 1→A | 5.79 | 0.24 | 2.0 |
| B + 1→A | 6.66 | 0.35 | 2.0 |

A = Cys
B = Cys or Ser
C = Pro (d) Validation of the Disulfide Oxidoreductase Functional Site Descriptor The distances-only functional site descriptor from section (b), above, is almost sufficient to uniquely distinguish proteins belonging to the glutaredoxin/thioredoxin family from a data set of 364 non-redundant proteins whose structures have been previously elucidated taken from the Brookhaven database. For this set of 364 proteins, 13 have the sequence signature —C—X—X—C—. Of these, only three, 1thx (thioredoxin), 1dsbA (protein disulfide isomerase, chain A), and 1prcM (photosynthetic reaction center, chain M), have a proline within the distances specified in the descriptor. Of these three proteins, only 1thx and 1dsb have two cysteines positioned at or near the N-terminus of a helix. These two proteins are the only two "true positives" in the test data set (as 1prcM does not exhibit the desired activity), establishing that this distance-only functional site descriptor is quite specific for the disulfide oxidoreductase activity of the glutaredoxin/thioredoxin protein family. When the requirement that the cysteines be at the N-terminus of a helix is included, then the 1prc-M site is also eliminated, making the functional site descriptor absolutely specific for the glutaredoxin/thioredoxin disulfide oxidoreductase function.

To explore if one or more distance parameters of this functional site descriptor can be relaxed, the allowed variance in the Cys-Pro and Cys-Cys α-carbon distances was uniformly increased in increments of +/−0.1 Å. Upon increasing the allowed distances by +/−0.1 Å and applying this relaxed descriptor to the same subset of 364 proteins from the Brookhaven database, 1fjm (Goldberg et al., 1995), a serine/threonine phosphatase, 1lct (Day et al., 1993), a lactoferrin, and 1prc-C (Deisenhofer et al., 1995), the C-chain of the photosynthetic reaction center, were also predicted by the distance-only functional site descriptor to have the desired function. The Cys-Cys-Pro site in 1fjm is curiously similar to that found in the glutaredoxin/thioredoxin family, including the proline being in a cis-conformation, but the cysteines are at the C-terminus, not the N-terminus, of a helix. 1lct, an iron transport protein, contains a proline near a cluster of metal-binding cysteines. These cysteines are in a very irregular structure, not in a helix. In 1prc-M, the Cys-Cys-Pro structural motif is located along one face of a transmembrane helix, near the helix's C-terminus. In 1prc-C, the Cys-Cys-Pro are located in another very irregular region. Thus, all four proteins found by the relaxed distance-only FFF are eliminated when the helix requirement is included. When the distance constraints are relaxed even further (to +/−0.3 Å), only one other protein, 2fd2 (Soman et al., 1991), a ferredoxin (also a metal-binding protein), was selected from this same subset of known structures from the Brookhaven database. Again, the cysteines are found in a nonregular structural region, not in a helix. Thus, when the functional site descriptor includes the conformational parameter that the cysteines be located at the N-terminus of a helix, all false positives can be excluded, even when the functional site descriptor distance constraints are relaxed by +/−0.3 Å.

(d) Application of the Disulfide Oxidoreductase Functional Site Descriptor to Inexact Models (i) Structures Predicted by MONSSTER ab initio folding Algorithm The MONSSTER algorithm was benchmarked against a set of proteins whose structures had previously been determined by x-ray crystallography or NMR spectroscopy (Skolnick et al., *J. Mol. Biol.* 265:217–241 (1997). The structure of *E. coli* glutaredoxin, 1ego (Xia et al., 1992), was predicted by MONSSTER as part of this validation procedure. The correctly predicted structures are inexact models, i.e., when the models are compared to the known protein structures, the RMSD ranges from 3 to 7 Å. For example, in 1ego, the best inexact model produced by MONSSTER is 5.7 Å RMSD between corresponding α-carbons. Furthermore, the sequence of this glutaredoxin exhibits less than 30% sequence identity to any of the three structures used to create the disulfide oxidoreductase functional site descriptor. The disulfide oxidoreductase functional site descriptor was applied to 25 correct structures and 56 incorrect, or misfolded structures generated by MONSSTER for the 1ego sequence during the isothermal runs. The distances-only functional site descriptor selected all 25 "correct" structures as belonging to the redoxin family and rejected all 56 misfolded structures. Next, a set of 267 correctly and incorrectly predicted structures produced by the MONSSTER algorithm for five other proteins was then created. The distances-only glutaredoxin/thioredoxin functional site descriptor was specific for the correctly folded 1ego structures and did not recognize any of the other correctly or incorrectly folded structures among those tested. Inclusion of the criterion that the cysteines be at the N-terminus of a helix did not change these results.

To further explore relaxation of functional site descriptor parameters as applied to these inexact models, the distance constraints were again relaxed by +/−0.2 Å. With this level of relaxation, the descriptor was still specific for all correctly folded 1 ego structures. When the variance was relaxed to ±0.3 Å, the distance-only descriptor also selected 2 of the 56 misfolded 1ego structures, in addition to the 25 correctly folded structures. When the allowed variance was further relaxed to 0.5 Å, no additional incorrectly folded structures were selected. These results demonstrate the specificity and the uniqueness of the glutaredoxin/thioredoxin disulfide oxidoreductase functional site descriptor for low-resolution predicted models of protein structure.

(ii) Structures Predicted by "Threading" Algorithm

As ab initio structure prediction algorithms such as MONSSTER are too computationally intensive to be applied to large scale screening, as is required for genome-wide screening projects, the use of three-dimensional protein models produced by threading or inverse folding algorithms are preferred. The disulfide oxidoreductase functional site descriptor was used to probe several proteins from the yeast genome. The selected protein sequences were aligned with a database of 301 non-homologous protein structures (Fischer et al., 1996) using an inverse folding or threading algorithm (Godzik & Skolnick, 1992).

Sequence-to-structure alignments were performed by a "local-global" version of the Smith-Waterman dynamic programming algorithm (Waterman, 1995). The alignments were ranked by three different scoring methods (Jaroszewski et al., 1997). The first scoring method was based on sequence-sequence type scoring using the Gonnet mutation matrix to optimize gap penalties, as described by Vogt and Argos (Vogt et al., 1995). The second method was a sequence-structure scoring method based on the pseudo-energy from the probe sequence "mounted" in the structural environment in the known structure. The pseudo-energy term reflected the statistical propensity of successive amino acid pairs (from the probe sequence) to be found in particular secondary structures within the template structure. The third method was a structure-structure scoring method, whereby information from the known template structure was compared to the predicted secondary structure of the probe sequence. The secondary structure prediction scheme for the probe sequence employed the nearest neighbor algorithm (Rychlewski & Godzik, in preparation). The version used here achieved an average three-state prediction accuracy of 74%.

Once scores had been computed for the sequence-to-structure alignments, the statistical significance of the each score was determined. To determine this significance, the distribution of scores was fit to an extreme value distribution and the raw score was compared to the chance of obtaining the same score when comparing two unrelated sequences (Jaroszewski et al., 1997).

Once the alignment of the probe sequence-to-template structure had been determined, a three-dimensional model was built. Scripts utilizing the automatic modeling tools provided by Modeller4 (Tripos Associates, St. Louis) were developed (L. Jaroszewski, K. Pawlowski, A. Godzik, unpublished) to automatically produce all-atom coordinate files for the three-dimensional model built from the sequence-to-structure alignment provided by the threading algorithm. The functional site descriptor was applied without relaxation directly to these structures without any further enhancement, energy calculations, or molecular mechanics simulations of the model.

The sequences of four proteins lacking significant homology from the *S. cerevisiae* genome database were tested using the disulfide oxidoreductase functional site descriptor: one protein was predicted to belong to the protein disulfide isomerase family (S67190), one sequence was identified in the database as a hypothetical thioredoxin (YCX3_YEAST), and two hypothetical proteins, one having very distant sequence similarity to glutaredoxin from rice (S51382) and the other with very distant sequence similarity (insignificant by the Blast score) to the glutaredoxin from *Methanococcus thermoautoformicum* (S70116). S51382 has not been identified as a glutaredoxin or thioredoxin in any sequence or motif database.

The threading algorithm (Godzik & Skolnick, 1992) aligned the sequences of all four known proteins to the structure of either 1ego (*E. coli* glutaredoxin (Xia et al., 1992)) or 2trx (*E. coli* thioredoxin (Katti et al., 1990)) from a database of 301 non-homologous proteins (Fischer et al., 1996). The alignment fit was strong, as the sequences were matched to either 1ego or 2trx (chain A) by all three scoring methods used to assess the significance of the threading results. Models were built based on the sequence-to-structure alignments and were screened with the functional site descriptor. All twelve models (four sequences times three scoring methods) were found to have the disulfide oxidoreductase active site described by the distances-only functional site descriptor.

Taken together, these results demonstrate that models produced by threading algorithms are sufficient for application of functional site descriptors to the identification of active sites in proteins, as well as their utility for large scale functional analysis of the genome databases using the sequence-to-structure-to-function paradigm of this invention.

(f) T1 Ribonuclease Functional Site Descriptor

A functional site descriptor was also developed for the active site of the T1 ribonucleases, a family of proteins that include a number of ribonucleases such as T1, T2, U2, and F1, and the distantly related family of fungal ribotoxins. These proteins are endoribonucleases generally specific for purine, particularly guanine, bases (Steyaert, 1997). Two histidines and a glutamic acid are known to be essential for these enzymes' catalytic activity, and a tyrosine, a phenylalanine (or another large hydrophobic residue), and an arginine are responsible for stabilizing the transition state of the reaction. These catalytic residues are located on various strands across one face of a β-sheet. Neither the Prosite, Prints, nor Blocks databases provide a local sequence signature that identifies this family.

An analysis of three T1 ribonucleases whose structures have been solved (1 rms (Nonaka et al., 1993), 1fus (Vassylyev et al., 1993), and 1rtu (Noguchi et al., 1995)) shows that the location of the active site residues in three-dimensional space is very well conserved. Thus, a functional site descriptor based on the distances between appropriate α-carbons was developed from these distances, plus or minus a small variance. The values of the distance parameters are given in the table inset in FIG. 12/2.

When applied to three-dimensional structures, the T1 ribonuclease functional site descriptor was implemented in three stages: first, each structure was searched for the residue triad involved in nucleophilic displacement (His-His-Glu); second, those structures having the His-His-Glu triad was searched for the residue triad involved in transition state stabilization (Tyr-Hydrophobic-Arg); and third, if both triads were found, the relative positions of the two triads was checked based only on the distances between α-carbons. Application of the functional site descriptor to the 364 non-homologous protein structures in the PDB database yielded only one structure containing both residue triads in the correct juxtaposition: 9rnt (Martinez-Oyanedel et al., 1991), the only true positive in the test data set. Increasing the allowed variation for each distance by ±0.5 Å yielded no additional hits, demonstrating this functional site descriptor's specificity for structures of the T1 ribonuclease family solved to atomic resolution, even when the distance restraints are relaxed.

To test the applicability of the T1 ribonuclease functional site descriptor to low resolution, predicted models, nine ribonuclease sequences were threaded through 301 non-homologous predictions. All nine sequences were matched as the highest score to the 9rnt structure by all three scoring methods. Models were built for all 27 (9 sequences times 3 scoring methods) sequence-to-structure alignments and all 27 models were screened with the T1 ribonuclease functional site descriptor. All 27 models were found to contain both Ti ribonuclease active site triads in the correct locations in the structure.

To test the method on more distantly related sequences, models of three ribotoxin sequences were built. Ribotoxins are a small family of proteins found in the *Aspergillus fungi* family. They cleave rRNA, inactivating the ribosome and ultimately killing the cell (Kao & Davies, 1995). The RNA cleavage is carried out by a mechanism quite similar to that found in the T1 ribonucleases (Campos-Olivas et al., 1996). The three selected ribotoxins, α-sarcin (RNAS_ASPGI), clavin (RNCL_ASPCL), and restrictocin (mitogillin) (RNMG_ASPRE), can be aligned to the T1 ribonucleases by multiple sequence alignment algorithms, but the sequence identity between the ribotoxins and the Ti ribonucleases is quite low (less than 35% pairwise sequence identity). Furthermore, a Blast (Altschul et al., 1990) search of SwissProt (Bairoch & Apweiler, 1996) using the sequence of 9rnt as the search sequence did not yield any of these ribotoxin sequences. The structures of α-sarcin (Campos-Olivas et al., 1996) and restrictocin (Yang & Moffat, 1996) have been solved, but neither has yet been released to a public database.

The three ribotoxin sequences, including their signal sequences, were threaded through 301 non-homologous protein structures (Fischer et al., 1996). As with the T1 ribonucleases, each ribotoxin sequence aligned to 9rnt as the highest scoring sequence by all three scoring methods, although the alignment scores were much lower than those for the T1 ribonucleases themselves. Nine models (three sequences times three scoring methods) were built based on the sequence-to-structure alignments produced by the threading program. All nine models contained both the nucleophilic and the transition state stabilization triads and were recognized by the T1 ribonuclease functional site descriptor. This result also demonstrates that models of distantly related proteins can be built based on sequence-to-structure alignments produced by a threading algorithms Active sites within these low-to-moderate resolution models can be recognized by the functional site descriptor.

This example demonstrates the instant invention's ability to predict protein function based on the three-dimensional structure of an active site. The method, which is amenable to automation, uses a sequence-to-structure-to-function paradigm wherein the protein's structure is first predicted from its amino acid sequence, after which the active site of the protein is identified in the predicted model using a functional site descriptor. Function is then assigned based on the particular functional site descriptor that aligns with the predicted structure of the protein.

The instant invention has the following advantages (each is discussed in further detail in the following paragraphs): 1) it is applicable even when the sequence identity between two proteins is not significant; 2) it can be used with proteins having different global folds, but similar active sites and associated function; 3) it distinguishes between proteins with similar folds (topological cousins) and those that belong to a given functional family; and 4) in addition to assigning a given protein to a functional family, the method produces a three-dimensional map or model of the protein's active site.

Example 2

Functional Screening of the *E. coli* Genome to Identify Proteins Having Disulfide Oxidoreductase Activity (a) Introduction This example describes automated application of the sequence-to-structure-to-function paradigm of the invention to the complete *Escherichia coli* genome (i.e., all ORFs) to identify proteins having the thiol-disulfide oxidoreductase activity of the glutaredoxin/thioredoxin protein family. As described below, protein structures are predicted by a threading algorithm from amino acid sequences deduced from nucleotide sequence information. The threading algorithm generates a model of each protein's structure by aligning its primary sequence to the best matching structure in a structural database and extending the sequence analysis well beyond the limits of local sequence identity. The modeled structure is then probed with a functional site descriptor for the active site responsible for the thiol-disulfide oxidoreductase activity of the glutaredoxin/thioredoxin protein family, namely the functional site descriptor for oxidoreductase activity described in Example 1. After conducting this analysis for each ORF in the *E. coli* genome, ten sequences previously known or proposed have this oxidoreductase activity were identified, as were two other sequences not previously identified as having this function.

(b) Experimental

*E. coli* is a very widespread, medically important organism that colonizes in the lower gut of animals. It is also responsible for a variety of infections and diseases.

1993), and 174 to 2trx, chain A (Katti et al., 1990). These alignments were further screened to determine if the aligned sequence had the active site residues of the oxidoreductase functional site descriptor at the appropriate positions in the template structure. Sequences that aligned to one of the three structures and contained the active site residues of the descriptor were assigned to exhibit thiol-disulfide oxidoreductase activity.

Using this procedure, 39 different alignments for 12 different sequences (some sequences were selected by all three of the scoring functions) were found to match the oxidoreductase functional site descriptor, and thus were predicted to have the thiol-disulfide oxidoreductase active site. These ORF's are listed in Table 3, below.

TABLE 3

Glutaredoxins and thioredoxins identified in *E. coli* strain K-12.

| Database name | Thrd/FSD | Blst/FSD | Functional Motif ps | pps | pb | b | Database description |
|---|---|---|---|---|---|---|---|
| GLR1_ECOLI | x | x | x | x | x | x | glutaredoxin 1 |
| GLR2_ECOLI | x | | x | | x* | x | glutaredoxin 2 |
| GLR3_ECOLI | x | x | x | x | x | x | glutaredoxin 3 |
| THIO_ECOLI | x | x | x | x | x | x | thioredoxin |
| DSBA_ECOLI | x | x | x | | x** | x | thiol-disulfide interchange protein |
| DSBC_ECOLI | x | | x | | x* | x | thiol-disulfide interchange protein |
| DSBD_ECOLI | x | x | x | x | x | x | c-type cytochrome biogenesis protein; (inner-membrane Cu tolerance protein) |
| DSBE_ECOLI | x | | x | x* | x | x | thiol-disulfide interchange protein; (cyto c biogenesis protein CCMG) |
| YFIG_ECOLI protein | x | x | x | x | x | x | hypothetical thioredoxin-like |
| NRDH_ECOLI | x | | | | x** | x | glutaredoxin-like NRDH protein |
| NRDG_ECOLI | x | | | | | | anaerobic ribonucleoside triphosphate inactivating protein |
| B0853 | x | | | | | | ORF; putative regulatory protein |
| YIEJ_ECOLI | | x | | | | | hypothetical protein in tnaB-bglB intergenic region |

Database name: All sequences come from the SwissProt database (Bairoch & Apweiler, 1996), except B0853, which is the label given in the *E. coli* genome database (Blattner et al., 1997). This sequence can also be accessed by the Genbank accession number ECAE000187.
Thrd/FSD: Alignment of *E. coli* ORF to the sequences of 1ego, 1dsb (chain A), or 2trx (chain A) using a threading algorithm (Jaroszewski et al., 1998), followed by analysis of the resulting sequence-sequence alignment for the active site Furthermore, *E. coli* is a preferred organism for genetic, biochemical, and molecular biology studies and has been very well studied. Because of its importance in so many realms, it was one of the earliest candidates for genome sequencing (Neidhardt et al., 1996). The complete 4,639,221-base pair sequence of the genome of *E. coli* K-12, strain MG1655, has recently been published (Blattner et al., 1997), and nearly 40% of the ORFs encoded thereby were previously uncharacterized.

The protein sequences of 4290 open reading frames (ORFs) from strain K12 were threaded through a database of 301 non-homologous protein structures. Because the production of detailed atomic models is a very CPU-intensive process and is not yet a feasible approach for complete genome analysis, analysis using the sequence-to-structure alignments for those *E. coli* sequences that aligned to either 1 ego, 1 dsb, chain A, or to 2 trx, chain A, was employed, as these structures can be identified using the oxidoreductase functional site descriptor described in Example 1.

The top three alignments found by three different scoring functions (Jaroszewski et al., 1998) of the 4290 ORFs to 301 known structures were produced. Of the resulting 38,610 sequence-to-structure alignments, 162 alignments were to 1ego (Xia et al., 1992), 195 to 1dsb, chain A (Martin et al., 1993), and 174 to 2trx, chain A (Katti et al., 1990)

residues specified by the functional site descriptor for the thiol-disulfide oxidoreductase activity of the glutaredoxin/thioredoxin family (Fetrow & Skolnick, 1998). Threading results concern a combination of three different scoring methods, sq, br, and tt, as described by Godzik and coworkers (Jaroszewski et al., 1998). Briefly, Sq is a sequence-sequence type of scoring that uses a Gonnet mutation matrix (Gonnet et al., 1992) to optimize gap penalties (Vogt et al., 1995). Br is a sequence-structure scoring method that is based on the pseudo-energy from the probe sequence "mounted" in the structural environment in the template structure. The pseudo-energy term reflects the statistical propensity of successive residue pairs (from the probe sequenced) to be found in a particular secondary structure within the template structure. Tt is a structure-structure scoring method, whereby information from the known template structure is compared to the predicted secondary structure of the probe sequence. Secondary structure was predicted by a nearest neighbor algorithm (Ryschlewski & Godzik, 1997). From these scores, statistical significance was calculated based on a maximum value distribution (Jaroszewski et al., 1998).

Blst/FSD: Alignment of each *E. coli* ORF to the sequences of the 1ego (Xia et al., 1992), 1dsb, chain A (Martin et al., 1993), and 2trx, chain A (Katti et al., 1990)

proteins using the BLAST search protocol (Altschul et al., 1990), followed by analysis of the resulting sequence-sequence alignment for the active site residues specified by the thiol-disulfide oxidoreductase activity of the glutaredoxin/thioredoxin family. Results reported here are for a combination of the gapped-BLAST protocol and the PSI-BLAST alignment protocols (Altschul et al., 1997). All sequences marked are found by both gapped- and PSI-BLAST, except YIEJ_ECOLI, which is found only by gapped-BLAST.

Functional Motif: Search of each sequence found by either Blast or threading protocols against the local signature databases Prosite, Prints using the Prosite scoring method, Prints using the Blocks scoring method, or Blocks. Each sequence was copied from the appropriate sequence database to the appropriate form on the web pages given here. Each motif database was searched with the given sequence and the returned scores were analyzed to see if the thioredoxin or glutaredoxin families were identified.

As shown in Table 3 above, the Prosite database (Release 13 and updates to Nov. 28, 1997; Bairoch et al., 1995) identifies nine E. coli sequences that exhibit a glutaredoxin (PS00195) or thioredoxin (PS00194), active site. All nine of these proteins were also identified by threading/functional site descriptor procedure. The latter method also identified glutaredoxin 2, GLR2_ECOLI, which had been previously reported to be an atypical glutaredoxin (Vlamis-Gardikas et al., 1997), and is inconsistently classified by the local sequence motif databases (Prosite, Prints, and Blocks). In addition, this protein is not recognized as a glutaredoxin or thioredoxin by BLAST.

The threading/functional site descriptor procedure also identified three sequences not identified by Prosite as containing the thiol-disulfide oxidoreductase site: NRDH_ECOLI, NRDG_ECOLI, and B0853. NRDH_ECOLI is a small protein found in the nrdEF operon of E. coli that is involved in electron transport for ribonucleotide reductase. Searching the local signature databases with the NRDH sequence showed that the Prosite and Prints databases using the Prosite scoring function do not classify this sequence as a glutaredoxin. A Prints database search using the Blocks scoring function identified two out of the three motifs, and identified by Prints and Blocks with low significance. The second sequence, NRDG_ECOLI, has been classified as an anaerobic ribonucleoside-triphosphate reductase activating protein and is known to participate in redox reactions. B0853 is an ORF that has been classified as a regulatory protein. B0853 was not recognized by Prosite, Prints, or Blocks as having a glutaredoxin or thioredoxin active site. Thus, the methods of the invention accurately identified the activity of all ten of proteins accurately, as did the BLOCKS scoring method. NRDG_ECOLI and B0853 were also identified by the methods of the invention as having thiol-disulfide oxidoreductase activity.

Alignments of all E. coli ORFs were generated to the sequences of 1ego, 1dsb (chain A), and 2trx (chain A) using gapped- and PSI-BLAST. The oxidoreductase functional site descriptor was then applied to the resulting alignments. As shown in Table 3, above, the results of this procedure were not as powerful at identifying structurally related proteins as the threading algorithm. Moreover, GLR2, DSBC, and DSBE were missed by using state-of-the-art BLAST methods to produce the alignments.

These results indicate that application of functional site descriptors to threading alignments are necessary to derive useful function predictions. It has been shown that pairs of proteins can have similar structures but unrelated functions (Orengo et al., 1994). Such protein pairs are termed topological cousins. Because topological cousins exist and are common, knowledge of a protein's structure alone is insufficient to identify the protein's function. To demonstrate this point for the proteins studied here, the scores of the sequence-to-structure threading alignments were analyzed. For all three scoring methods, the significance scores range from close to zero to about 200 to 300, with an obvious set of outliers above 500. Sequences with significance scores greater than 1000 are identical to, or close homologues of, the template structure, while sequences with significance scores above 100 are most likely related to the template structure (Jaroszewski et al., 1998).

However, even if a sequence aligns to a specific structure with a significance score greater than 100, the functions of the two proteins were not necessarily the same. For example, the sequence YBBN_ECOLI yielded a very high significance score to 2trx, chain A, by all three scoring methods.

TABLE 4

Examples of possible glutaredoxin/thioredoxin topological cousins that do not exhibit oxidoreductase activity.

| Database name | Match | Thread Scores | | | Motifs | Name |
|---|---|---|---|---|---|---|
| YBBN_ECOLI | 2trxA | 12381 | 1580.2 | 221.4 | P-B | Hypothetical protein |
| B2475 | 1dsbA | 48.5 | 88.6 | 92.9 | | hypothetical, unclassified |
| SGBH_ECOLI | 1dsbA | | 96.9 | | | probable hexulose-6-phosphate synthase |

Database name: All sequences come from the SwissProt database (Bairoch & Apweiler, 1996), except B2475, as labeled in the label from the E. coli genome database (Blattner et al., 1997). This sequence can also be found under Genbank Accession number ECAE000334.
Match: The structure to which the sequence aligns by the threading method (Jaroszewski et al., 1998).
Thread Scores: These scores (sq, br, and tt, from left to right) are the significance scores described in the footnotes to Table 1. The sequence SGBH_ECOLI was aligned to 1dsbA only by the br scoring method, but not by the sq or tt methods.
Motifs: Each sequence was screened against the local motifs databases, Prosite (PS), Prints (P-PS or P-B), and Blocks (B), as described in the footnotes to Table 1.

Blocks identified the CXXC motif as a glutaredoxin motif, but the significance score was not high. When the sequence was first reported, the authors noted its similarity to some glutaredoxins. Recent experimental results have demonstrated that the protein is a functional redoxin. Thus, the methods of this invention clearly identified an active site that was not identified by either Blast or Prosite, but was By a BLAST sequence analysis, this sequence also had very high sequence identity to many thioredoxins; however, it was not recognized by the functional site descriptor because the most N-terminal of the active site cysteines was changed to a serine. This protein was a topological cousin, and since it just contains a single cysteine, it is unlikely to exhibit significant disulfide oxidoreductase activity;

however, it has been shown that a few of these proteins can still catalyze disulfide isomerization reactions when the second cysteine (but not the first) is replaced with serine (Wunderlich et al., 1995), though in most cases, the activity is significantly reduced (Bushweller et al., 1992; Walker et al., 1996). In those mutated proteins where only one cysteine is present, the second cysteine involved in the reaction mechanism comes from the substrate itself. These proteins tend to catalyze disulfide interchange reactions, but not complete redox reactions (Walker et al., 1996).

Thus, it is possible that YBBN_ECOLI is such a sequence and has become specialized from a general thiol-disulfide oxidoreductase into a redoxin-like protein that can only catalyze disulfide interchange reactions. However, it has not been shown that the replacement of the first (most N-terminal) cysteine yields a functional oxidoreductase. This result demonstrates the added value of using a descriptor of enzyme active sites in addition to the threading scores.

Application of a functional site descriptor to the threading alignments allows protein pairs with similar active sites to be distinguished from those that are unrelated or are simply topological cousins. Indeed, the oxidoreductase functional site descriptor of Example 1 can successfully identify the active site residues in ten sequences that are known or are proposed to exhibit the glutaredoxin/thioredoxin oxidoreductase activity in the well-studied E. coli genome. Furthermore, the method predicts thiol-disulfide oxidoreductase active sites in two other sequences that have not been identified previously.

Example 3

Functional Analysis of the E. coli Genome for Proteins Having α/β Hydrolase Activity (a) Introduction This example concerns the development and use of a functional site descriptor for the active site of α/β hydrolases. These enzymes are of significant medical interest. For example, inhibitors of acetylcholinesterase, a member of the family, are used in treatment of Alzheimer's disease, myasthenia gravis, and glaucoma. The active site descriptor described in this example is defined in terms of three dimensional α-carbon coordinates and residue identities. The goal of these efforts was to identify all proteins encoded in the E. coli genome that have an α/β hydrolase fold and exhibit a hydrolase activity. A threading algorithm was used to align 651 E. coli ORFs, and 17 of these ORFs were predicted to encode hydrolase activity through application of the α/β hydrolase active site descriptor. The putative active site residues of these proteins were also identified. One of these ORFs, YHET_ECOLI, was predicted to encode a protein classified as a member of UPF0017 (an uncharacterized protein family), which bears all the hallmarks of the α/β hydrolase family.

(b) Experimental

The α/β hydrolases are known to participate in many physiological processes, and much is known about their structure and biochemistry. The family encompasses a wide range of enzymatic functions. Table 5, below, lists some of the known members of this family.

TABLE 5

Functional diversity in the α/β hydrolase family

| Lipases: | Proteases: |
| --- | --- |
| Hepatic Lipase | Carboxypeptidase |
| Glycerol Lipase | Proline Iminopeptidase |

TABLE 5-continued

Functional diversity in the α/β hydrolase family

| Bacterial Lipase | Other Enzymes: |
| --- | --- |
| Pancreatic Lipase | Bromoperoxidase |
| Lipoprotein Lipase | Hydroxynitrile Lyase |
| Hormone-sensitive Lipase | Sterol Acyltransferase |
| Esterases: | Dienelactone Hydrolase |
| Cutinase | Haloalkane Dehalogenase |
| Thioesterase | Non-enzymes: |
| Carboxylesterase | Glutactin |
| Cholesterol Esterase | Vitellogenin |
| Acetylcholinesterase | Thyroglobulin |
| Butyrylcholinesterase | Neuroligin |

There are more than 100 crystal structures in this family deposited in the PDB database (Cousin, et al. X. (1998), *Nucleic Acids Res.* 26, 226–228). All of these proteins (most of which are enzymes) share a common fold formed by an open twisted β-sheet surrounded by α helices on both sides of the β sheet. The enzymatic members of the family all catalyze reactions that contain a hydrolysis step; therefore, they are all classified as hydrolases. The differences between the functions of the various enzymes reside in their substrate specificity and co-factor requirements In the PDB structures of these enzymes, the active site is located in the same position in each of the structures. Three residues involved in the catalysis performed by this site were identified for purposes of making the instant descriptor: His (aa position 188), Asp (aa position 175), and Ser (aa position 120). These residues are also known in the literature as comprising these enzymes' catalytic triad (Schrag and Cygler (1997), *Methods Enzymol.* 284, 85–107). Crystal structures show that these residues are closely positioned in the folded protein, but they do not form a local sequence motif because they are distant in the primary amino acid sequences.

Functionally, the side chain of the Ser residue is a nucleophilic center and the His side chain acts as a general base and be hydrogen bonded to the carboxylic group of the Asp side chain. His and Asp together form a charge-relay system. The amino acids surrounding these residues form an oxyanion hole for stabilizing the enzyme's transition state intermediate, and the Gly residues flanking the Ser position provide the structural flexibility required to perform the catalysis (Ollis, et al. (1992), *Protein Eng.* 5, 197–211). Except for His, none of the active site residues is known to be absolutely conserved throughout the family. Thus, His was selected as the primary residue for purposes of building the α/β hydrolase active site descriptor.

The structure of glycerol lipase (PDB code: 1gpl) (Withers-Martinez, et al. (1996), *Structure* 4, 1363–1374) was used to build the consensus form of the active site of the α/β hydrolases. The coordinates of the α-carbon atoms of the His, Asp, and Ser triad residues and those immediately flanking these residues, the i−1 and i+1 residues (where "i"=the "identity" His, Asp, or Ser (or substitutes thereof)) were used to build a "nine distance" descriptor which also allowed for variations in the identities of two of the three residues. Each of these distance parameters constituted a range of distances.

To search a known protein structure for this descriptor, all triplets of α-carbon atoms whose distances from each other were within 12 Å were initially identified, provided that one of the α-carbons was from a His residue. Such triplets, along with the flanking residues (i±1 positions) formed "candidate" nine carbon scaffolds that were compared to the active site descriptor by three dimensional superimposition. Amino acid triplets having RMSDs of less than 1.0 Å from the known protein structures were assigned as being among those to be included in the residue identity parameters of the α/β hydrolase active site descriptor.

To validate the putative descriptor, a search for similar nine α-carbon arrangements in 3D space was performed on a database that contains 1038 non-homologous structures extracted from the FSSP database (Holm and Sander (1997), Nucleic Acids Res. 25, 231–234). In the search, any three residues were considered (provided one was His) whose $C_{60}$—$C_\alpha$ distances were less than 12 Å from one another. By calculating the root mean square deviation (RMSD) between each candidate scaffold and the 1gpl active site scaffold through 3D superimposition, the distribution of RMSDs for all 1038 structures was obtained.

The 9-$C_\alpha$ scaffold was specific: all of the proteins that are members of the α/β hydrolase fold family have a 9-$C_\alpha$ scaffold with an RMSD of less than 1.0 Å, as compared to the 1gpl active site. Note that these proteins (listed in Table 6, below) had previously been experimentally determined to have hydrolase activity.

TABLE 6

The structurally conserved active sites of the proteins in the α/β hydrolase family.

| | Active site residues[2] | | | | | |
|---|---|---|---|---|---|---|
| PDB[1] | 1 | 2 | 3 | 4 | 5 | Function |
| 1ac5__ | $G^{75}$ | $S^{176}$ | $N^{212}$ | $D^{383}$ | $H^{448}$ | Carboxypeptidase |
| 1broA | $G^{31}$ | $S^{98}$ | $A^{123}$ | $D^{228}$ | $H^{257}$ | Bromoperoxidase |
| 1cex__ | $G^{25}$ | $S^{104}$ | $G^{132}$ | $D^{159}$ | $H^{172}$ | Cutinase |
| 1cvl__ | $G^{16}$ | $S^{87}$ | $G^{111}$ | $D^{260}$ | $H^{282}$ | Triacylglycerol hydrolase |
| 1din__ | $E^{36}$ | $C^{123}$ | $Y^{145}$ | $D^{171}$ | $H^{202}$ | Dienelactone hydrolase |
| 1ede__ | $G^{55}$ | $D^{124}$ | $N^{148}$ | $D^{260}$ | $H^{289}$ | Haloalkane dehalogenase |
| 1gpl__ | $G^{78}$ | $S^{154}$ | $D^{178}$ | $D^{207}$ | $H^{247}$ | Serine esterase |
| 1tca__ | $G^{39}$ | $S^{105}$ | $A^{132}$ | $D^{187}$ | $H^{224}$ | Triacylglycerol hydrolase |
| 1thtA | $F^{41}$ | $S^{103}$ | $V^{125}$ | $D^{200}$ | $H^{230}$ | Thioesterase |
| 1yasA | $T^{10}$ | $S^{79}$ | $N^{103}$ | $D^{206}$ | $H^{234}$ | Hydroxynitrile lyase |
| 2ace__ | $G^{114}$ | $S^{197}$ | $S^{223}$ | $E^{324}$ | $H^{437}$ | Acetylcholinesterase |
| 3tgl__ | $G^{77}$ | $S^{140}$ | $G^{171}$ | $D^{199}$ | $H^{253}$ | Triacylglycerol acylhydrolase |
| 1ivyA | $G^{56}$ | $S^{150}$ | $N^{178}$ | $D^{372}$ | $H^{429}$ | Carboxypeptidase |

[1]PDB code name with the fifth letter denoting the chain label;
[2]The structurally conserved Cα positions in the active site are listed in 5 columns: site 1 is part of the oxyanion hole; site 3 is a position sometimes involved in forming an alternative catalytic triad; sites 2, 4 and 5 are the catalytic triad position.

All other potential nine carbon scaffolds found in the 1038 structures had an RMSD greater than 1.0 Å from that of 1gpl.

This same result can be obtained by starting with the nine carbon scaffold of any one of the 13 structures listed in Table 6; therefore, the choice of the 1gpl structure itself was not critical in the design of the instant active site descriptor. From the homologies listed in Table 6, it is clear that the preferred identity residues for the active site descriptor are sites 2, 4, and 5, as listed in the table.

As the foregoing nine α-carbon geometry of the functional site descriptor is clearly well conserved through evolution, efforts were undertaken to determine if other sites near the catalytic triad existed that are also structurally well conserved among α/β hydrolases. This was done by superimposing all of the 104 known structures in the family according Co their nine α-carbon scaffolds in the active site. Structurally conserved $C_\alpha$ sites positioned within 1.5 Å in every member of the α/β hydrolase fold family were identified. In addition to the nine α-carbon atoms of the functional site descriptor for this family, two extra $C_\alpha$ positions in the vicinity of the catalytic triad were found to be structurally conserved (see Table 6, sites 1 and 3). However, the data in Table 6 show that the sequence identity of residues at these sites is not necessarily conserved.

The functional roles of the two new sites have been well characterized from the crystal structure studies (Ollis, et al. (1992), Protein Eng. 5, 197–211): site 1 (as listed in Table 6) is near to the oxyanion hole, and is believed to participate in forming hydrogen bonds with the substrate; and the site 3 residue (see the various alternatives listed in Table 6) can be hydrogen-bonded to His to form the charge-relay system in the catalytic triad.

The sites listed in Table 6 do not include all functionally important residues in the active site, as the functional roles of the residues flanking the amino acids of the various catalytic triads in this family have been reported in the literature. For instance, in the hydroxynitrile lyase (lyasA), a Cys residue at the i+1 position relative to the nucleophilic Ser position participates in the oxyanion hole formation (Wagner, et al. (1996), Structure 4, 811–822). In the case of haloalkane dehalogenase, both i+1 and i−1 positions relative to the nucleophilic center site were found to be functionally important (Franken, et al. (1991), EMBO J. 10, 1297–1302). However, sites 1–5 listed in Table 6 are structurally conserved across the entire family, albeit with some variation in several of these positions. In addition, the sites shown in Table 6 are critical to catalytic function (Ollis, et al., supra). The His at site 5 is not replaceable, but residue at site 2 can be either Ser, Asp, or Cys, and that at site 4 can be an Asp or Glu. These allowed, known variations can serve as criteria from which we can judge whether or not the active site could exhibit the hydrolase catalytic function.

A hybrid threading algorithm (Jaroszewski, et al. (1998), Protein Sci. 7, 1431–1440) was applied to the whole set of 4289 open reading frames (ORFs) in the E. coli genome (Blattner, et al. (1997), supra) to predict their structures. Briefly, the algorithm threaded each query sequence though a library of structures using dynamic programming. The structural library used was collected from the FSSP database, which contains 1038 nonredundant structures with less than 30% pairwise sequence identity among them, of which 13 were identified previously as being members of the α/β hydrolase fold family (see Table 6). Three different scoring functions were used for each comparison: the first function (sq) used sequence information only; the second function (br) used sequence similarity and burial status of the residues; and the third function (tt) used tertiary contact as well as secondary structure, burial status, and sequence information. In addition, for each query sequence from the structure library for each scoring function, the threading algorithm output the names of the five most compatible protein structures, as well as the alignments between the query sequence and the sequences of those five most compatible structures. Since three scoring functions were used for each query sequence, 15 sequence-to-structure alignments were obtained for each E. coli protein sequence. Any of the 15 structures that aligned to a given query sequence that was a member of the α/β hydrolase fold family listed in Table 6 was called a "hit". The distribution of the threading scores was calculated as the logarithm of the significance scores. See Jaroszewski, et al. (1998), Protein Sci. 7, 1431–1440). The total number of hits was 1003, corresponding to 651 different ORFs, i.e., 651 different ORFs had at least one hit to a member of the α/β hydrolase fold family.

To identify which of the proteins encoded by these 651 E. coli genome ORFs actually belong to the α/β hydrolase fold family, the following procedure was employed. First, putative active site residues of the deduced E. coli proteins were identified from the sequence-to-structure alignments produced by the threading algorithm with special attention being paid to the catalytic triad positions. Two filters were employed to make this determination for each residue that was to be assigned to the catalytic triad of an E. coli protein, namely that it have the appropriate residue identity (allowing a shift in the putative alignment by at most 3 residues) according to the functional site descriptor for this function, and that it be conserved among the close homologues of the E. coli protein.

Table 7, below, lists all those ORFs encoded in the *E. coli* genome in which a functional catalytic triad could be identified from threading alignments. According to the degree of conservation of the catalytic triad residues in a multiple sequence alignment, the ORFs were classified into three categories: (a) those having all three residues conserved; (b) those having only two residues conserved; and (c) those having only one residue or none conserved. For purposes of this example, a residue was considered conserved if more than 40% of residues at this residue's position in a multiple sequence alignment were identical to the residue found in the original sequence.

TABLE 7

Structure/function predictions for *E. coli* ORFs for members in the α/β hydrolase fold family.

| PID[1] | name[2] | pdb[3] | tp[4] | score[5] | N[6] | m[7] | triad[8] | | | ident[9] | database annotation[10] |
|---|---|---|---|---|---|---|---|---|---|---|---|
| (a) ORFs with three conserved triad residues, predicted to have hydrolase activity. | | | | | | | | | | | |
| 1786312 | speE | 1broA | tt | 3.5 | 288 | 42 | $7D^{110}$ | $5D^{238}$ | $9H^{269}$ | 0.14 | spermidine synthase†[o] |
| 1786312 | speE | 1yasA | sq | 3.4 | 288 | 42 | $5D^{88}$ | $5D^{238}$ | $9H^{269}$ | 0.20 | |
| 1786545 | | 1broA | br | 11.6 | 309 | 416 | $8S^{135}$ | $8D^{260}$ | $9H^{288}$ | 0.24 | 2-hydroxyl-6-ketonona dienedioic acid hydrolase |
| 1786545 | | 1broA | sq | 15.5 | 309 | 416 | $8S^{135}$ | $8D^{260}$ | $9H^{288}$ | 0.25 | |
| 1786545 | | 1broA | tt | 14.0 | 309 | 416 | $8S^{135}$ | $8D^{260}$ | $9H^{288}$ | 0.24 | |
| 1786545 | | 1cvl_ | br | 4.4 | 309 | 416 | $8S^{135}$ | $2E^{279}$ | $1H^{294}$ | 0.17 | |
| 1786545 | | 1cvl_ | sq | 4.3 | 309 | 416 | $8S^{135}$ | $2E^{279}$ | $1H^{294}$ | 0.17 | |
| 1786545 | | 1cvl_ | tt | 5.2 | 309 | 416 | $8S^{135}$ | $2E^{279}$ | $1H^{294}$ | 0.14 | |
| 1786545 | | 1ede_ | br | 9.3 | 309 | 416 | $8S^{135}$ | $8D^{260}$ | $9H^{288}$ | 0.22 | |
| 1786545 | | 1ede_ | sq | 12.4 | 309 | 416 | $8S^{135}$ | $8D^{260}$ | $9H^{288}$ | 0.21 | |
| 1786545 | | 1eda_ | tt | 12.2 | 309 | 416 | $8S^{135}$ | $8D^{260}$ | $9H^{288}$ | 0.21 | |
| 1786545 | | 1yasA | br | 5.1 | 309 | 416 | $8S^{135}$ | $8D^{260}$ | $9H^{288}$ | 0.21 | |
| 1786545 | | 1yasA | sq | 5.0 | 309 | 416 | $8S^{135}$ | $8D^{260}$ | $9H^{288}$ | 0.19 | |
| 1786545 | | 1yasA | tt | 7.2 | 309 | 416 | $8S^{135}$ | $8D^{260}$ | $9H^{288}$ | 0.20 | |
| 1786551 | | 1din_ | tt | 4.4 | 277 | 69 | $9S^{145}$ | $5D^{221}$ | $8H^{254}$ | 0.20 | esterase D |
| 1786551 | | 3tgl_ | sq | 5.2 | 277 | 69 | $9S^{145}$ | $8D^{199}$ | $8H^{254}$ | 0.18 | |
| 1787415 | | 1ede_ | tt | 4.4 | 521 | 62 | $5D^{187}$ | $6E^{318}$ | $4H^{359}$ | 0.19 | nitrogen fixation activator[o] |
| 1787678 | | 1thtA | tt | 4.7 | 585 | 256 | $8S^{115}$ | $9D^{230}$ | $9H^{260}$ | 0.16 | lysophospholipase |
| 1788103 | | 1gpl_ | br | 4.1 | 374 | 117 | $9C^{109}$ | $5D^{158}$ | $5H^{183}$ | 0.18 | oxygenase[o] |
| 1788477 | yeiG | 1broA | tt | 4.4 | 278 | 74 | $9S^{145}$ | $6D^{223}$ | $9H^{256}$ | 0.14 | esterase D |
| 1788477 | yeiG | 1din_ | tt | 5.8 | 278 | 74 | $9S^{145}$ | $6D^{223}$ | $9H^{256}$ | 0.16 | |
| 1788477 | yeiG | 3tgl_ | sq | 4.0 | 278 | 74 | $9S^{145}$ | $2D^{211}$ | $9H^{256}$ | 0.20 | |
| 1788598 | yfbB | 1din_ | br | 4.7 | 252 | 283 | $2S^{169}$ | $7D^{210}$ | $9H^{232}$ | 0.22 | esterase |
| 1788598 | yfbB | 1din_ | sq | 4.4 | 252 | 283 | $2S^{169}$ | $2E^{208}$ | $9H^{232}$ | 0.20 | |
| 1788598 | yfbB | 1yasA | br | 5.1 | 252 | 283 | $8S^{86}$ | $7D^{210}$ | $9H^{232}$ | 0.18 | |
| 1788598 | yfbB | 1yasA | sq | 4.4 | 252 | 283 | $2C^{97}$ | $7D^{210}$ | $9H^{232}$ | 0.15 | |
| 1788598 | yfbB | 1yasA | tt | 5.3 | 252 | 283 | $8S^{86}$ | $2E^{208}$ | $9H^{232}$ | 0.16 | |
| 1788717 | | 1ede_ | br | 3.7 | 416 | 26 | $4D^{202}$ | $6E^{343}$ | $5H^{392}$ | 0.19 | formyl coA transferase |
| 1788817 | | 1din_ | br | 5.4 | 240 | 33 | $9S^{119}$ | $9D^{167}$ | $9H^{199}$ | 0.18 | esterase |
| 1788817 | | 1din_ | sq | 4.6 | 240 | 33 | $9S^{119}$ | $9D^{167}$ | $9H^{199}$ | 0.18 | |
| 1788817 | | 1din_ | tt | 5.2 | 240 | 33 | $9S^{119}$ | $9D^{167}$ | $9H^{199}$ | 0.16 | |
| 1788884 | | 1broA | br | 6.7 | 293 | 338 | $9S^{165}$ | $9D^{236}$ | $3H^{273}$ | 0.20 | acylaminoacyl-peptidase |
| 1788884 | | 1broA | sq | 7.4 | 293 | 338 | $9S^{165}$ | $9D^{236}$ | $3H^{273}$ | 0.21 | |
| 1788884 | | 1broA | tt | 9.8 | 293 | 338 | $9S^{165}$ | $9D^{236}$ | $3H^{273}$ | 0.18 | |
| 1788884 | | 1din_ | br | 4.2 | 293 | 338 | $9S^{165}$ | $9D^{236}$ | $9H^{265}$ | 0.21 | |
| 1788884 | | 1din_ | tt | 7.3 | 293 | 338 | $9S^{165}$ | $9D^{236}$ | $9H^{265}$ | 0.21 | |
| 1788884 | | 1de_ | tt | 7.2 | 293 | 338 | $9S^{165}$ | $9D^{236}$ | $9H^{265}$ | 0.15 | |
| 1788884 | | 1yasA | br | 3.4 | 293 | 338 | $9S^{165}$ | $1E^{245}$ | $9H^{265}$ | 0.14 | |
| 1788884 | | 3tgl_ | sq | 4.5 | 293 | 338 | $9S^{165}$ | $1E^{217}$ | $9H^{265}$ | 0.15 | |
| 1789373 | | 1din_ | sq | 2.7 | 136 | 59 | $5C^{47}$ | $9D^{74}$ | $9H^{105}$ | 0.32 | dienelactone hydrolase |
| 1789373 | | 1din_ | tt | 4.4 | 136 | 59 | $5C^{27}$ | $9D^{74}$ | $9H^{105}$ | 0.29 | |
| 1789752 | yheT | 1broA | br | 4.3 | 340 | 65 | $9S^{153}$ | $8D^{280}$ | $9H^{308}$ | 0.21 | proline aminopeptidase |
| 1789752 | yheT | 1broA | sq | 4.9 | 340 | 65 | $9S^{153}$ | $8D^{280}$ | $3H^{318}$ | 0.22 | |
| 1789752 | yheT | 1broA | tt | 8.1 | 340 | 65 | $9S^{153}$ | $8D^{280}$ | $9H^{308}$ | 0.18 | |
| 1789752 | yheT | 1ede_ | tt | 6.0 | 340 | 65 | $9S^{153}$ | $8D^{280}$ | $9H^{308}$ | 0.18 | |
| 1789817 | bioH | 1broA | br | 11.3 | 256 | 414 | $8S^{82}$ | $8D^{207}$ | $9H^{235}$ | 0.23 | carboxylesterase |
| 1789817 | bioH | 1broA | sq | 9.6 | 256 | 414 | $8S^{82}$ | $8D^{207}$ | $9H^{235}$ | 0.24 | |
| 1789817 | bioH | 1broA | tt | 11.0 | 256 | 414 | $8S^{82}$ | $8D^{207}$ | $9H^{235}$ | 0.23 | |
| 1789817 | bioH | 1cvl_ | br | 6.4 | 256 | 414 | $8S^{82}$ | $8D^{207}$ | $2H^{224}$ | 0.23 | |
| 1789817 | bioH | 1cvl_ | sq | 6.0 | 256 | 414 | $8S^{82}$ | $8D^{207}$ | $2H^{224}$ | 0.21 | |
| 1789817 | bioH | 1cvl_ | tt | 5.5 | 256 | 414 | $8S^{82}$ | $8D^{207}$ | $2H^{224}$ | 0.22 | |
| 1789817 | bioH | 1ede_ | tt | 5.1 | 256 | 414 | $8S^{82}$ | $8D^{207}$ | $9H^{235}$ | 0.15 | |
| 1789817 | bioH | 1yasA | br | 5.4 | 256 | 414 | $8S^{82}$ | $2D^{219}$ | $9H^{235}$ | 0.21 | |
| 1789817 | bioH | 1yasA | sq | 4.4 | 256 | 414 | $8S^{82}$ | $8D^{207}$ | $9H^{235}$ | 0.18 | |
| 1789817 | bioH | 1yasA | tt | 6.0 | 256 | 414 | $8S^{82}$ | $8D^{207}$ | $9H^{235}$ | 0.18 | |
| 2367303 | pldB | 1broA | br | 4.1 | 340 | 262 | $8S^{139}$ | $8E^{270}$ | $9H^{305}$ | 0.18 | lysophospholipase L2† |
| 2367303 | pldB | 1broA | sq | 4.5 | 340 | 262 | $8S^{139}$ | $8E^{270}$ | $9H^{305}$ | 0.19 | |
| 2367303 | pldB | 1broA | tt | 7.4 | 340 | 262 | $8S^{139}$ | $8E^{270}$ | $9H^{305}$ | 0.17 | |
| 2367303 | pldB | 1ede_ | tt | 5.8 | 340 | 262 | $8S^{139}$ | $8E^{270}$ | $9H^{305}$ | 0.11 | |
| 2367303 | pldB | 1yasA | br | 5.5 | 340 | 262 | $8S^{139}$ | $8E^{270}$ | $9H^{305}$ | 0.22 | |
| 2367303 | pldB | 1yasA | sq | 6.5 | 340 | 262 | $8S^{139}$ | $8E^{270}$ | $9H^{305}$ | 0.20 | |

TABLE 7-continued

Structure/function predictions for E. coli ORFs for members in the α/β hydrolase fold family.

| PID[1] | name[2] | pdb[3] | tp[4] | score[5] | N[6] | m[7] | triad[8] | | | ident[9] | database annotation[10] |
|---|---|---|---|---|---|---|---|---|---|---|---|
| 2367303 | pldB | 1yasA | tt | 9.2 | 340 | 262 | 8S$^{139}$ | 8E$^{270}$ | 9H$^{305}$ | 0.18 | |
| 1790634 | yjfP | 1din__ | br | 5.6 | 249 | 284 | 8S$^{115}$ | 9D$^{197}$ | 7H$^{231}$ | 0.20 | enoate hydrolase |
| 1790634 | yjfP | 1din__ | tt | 7.6 | 249 | 284 | 8S$^{115}$ | 9D$^{197}$ | 7H$^{231}$ | 0.18 | |
| 1790634 | yjfP | 1ede__ | tt | 5.5 | 249 | 284 | 8S$^{115}$ | 9D$^{197}$ | 7H$^{231}$ | 0.16 | |
| 1790634 | yjfP | 1yasA | tt | 4.3 | 249 | 284 | 8S$^{115}$ | 9D$^{197}$ | 7H$^{231}$ | 0.12 | |
| (b) ORFs with two conserved triad residues and of uncertain function prediction. | | | | | | | | | | | |
| 1786682 | ybaC | 1broA | tt | 7.0 | 319 | 243 | 9S$^{165}$ | 3E$^{260}$ | 9H$^{292}$ | 0.14 | lipase |
| 1786682 | ybaC | 1din__ | tt | 5.6 | 319 | 243 | 9S$^{165}$ | 3E$^{260}$ | 9H$^{292}$ | 0.20 | |
| 1786902 | | 1cvl__ | br | 4.1 | 254 | 405 | 8S$^{89}$ | 1D$^{215}$ | 1H$^{237}$ | 0.21 | esterase |
| 1786902 | | 1cvl__ | sq | 4.3 | 254 | 405 | 8S$^{89}$ | 1D$^{215}$ | 1H$^{237}$ | 0.23 | |
| 1786902 | | 1cvl__ | tt | 4.6 | 254 | 405 | 8S$^{89}$ | 1D$^{215}$ | 1H$^{237}$ | 0.19 | |
| 1786902 | | 1yasA | br | 4.4 | 254 | 405 | 8S$^{89}$ | 2D$^{195}$ | 9H$^{234}$ | 0.15 | |
| 1786902 | | 1yasA | | 5.0 | 254 | 405 | 8S$^{89}$ | 2D$^{195}$ | 9H$^{234}$ | 0.17 | |
| 1786799 | fes | 1yasA | tt | 4.4 | 374 | 13 | 9S$^{255}$ | 1E$^{338}$ | 7H$^{349}$ | 0.12 | enterochelin esterase† |
| 1787796 | | 1broA | sq | 4.2 | 291 | 23 | 4S$^{126}$ | 2D$^{244}$ | 5H$^{274}$ | 0.15 | dehydrin |
| 1788037 | | 1ede__ | br | 4.2 | 295 | 26 | 2C$^{84}$ | 7E$^{228}$ | 6H$^{266}$ | 0.19 | exinuclease |
| 1788952 | tyrA | 1ede__ | br | 3.7 | 373 | 65 | 2D$^{190}$ | 7D$^{335}$ | 5H$^{148}$ | 0.20 | dehydrogenase† (pdb:1ecm)* |
| 1789094 | | 1cex__ | br | 4.0 | 212 | 37 | 4S$^{104}$ | 3E$^{152}$ | 9H$^{165}$ | 0.20 | fuculose-phosphate aldolase |
| 1789094 | | 1cex__ | sq | 3.4 | 212 | 37 | 4S$^{104}$ | 3E$^{152}$ | 9H$^{165}$ | 0.19 | |
| 1789383 | metC | 1yasA | br | 3.9 | 395 | 267 | 2S$^{155}$ | 6E$^{344}$ | 8H$^{374}$ | 0.20 | β-cystathionase† |
| 1789383 | metC | 1yasA | sq | 3.9 | 395 | 267 | 2S$^{155}$ | 6E$^{344}$ | 8H$^{374}$ | 0.20 | |
| 1790010 | yiaT | 1din__ | sq | 3.5 | 246 | 5 | 4S$^{153}$ | 6D$^{191}$ | 0H$^{208}$ | 0.19 | not found |
| 2367256 | yicI | 1gpl__ | tt | 5.8 | 772 | 64 | 5S$^{469}$ | 3E$^{488}$ | 8H$^{522}$ | 0.17 | α-glucosidase |
| (c) ORFs with one or none conserved triad residue. These ORFs were predicted either not to have hydrolase activity or not to have an α/β hydrolase fold. | | | | | | | | | | | |
| 1786231 | yabF | 1din__ | tt | 2.5 | 176 | 25 | 3S$^{69}$ | 3E$^{110}$ | 3H$^{146}$ | 0.15 | NAD(P)H oxidoreductase |
| 1786277 | ftsW | 2ace__ | br | 3.9 | 414 | 401 | 1D$^{85}$ | 2D$^{197}$ | 2H$^{295}$ | 0.20 | cell division protein† |
| 1786390 | cutF | 1din__ | sq | 3.4 | 236 | 3 | 0D$^{116}$ | 0D$^{158}$ | 0H$^{189}$ | 0.18 | copper homeostasis protein† |
| 1786416 | gmhA | 1cex__ | sq | 2.6 | 192 | 45 | 2S$^{89}$ | 2D$^{148}$ | 3H$^{164}$ | 0.15 | phosphoheptose isomerase† |
| 1786598 | sbcD | 1cvl__ | sq | 4.2 | 400 | 56 | 2D$^{119}$ | 2D$^{298}$ | 2H$^{318}$ | 0.18 | exonuclease SbcD† |
| 1786847 | ybeF | 1yasA | tt | 3.7 | 266 | 235 | 2S$^{75}$ | 2D$^{207}$ | 3H$^{244}$ | 0.20 | transcriptional regulator |
| 1787391 | | 1cex__ | tt | 2.8 | 224 | 53 | 5S$^{96}$ | 2E$^{154}$ | 3H$^{168}$ | 0.12 | repressor |
| 1787463 | hemK | 1broA | br | 3.9 | 277 | 364 | 7D$^{115}$ | 1D$^{211}$ | 2H$^{238}$ | 0.18 | protoporphyrinogen oxidase |
| 1787463 | hemK | 1broA | tt | 4.3 | 277 | 364 | 7D$^{115}$ | 1D$^{211}$ | 2H$^{238}$ | 0.17 | |
| 1787500 | oppF | 1din__ | tt | 4.5 | 334 | 415 | 3C$^{170}$ | 4D$^{224}$ | 1H$^{254}$ | 0.18 | oligopeptide transport ATP-binding† |
| 1787972 | | 1din__ | tt | 3.3 | 248 | 392 | 3D$^{119}$ | 6D$^{173}$ | 2H$^{217}$ | 0.16 | ABC transportor |
| 1788100 | | 1thtA | br | 4.1 | 314 | 265 | 1D$^{91}$ | 1D$^{206}$ | 3H$^{233}$ | 0.17 | transcription regulator |
| 1788169 | yebB | 1ede__ | br | 4.0 | 233 | 4 | 0C$^{66}$ | 0E$^{199}$ | 0H$^{218}$ | 0.17 | not found |
| 1788253 | fliK | 1tca__ | sq | 5.8 | 375 | 36 | 2D$^{121}$ | 2E$^{193}$ | 2H$^{238}$ | 0.20 | hook-length control protein† |
| 1788714 | | 1broA | br | 3.8 | 394 | 30 | 2S$^{183}$ | 7E$^{338}$ | 2H$^{373}$ | 0.21 | formyl coA transferase |
| 1788714 | | 1broA | tt | 5.3 | 394 | 30 | 1S$^{195}$ | 7E$^{336}$ | 2H$^{373}$ | 0.17 | |
| 1788716 | | 1ac5__ | br | 3.8 | 564 | 201 | 2S$^{200}$ | 4D$^{400}$ | 1H$^{498}$ | 0.18 | oxylyl-coA decarboxylase(pdb:1poxA)* |
| 1788728 | | 1broA | tt | 4.6 | 361 | 110 | 3S$^{101}$ | 6E$^{207}$ | 2H$^{240}$ | 0.16 | aminopeptidase (pdb:1chmA)* |
| 1788854 | gueA | 1ac5__ | br | 3.6 | 525 | 285 | 9D$^{239}$ | 3D$^{422}$ | 2H$^{487}$ | 017 | GMP synthase† (pdb:1gpmA)* |
| 1788978 | | 1ede__ | sq | 4.3 | 469 | 1 | 0D$^{204}$ | 0E$^{326}$ | 0H$^{355}$ | 0.14 | NADP-specific GLU dehydrogenase |
| 1789177 | | 1cvl__ | sq | 4.1 | 268 | 102 | 9D$^{61}$ | 2E$^{227}$ | 0H$^{255}$ | 0.18 | ubiquitin ligase |
| 2367172 | prfB | 1yasA | sq | 3.6 | 365 | 197 | 4D$^{79}$ | 2D$^{227}$ | 2H$^{253}$ | 0.17 | peptide chain release factor† |
| 1789409 | yqiA | 1yasA | br | 3.6 | 193 | 5 | 2S$^{69}$ | 0D$^{147}$ | 0H$^{172}$ | 0.18 | Ser/Thr-specific kinase |
| 1789760 | pabA | 1yasA | br | 4.6 | 187 | 187 | 7C$^{54}$ | 2E$^{151}$ | 1H$^{178}$ | 0.20 | para-aminobenzoate synthetase† |
| 1789775 | yhfQ | 1cex__ | sq | 3.8 | 261 | 101 | 1D$^{91}$ | 1D$^{149}$ | 2H$^{159}$ | 0.19 | fructokinase |
| 1790147 | yidZ | 1thtA | sq | 4.0 | 319 | 243 | 2S$^{165}$ | 1E$^{239}$ | 2H$^{267}$ | 0.16 | transcriptional regulator |
| 2367274 | | 1ac5__ | sq | 4.6 | 427 | 22 | 4S$^{171}$ | 2D$^{338}$ | 2H$^{398}$ | 0.17 | nonmuscle heavy chain A |
| 2367292 | as1B | 2ace__ | br | 4.4 | 411 | 91 | 7S$^{129}$ | 2E$^{226}$ | 3H$^{311}$ | 0.18 | arylsulfatase regulator† |
| 2367292 | as1B | 2ace__ | tt | 4.4 | 411 | 91 | 7S$^{129}$ | 2D$^{213}$ | 3H$^{311}$ | 0.20 | |
| 1790496 | yjcC | 1ede__ | tt | 4.1 | 528 | 64 | 3S$^{254}$ | 8D$^{423}$ | 1H$^{459}$ | 0.14 | nitrogen fixation factor |
| 1790790 | yjiK | 1yasA | sq | 4.3 | 323 | 4 | 0D$^{86}$ | 0D$^{200}$ | 0H$^{227}$ | 0.18 | extracellular nuclease |

1. "PID" is the sequence ID number in GenBank.
2. "name" is the gene name of the E. coli protein sequence.
3. "pdb" is the PDB code name of the predicted fold by which the sequence and structure were aligned (with the fifth letter denoting the chain label).
4. "tp" is the threading scoring function.
5. "score" is the threading score.
6. "N" is the number of residues of the E. coli protein sequence.
7. "m" is the number of non-redundant sequences that were found to bear sequence similarity to the E. coli protein sequence. These sequences were used to calculate the conservation profile.
8. The catalytic triad residues. Superscripts denote residue position numbers in the primary amino acid sequence of the protein; letters denote residue identity; the single digit numbers in front of the letters denote the degree of conservation obtained from a multiple alignment: "0" means 0% to 10% conserved, "1" means 10% to 20% conserved, . . . , "9" means 90% to 100% conserved.
9. "ident" is the sequence identity between the E. coli sequence and the predicted structure as denoted by the PDB code name.
10. "database annotation" means the database annotation of funcfion in SWISS-PROT (marked by the symbol †) or, if no such annotation exists, the function annotation of a similar sequence found in a PSI-BLAST search. "*" indicates those structures predicted by threading not to be α/β hydrolases, but with threading scores greater than 10. $^\delta$ indicates proteins for which existing annotations suggest a function other than hydrolase.

Table 7(a) lists 16 proteins predicted to have three dimensional structures similar to the α/β hydrolase fold family and that function as hydrolases. Among these proteins, it is experimentally known that bioH is carboxylesterase and pldB is lysophospholipase L2, both of which are within the scope of functions listed above; thus, these are confirmed predictions. The other proteins listed in Table 7(a) are proteins deduced from the E. coli ORFs. Most of them can be related to sequences that have one of the functions assigned in the search of the α/β hydrolase fold family by PSI-BLAST. However, there are a few exceptions. In particular, the database annotation column lists spermidine synthase, nitrogen fixation activator, and oxygenase, none of which seem similar to the hydrolase functions in listed in Table 6. While these predictions could be the false positives, it is also possible that these proteins were identified because they are multifunctional.

The biological function(s) of the proteins listed in Table 7(b) is(are) less certain. A PSI-BLAST search found some of these proteins to be related to lipases and esterases. However, because none of catalytic triad residues of these proteins were observed as being conserved in a multiple sequence alignment of related proteins, these proteins may function differently from the known members of the α/β hydrolase family.

The proteins listed in Table 7(c) (none which are known to be α/β hydrolases) were predicted to be unlikely to exhibit the hydrolase function because, although the catalytic triad was found in the E. coli sequence, the putative active site residues are not conserved in related proteins.

The predicative power of the instant invention is strongly illustrated by the deduced E. coli protein YHET. The SWISS-PROT database annotation for this ORF (YHET_ECOLI) indicates that this protein belongs to the uncharacterized protein family UPF0017, which contains nine previously uncharacterized proteins homologous to YHET_ECOLI from a wide range of organisms, including humans.

Table 8, below, shows the results obtained from the threading procedure for YHET.

TABLE 8

YHET_ECOLI threading scores.

| Fold | score(sq) | Fold | score(br) | Fold | score(tt) |
|---|---|---|---|---|---|
| 1xsm__ | 5.8 | 1xsm__ | 4.9 | 1broA* | 8.1 |
| 1eceA | 5.2 | 1broA* | 4.3 | 1ede__* | 6.1 |
| 1bco__ | 5.0 | 1crkA | 4.1 | 1din__* | 4.7 |
| 1an8A | 5.0 | 1oxa__ | 4.1 | 2dri__ | 4.5 |
| 1broA* | 4.9 | 1ac5__* | 3.8 | 1cnv__ | 4.1 |

The predicted folds are denoted by PDB code names with the fifth letter denoting the chain labels. "sq", "br", and "tt" refer to the types of scoring functions. Structures denoted with an asterisk are in the α/β hydrolase fold family. Threading score are expressed as the logarithm of the significance score of the threading alignments.

The threading scores predict that this protein has an α/β hydrolase fold (denoted by asterisks in Table 8), although alternative folds such as 1xsm__ cannot be excluded. Using the functional site descriptor for this protein, the most plausible model was found in the alignment between YHET and 1broA. 1broA is a bromoperoxidase (Hecht, et al. (1994), Nat. Struct. Biol. 1, 532–537), but YHET and 1broA only share about 20% sequence identity. The threading alignment using the "tt" scoring function (which used both the sequence and structure information of 1broA) predicted the C-terminal part of YHET (296 residues of the total 340) to be similar to the structure of 1broA. In this alignment, Ser153, Asp280, and His308 in YHET form the catalytic triad, which leads to the conclusion that YHET is an α/β hydrolase.

Further support for this conclusion is found in the multiple alignment of YHET homologues, most of which are members of the UPF0017 family annotated in SWISS-PROT. A multiple sequence alignment was obtained by using PSI-BLAST (Altschul, et al. (1997), Nucleic Acids Res. 25, 3389–3402) on the "nonredundant database" maintained by NCBI (National Center for Biotechnology Information), and a residue conservation profile was calculated therefrom. The default gap introduction and extension parameters were used. The mutation matrix used for alignment score calculation was BLOSUM62. The threshold E-value was chosen to be 0.05.

The procedure for calculating the conservation profile was as follows: (1) perform a PSI-BLAST search using an E. coli ORF as a query sequence; (2) delete gaps introduced into the query from the multiple sequence alignment produced by the PSI-BLAST search; (3) for each column in the multiple alignment, ignoring the gaps, count the total number of letters (L0) and the number of occurrences of the most frequently observed letter in that column (L); and (4) for each column in the multiple alignment, calculate K=10*L/L0 and round K to an integer. If L0 is less than 5, then K is set to zero. The values of K for each column in the multiple alignment constituted the conservation profile.

Using these methods, the putative catalytic residues were determined to be well conserved. The position of Gly80, predicted to be the oxyanion hole position according to the alignment, was also strictly conserved. In fact, this result does not depend on which member of the UPF0017 family was chosen as the query sequence for use with the threading algorithm and α/β hydroxylase functional site descriptor (see Table 9, below).

TABLE 9

Active site identification for each member of the UPF0017 family.

| name | pdb | tp | score | N | m | triad | | | ident |
|---|---|---|---|---|---|---|---|---|---|
| A23D_DROME | 1broA | sq | 6.3 | 398 | 52 | $9S^{192}$ | $9D^{328}$ | $9H^{359}$ | 0.19 |
| A23D_DROME | 1broA | tt | 8.8 | 398 | 52 | $9S^{192}$ | $9D^{328}$ | $9H^{359}$ | 0.19 |
| A23D_DROME | 1ede__ | tt | 8.5 | 398 | 52 | $9S^{192}$ | $9D^{328}$ | $9H^{359}$ | 0.14 |
| A23D_DROME | 1thtA | tt | 5.0 | 398 | 52 | $9S^{192}$ | $9D^{328}$ | $9H^{359}$ | 0.14 |
| A23D_DROME | 1ede__ | br | 3.7 | 398 | 52 | $9S^{192}$ | $9D^{328}$ | $9H^{359}$ | 0.18 |
| EMB8_PICGL | 1thtA | tt | 6.3 | 457 | 76 | $9S^{231}$ | $9D^{361}$ | $9H^{390}$ | 0.18 |
| HPS1_HUMAN | 1broA | tt | 8.7 | 425 | 39 | $9S^{207}$ | $9D^{345}$ | $9H^{375}$ | 0.18 |
| HPS1_HUMAN | 1broA | br | 5.1 | 425 | 39 | $9S^{207}$ | $9D^{345}$ | $9H^{376}$ | 0.18 |

TABLE 9-continued

Active site identification for each member of the UPF0017 family.

| name | pdb | tp | score | N | m | triad | | | ident |
|---|---|---|---|---|---|---|---|---|---|
| Y264_SYNY3 | 1ede_ | tt | 4.6 | 369 | 37 | $3S^{168}$ | $9D^{303}$ | $9H^{334}$ | 0.16 |
| Y264_SYNY3 | 1broA | br | 3.5 | 369 | 37 | $9S^{162}$ | $9D^{303}$ | $9H^{334}$ | 0.19 |
| YB27_YEAST | 1broA | tt | 6.2 | 451 | 42 | $9S^{247}$ | $9D^{395}$ | $9H^{423}$ | 0.20 |
| YB27_YEAST | 1broA | br | 3.6 | 451 | 42 | $9S^{247}$ | $9D^{395}$ | $9H^{423}$ | 0.23 |
| YB27_YEAST | 1yasA | tt | 4.6 | 451 | 42 | $9S^{247}$ | $9D^{395}$ | $9H^{423}$ | 0.16 |
| YHET_ECOLI | 1broA | tt | 7.8 | 340 | 73 | $9S^{153}$ | $9D^{280}$ | $9H^{308}$ | 0.18 |
| YHET_ECOLI | 1broA | br | 4 3 | 340 | 73 | $9S^{153}$ | $9D^{280}$ | $9H^{308}$ | 0.21 |
| YHET_ECOLI | 1ede_ | tt | 5.9 | 340 | 73 | $9S^{153}$ | $9D^{280}$ | $9H^{308}$ | 0.18 |
| YHET_ECOLI | 1broA | sq | 4.9 | 340 | 73 | $9S^{153}$ | $9D^{280}$ | $3H^{318}$ | 0.22 |
| YM60_YEAST | 1broA | tt | 7.3 | 449 | 53 | $9S^{232}$ | $9D^{364}$ | $9H^{392}$ | 0.18 |
| YP95_YEAST | 1yasA | tt | 4.9 | 456 | 37 | $9S^{251}$ | $9D^{399}$ | $9H^{428}$ | 0.17 |
| YYC5_CAEEL | 1broA | br | 5.8 | 375 | 66 | $9S^{189}$ | $8D^{315}$ | $9H^{344}$ | 0.18 |
| YYC5_CAEEL | 1broA | tt | 11.8 | 375 | 66 | $9S^{189}$ | $8D^{315}$ | $9H^{344}$ | 0.17 |

Column headings are the same as those in Table 7. All sequences are from the UPF0017 family annotated in the SWISS-PROT database.

A BLOCKS search (Henikoff and Henikoff (1991), *Nucleic Acid Res.* 19, 6565–6572) also supported the identification of YHET as an α/β hydroxylase through the identification of a local sequence motif (a "nucleophilic elbow; see Schrag and Cygler (1997), *Methods Enzymol.* 284, 85–107; Petersen, et al. (1997), *Methods Enzymol.* 284, 61–85) characterized by the glycines at the i+2 and i–2 positions relative to the nucleophilic Ser in YHET active site.

(c) Discussion

The biological function prediction method described in this example successfully identified the proteins belonging to the α/β hydrolase fold family encoded in the *E. coli* genome. This method has three key components: (1) an active site descriptor for the α/β hydrolase fold family; (2) a threading algorithm to predict a structure for a query sequence; and (3) a conservation profile produced by a multiple sequence alignment to the query sequence. Because this method uses structural information (namely a functional site descriptor superimposed on a structure), it is more specific than sequence motif-based methods, such as BLOCKS, PRINTS, and PROSITE. It also differs from methods that require precise coordinates of the side chain atoms for active site identification, and thus can be employed in conjunction predicted protein structures. As a result, it is particularly useful in conjunction with genome sequencing projects and efforts to determine the biological function(s) of biomolecules.

Example 4

Functional Analysis of the *Haemophilus influenzae* and *Methanococcus jannaschii* Genomes for Proteins Having Thiol/Disulfide Oxidoreductase Activity (a) Introduction This example describes the application of the inventors' sequence-to-structure-to function paradigm in a scaled up analysis of the complete genomes of *Haemophilus influenzae* and *Methanococcus jannaschii* for proteins exhibiting the thiol/disulfide oxidoreductase activity of the glutaredoxin/thioredoxin family. First, all deduced amino acid sequences in both genomes were aligned to a set of structural proteins using a threading algorithm. Structural models were then built automatically and screened using the glutaredoxin/thioredoxin functional site descriptor. Six of eight proteins in previously characterized two databases as being glutaredoxins, thioredoxins, or thiol/disulfide interchange proteins were identified. As one of the missed sequences in the *H. influenzae* genome was most likely incorrectly annotated in the database, the success ratio was six/seven. An additional 16 sequences, 11 from *H. influenzae* and five from *M. jannaschii* most of which were listed as hypothetical proteins, were predicted by our method to have the disulfide oxidoreductase active site.

(b) Methods

Development of the functional site descriptor. Because the chemistry of protein function relies on the specific tertiary placement of residues and these appear to be more highly conserved than overall sequence similarity or overall three-dimensional structure (30, 31). Geometric information (e.g., interatomic distances and bond angles) and conformational information (e.g., a residue must be in a helix) was used to develop the functional site descriptor (FSD) for the disulfide oxidoreductase activity of the glutaredoxin/thioredoxin protein family. This FSD was based on three criteria: 1) two cysteines separated by two amino acids in the primary sequence; 2) a proline must be located near the two cysteines in three-dimensional space; and 3) the two cysteines must be at the N-terminus of a helix. The allowed distance between the α-carbons of the two cysteines was 5.5+/–0.5 Å. The allowed distances between the more N-terminal and the more C-terminal cysteine and the proline were 8.5+/–1.5 Å and 6.5+/–1.5 Å, respectively. The distance criterion, 2, alone were almost sufficient to uniquely identify glutaredoxins, thioredoxins, and protein disulfide isomerases from a database of high resolution structures; addition of the helix criterion, 3, made the FSD absolutely specific (Fetrow, J. S., Godzik, A. & Skolnick, J. (1998) *J. Mol. Biol.*, submitted). Superposition of the active site cysteines and proline revealed that the structure of the site is conserved, even though the three residues are difficult to align by standard sequence alignment methods. This FSD was shown to specifically select human thioredoxin (4trx (Forman-Kay, J. D., Clore, G. M. & Gronenborn, A M. (1990) *Biochemistry* 29, 1566–1572)) and protein disulfide isomerase (1dsb (Martin, J. L., Bardwell, J. C. & Kuriyan, J. (1993) *Nature* 365:464–468)), a protein known to contain a thioredoxin domain (34, 35), from a non-redundant database of known structures (Fetrow, J. S., Godzik, A. & Skolnick, J. (1998) *J. Mol. Biol.*, submitted).

Threading and model building. All ORFs from the *Haemophilus influenzae* genome (Fleischmann, R. D. et al. (1995) *Science* 269, 496–512) and the *Methanococcus jannaschii* genome (Bult, C. J. et al. (1996) *Science* 273, 1058–1073) were assembled. Each ORF was threaded through the structures of 301 nonredundant high resolution proteins (Fischer, D., Rice, D., Bowie, J. U. & Eisenberg, D.

(1996) *FASEB J.* 10, 126–136) from the Brookhaven database (Abola, E. E., Bernstein, F. C., Bryant, S. H., Koetzle, T. F. & Weng, J. (1987) Protein Data Bank in crystallographic databases—Information content, software systems, scientific application (Data Commission of the International Union of Crystallography, Bonn/Cambridge/Chester)) using a threading algorithm. Each sequence-to-structure alignment was scored by three different scoring methods, as described in Example 1, above. Sq was a sequence-sequence type of scoring, similar to having no knowledge of structure; br was a sequence-to-structure scoring method that is based on the pseudo-energy from the probe sequence "mounted" in the structural environment of the template structure; and if was a structure-to-structure scoring method whereby the predicted secondary structure of the probe sequence is compared to the known secondary structure of the template structure. After calculation of each alignment score, the significance of each score was determined by comparing the score to an empirical score, the significance of each score was determined by comparing the score to an empirical distribution of scores following the extreme-value distribution. Alignments of each sequence to the 301 structures were then ranked according to the significance score, and the three most significant alignments for each scoring method were analyzed.

All sequences that matched either 1ego, *E. coli* glutaredoxin (Xia, T. -H. et al. (1992) *Protein Sci.* 1, 310–321), 2trx, *E. coli* thioredoxin (Katti, S. K., LeMaster, D. M. & Eklund, H. (1990) *J. Mol. Biol.* 212,167–184), or 1dsb, *E. coli* protein disulfide isomerase (Martin, J. L., Bardwell, J. C. & Kuriyan, J. (1993) *Nature* 365,464–468) as one of the top three scoring matches by any scoring method were selected for further model building. Atomic models for each sequence were built based on the template structure using automatic modeling tools available in Modeller4 (Sali, A. & Blundell, T. L. (1993) *J. Mol. Biol.* 234, 779–815). The FFF was applied directly to these all-atom models.

(c) Results

To test the disulfide oxidoreductase FSD, 1680 ORFs from the *Haemophilus influenzae* genome (Fleischmann, R. D. et al. (1995) *Science* 269, 496–512) and 1735 ORFs from the *Methanococcus jannaschii* genome were assemble. Threading was then performed and three-dimensional models were built for all of those sequences that matched one of 1ego, 2trx, or 1dsb. These predicted three-dimensional models were then screened for the thiol-disulfide oxidoreductase active site of the glutaredoxin/thioredoxin protein family using the disulfide oxidoreductase FSD.

Analysis of the *H. influenzae* genome. In the *H. influenzae* genome, seven proteins were found by performing a keyword search of the *H. influenzae* database using the keywords glutaredoxin, thioredoxin, or disulfide isomerase. (See Table 10, below).

TABLE 10

Known or putative glutaredoxins and thioredoxins in the *H. influenzae* and *M. jannaschii* genomes identified by a keyword search and proteins predicted by the FFF to have the disulfide oxidoreductase active site.

| Org/Family[1] | Keyword or Predict[2] | Seq ID[3] | Name[4] |
|---|---|---|---|
| *H. influenzae* | annotated thioredoxin glutaredoxin disulfide isomerase | HI0084 | thioredoxin m |
| | | HI1115 | trxA, thioredoxin |
| | | HI1159 | trxA, thioredoxin |
| | | HI1532 | grx, glutaredoxin |
| | | HI0428 | dsbB, disulfide oxidored |
| | | HI0846 | por, disulfide oxidored |
| | | HI1213 | dsbC, disulfide oxidored |
| | predicted | HI0303 | hypothetical |
| | | HI0404 | comF, transformation protein |
| | | HI0572 | hypothetical, conserved |
| | | HI0882 | hypothetical |
| | | HI0885 | cyt c biogen.; copper tolerance |
| | | HI0935 | helX, cyt c biogenesis |
| | | HI1068 | nrfB, formate-dep. nitrite red |
| | | HI1095 | hypothetical, conserved |
| | | HI1215 | hypothetical protein |
| | | HI1453 | pilB, transcript. regulatory repr |
| | | HI1189 | pqqIII, coenz PQQ syn. prot III |
| *M. jannaschii* | annotated thioredoxin | MJ0307 | thioredoxin |
| | predicted | NJ0156 | acetyl CoA decarbonyl/synth |
| | | NJ0757 | hypothetical |
| | | NJ1342 | hypothetical |
| | | NJ1552 | hypothetical |
| | | MJECS06 | hypothetical |

[2]Keyword is the word that was used in the keyword search of the TIGR databases. Proteins under the "annotated" subheading were known (or suggested) to belong to this family either by experiment or by sequence alignment analysis. HI1159 is probably inaccurately annotated because it has no cysteines in its sequence. If the keyword subheading is "predicted", then the listed sequences were found by application of the FSD to the model produced from the threading alignment and were not found by a keyword search of the genome database.

1. Each of these sequences was used as the search sequence for the BLAST sequence alignment algorithm, and each was shown to align with a significant score (E value, $10^{31}$) to several thioredoxins, glutaredoxins, or protein-disulfide isomerases. Four of these seven sequences were recognized by all four or three of the four local motif databases, Prosite (Bairoch, A., Bucher, P. & Hofmann, K. (1995) *Nucleic Acids Res.* 24, 189–196), Blocks (Henikoff, S. & Henikoff, J. G. (1991) *Nucleic Acids Res.*, 19, 6565–6572), and Prints (17–19). (See Table 11, below).

TABLE 11

Sequences predicted to contain the thiol-disulfide oxidoreductase activity of the glutaredoxin/thioredoxin family by BLAST sequence alignment, local sequence signatures, and by the threading/FFF protocol.

| Organism/SeqNum[1] | Blst[2] | PS[2] | P[2] | P-B[2] | B[2] | GQ[2] | Thrd/FFF[2] | Putative Active Site Res |
|---|---|---|---|---|---|---|---|---|
| *H. influenzae*-annotated | | | | | | | | |
| HI0084 | X | X | X | X | X | X | X | Cys32, Cys35, Pro76 |
| HI1115 | X | X | X | X | X | X | X | Cys69, Cys72, Pro133 |
| HI1532 | X | X | X | X | X | X | X | Cys11, Cys14, Pro60 |
| HI1213 | X | — | X1 | X2 | X | X | X | Cys116, Cys119, Pro20 |
| HI0846 | X | X | — | — | X | X | X | Cys52, Cys55, Pro171 |
| HI1159 | X | — | — | X1 | — | X | — | NA |
| HI0428 | X | — | — | — | — | X | — | NA |

TABLE 11-continued

Sequences predicted to contain the thiol-disulfide oxidoreductase activity of the glutaredoxin/thioredoxin family by BLAST sequence alignment, local sequence signatures, and by the threading/FFF protocol.

| Organism/SeqNum[1] | Blst[2] | PS[2] | P[2] | P-B[2] | B[2] | GQ[2] | Thrd/FFF[2] | Putative Active Site Res |
|---|---|---|---|---|---|---|---|---|
| *H. influenzae*-predicted | | | | | | | | |
| HI1095 | X | X | X1 | X | X | X | X | Cys78, Cys81, Pro142 |
| HI0935 | X | X | — | | | X | X | Cys75, Cys78, Pro 138 |
| HI1453 | X | — | X1 | X | X | — | X | Cys54, Cys57, Pro126 |
| HI0885 | X | X | — | X | X | X | X | Cys45, Cys48, Pro95 |
| HI1215 | X | — | — | X2 | — | — | X | Cys80, Cys83, Pro 197 |
| HI0572 | X | X | X | X | X | X | X | Cys180, Cys183, Pro22 |
| HI0303 | — | — | — | — | — | — | X | Cys139, Cys142, Pro18 |
| HI0882 | — | — | — | — | — | — | X | Cys53, Cys56, Pro152 |
| HI0434 | — | — | — | — | X | — | X | Cys51, Cys54, Pro59 |
| HI1068 | — | — | — | — | — | — | X | Cys65, Cys68, Pro 176 |
| HI1189 | — | — | — | — | — | | X | Cys45, Cys48, Pro86 |
| *M. jannaschii*-annotated | | | | | | | | |
| MJ0307 | X | — | — | X | X | X | X | Cys14, Cys17, Pro58 |
| *M. jannaschii*-predicted | | | | | | | | |
| | — | — | — | — | — | — | X | Cys273, Cys276, Pro4 |
| MJ0156 | — | — | — | — | — | — | X | Cys44, Cys47, Cys8 |
| MJ0757 | — | — | — | — | — | — | X | Cys36, Cys39, Pro69 |
| MJ1342 | — | — | — | X1* | — | — | X | Cys45, Cys48, Pro10 |
| MJ1552 | — | — | — | — | — | X | X | Cys45, Cys48, Pro40 |
| MJECS06 | | | | | | | | Cys21, Cys24, Pro68 |

[1]Organism/SeqNum is the organism and the number from the genome databases. Refer to Table 1 for the complete names of these proteins and ORFs. "Annotated" sequences are those that are identified in the TIGR databases as glutaredoxins, thioredoxins, or protein disulfide isomerases (see Table 1), while "predicted" sequences are those that are not identified in the genome databases, but are predicted to have the active site by application of the FFF to the three-dimensional model produced from the threading alignment.
[2]Seven columns refer to methods for identifying or predicting protein function: Blast, sequence alignment of the Methanococcus or Haemophilus sequence using Gapped-BLAST (11, 12) to a glutaredoxin, thioredoxin, or thiol/disulfide interchange protein with a significance score of less than $10^{-2}$; PS, either of the Prosite motifs PS00194 (thioredoxin) or PS00195 (glutaredoxin) were found in the sequence; P, the Prints motifs (PR00421A-C or PR00160A-C for thioredoxin or glutaredoxin respectively) was found in the sequence using the Prosite scoring method; P-B, the Prints motifs using the Blocks scoring method was found in the sequence; B, either of the Blocks motifs (BL00194 or BL00195 for thioredoxin or glutaredoxin, respectively) was found in the sequence; GQ, GeneQuiz (43,44) analysis of the genome; or Thrd/FFF for the FFF applied to the threading model. "X" indicates that the sequence was recognized by the searching method used; X1 and X2 indicate that three local motifs were used to identify the funciton, but only one or two, respectively, of the motifs was found in the sequence; "—" indicates that the sequence was not recognized by the method.

One of the other three sequences (HI0846) was recognized by Prosite and Blocks; one sequence (HI1159) was only recognized by the Prints database (using the Blocks scoring method); the other sequence (HI0428) was not recognized by any of the motif databases (Table 2). It is unclear whether or not these last three sequences contain the disulfide oxidoreductase activity. HI1159 is probably incorrectly annotated in the *H. influenzae* genome database because this sequence contains no cysteines, residues necessary of the oxidoreductase reaction mechanism of the glutaredoxin/thioredoxin family, even though it otherwise exhibits some sequence similarity to a thioredoxin-like protein from a cyanobacterium.

Upon analysis of the complete *H. influenzae* genome using the threading algorithm, 163 different sequences matched either 1ego, 2dsd, chain A, or 2trx, chain A. These 163 sequences produced 264 different protein models because some of the sequence were matched by more than one scoring function and the top three alignments produced by each scoring function were considered. These 264 models were screened using the thiol-disulfide oxidoreductase FSD. Five of the seven sequences identified by keyword search (See Table 11 above) were also identified by the FUNCTIONAL SITE DESCRIPTOR. Two sequences not readily recognized by local sequence signatures, HI1159 and HI0428, are also not recognized by the threading/FSD approach procedure. As mentioned above, HI1159 does not contain any cysteines in its sequence; thus, it is quite unlikely that this protein exhibits disulfide oxidoreductase activity, and this sequence is probably incorrectly identified in the *H. influenzae* database.

The FSD identified 11 additional sequences from the *H. influenzae* genome as containing the disulfide oxidoreductase active site. These sequences and the proposed active site residues are presented in Tables 1 and 2 as predictions. Comparison to the analysis of these sequences by BLAST, the motif databases (Prosite, Prints, and Blocks), and GeneQuiz (43, 44) is also presented in Table 2. Most of these 11 sequences are those that align to 1ego, 2dsb, and 2trx via the threading algorithm with the lowest significance scores.

Additional evidence of disulfide oxidoreductase activity for these 11 sequences was assessed by searching the non-redundant sequence databank by BLAST or gapped-BLAST (11,12) or the *H. influenzae* genome using TIGR search tools. Three of the sequences, HI1095 (hypothetical), HI0935 (helX, cytochrome c biogenesis), and HI1453 (pilB, transcription regulation repressor), have limited sequence identity to HI0084 or to HI1115, proteins that have been annotated as glutaredoxins thioredoxins. In addition, BLAST aligned all three of these sequences to other thio/glutaredoxins or thiol/disulfide interchange proteins in the non-redundant sequence database. Two sequences, HI0885 and HI1215, also aligned to thiol/disulfide interchange proteins via BLAST. These data provide additional evidence that the activity of these five proteins has been identified correctly. One further sequence, HI0572, aligned to glutaredoxins and thioredoxins by BLAST, although with low significance. Because this sequence was recognized by all of the motif databases, it is highly probable that this sequence also exhibits disulfide oxidoreductase activity. Two sequences, HI0303 and HI0882, only aligned with hypothetical proteins. The three other sequences, HI0434, HI1068 and HI1189, aligned with hypothetical proteins and a small number of other proteins, as follows. HI0434, listed in the database as a comF protein, aligned to several competence proteins and hypothetical proteins from other organisms. HI1068, listed as a formate-dependent nitrite reductase (nrfB), aligned with a number of other proteins identified as nrfBs. Finally, HI1189 aligned with hypothetical and coenzyme pqq synthase proteins. The common feature of these three proteins is that they are "cysteine-rich," i.e., they have a higher number of cysteines than the average protein. In particular, HI1068 has a number of CXXC signatures in its sequence. Thus, identification of these three sequences as disulfide oxidoreductases could be over-predictions because of the higher probability of aligning two cysteines and a proline in the correct positions in a "cysteine-rich" protein.

To summarize the analysis of H. influenzae genome for proteins exhibiting the thiol/disulfide oxidoreductase activity, the FSD applied to the models produced from the threading algorithm identified five of the seven proteins previously identified by others as glutaredoxins, thioredoxins, or disulfide isomerases in the genome database. One of the missed proteins contained no cysteines in its sequence, and is thus unlikely to exhibit the oxidoreductase activity. Eleven additional sequences were also predicted to have the oxidoreductase active site. Sequence data provides additional evidence that 6 of these 11 proteins exhibit that activity.

Analysis of the M. Jannaschii genome. In the M. jannaschii genome, one protein, MJ0307, was identified as a hypothetical thoredoxin by the keyword search of the TIGR database. This protein exhibits significant sequence similarity to other thioredoxins, and is recognized by the local sequence motif databases Blocks and Prints using the Blocks scoring method, but is not recognized by Prosite or by Prints using the Prosite scoring method.

Of 1735 ORFs in this genome, 204 aligned with the 1ego, 1dsb, or 2trx structures as one of the top three matches by the threading algorithm. These 204 matches produced 270 model structures. Sic of these model structures contained regions that matched with FSD, i.e., satisfied its various constraints, providing evidence that these six structures exhibit the thiol-disulfide oxidoreductase activity of the glutaredoxin/thioredoxin family. Of the six model structures, one was the true positive sequence, MJ0307.

Five other Methanococcus sequences were selected when the thiol-disulfide oxidoreductase FSD was applied to the predicted models produced from the threading alignments. MJ0757, MJ1342, and MJ1552 are hypothetical proteins. The MJ0757 sequence only has significant similarity to other hypothetical proteins. MJ1342 has no significant sequence identity to other proteins, while MJ1552 exhibits significant sequence similarity only to hypothetical proteins from other organisms and to one acyl synthase. The fact that regions of those proteins match the disulfide oxidoreductase FSD provides evidence that these proteins exhibit oxidoreductase activity.

MJ0156 is identified as an acetylCoA decarbonylase/synthase in the genome database; a gapped-BLAST (Altschul et al. (1990) J. Mol. Biol, 215:403–410) search of the non-redundant database showed that it has significant similarity to carbon monoxide dehydrogenases from other organisms, as well as several hypothetical proteins. MJECS06, a hypothetical protein found by the instant FSD, exhibited similarity to other hypothetical proteins and very distant sequence similarity to zinc finger proteins. A related protein in Methanococcus, MJECL27, exhibited conservation of several cysteines and histidines, making it likely that this protein is also a zinc finger or related metal binding protein. None of these predicted proteins, except MJ1552, was recognized by the local sequence motif databases. MJ1552 matched one of three glutaredoxin patterns (PR00160A) in the Prints database using the Blocks scoring function.

In summary, application of the oxidoreductase FSD to predicted models produced from all M. jannaschii ORFs found the single "true positive" in this genome (based on known biological activity). An additional five sequences were also identified as having the subject active site through application of the instant FSD.

Comparison to GeneQuiz, an automatic function assignment program. Both the M. jannaschii and the H. influenzae genomes have been analyzed by GeneQuiz (Casari, et al. (1996), The First Annual Pacific Symposium on Biocomputing, pp. 708–709 (World Scientific, Hawaii, USA)); Scharf, et al. (1994), The Second Int'l Conference in Intelligent Systems for Molecular Biology, pp. 348–353 (AAAI Press)). GeneQuiz uses a combination of sequence alignment, motif assignment, and literature search to assign a function to each putative protein. The assignments were ranked as "clear," "tentative," "marginal," or "no assignment," depending on the level of confidence of that data. The FSD-based approach described above differs fundamentally from the GeneQuiz approach, in that three-dimensional data are used to predict active site residues. In addition, the FSD approach described herein takes into account that a protein could have multiple active sites "function." However, for purposes of comparison, the GeneQuiz analysis for the 24 sequences identified using the FSD are also shown in Table 11, above. The need for active site descriptors is clearly demonstrated by HI1159. This sequence was identified as a thioredoxin by GeneQuiz, probably because of the sequence similarity to another thioredoxin-like protein. However, as described above, no cysteines were present in the sequence; thus, the instant FSD would not match against, or compare favorably with, this sequence as a disulfide oxidoreductase.

Likewise, GeneQuiz identified HI1165 as a possible glutaredoxin, probably because of limited sequence identity to glutaredoxin-like proteins. This sequence, which aligned to 1ego by the threading algorithm, has a single cysteine, but lacks the C—X—X—C sequence; consequently it is not identified by the disulfide oxidoreductase FSD. While it has been shown that mutants in disulfide oxidoreductase protein family that lack the second cysteine can perform disulfide isomerization with limited activity, they cannot undergo oxidoreductase activity. Thus, it is unlikely that this protein can undergo the full range of reactions found in the majority of the thiol/disulfide oxidoreductases, even though it is identified as a glutaredoxin by GeneQuiz.

GeneQuiz also identified MJ0530 as a member of this family. This protein contains two C—X—X—C sequences, but neither gapped-BLAST nor threading program algin it to any members of the glutaredoxin/thioredoxin family. BLAST only aligned it to hypothetical proteins and a possible zinc-finger protein.

These data show how FSDs can be used to identify additional biological activities in proteins already known to possess a different function. For example, HI1453 was labeled as "clearly" a repressor by GeneQuiz because of the protein's relationship to PilB proteins. However, within the alignment of these proteins, the three-dimensional arrangement of the C—X—X—C and proline residues (as described in the FSD) are conserved. So, while these proteins may be "repressors," matching the disulfide oxidoreductase constraint of the instant FSD indicates that they may also exhibit a thiol/disulfide activity.

(d) Discussion

In view of the foregoing, it is clear that FSDs, geometric and conformational descriptors of protein functional sites (here, disulfide oxidoreductase active sites), are inherently more exact than local sequence signatures and provide an unambiguous mapping of function of biological FSDs to overcome the problem of using one-dimensional sequence information to recognize three-dimensional structure. They also avoid the disadvantages of sequence alignment of distantly related proteins and the problems of adequate alignment of three-dimensional structures. While FSD generation requires that a structure of a protein known to possess the particular biological function must be known, the resultant FSD(s) for the particular function can be applied to structures of less than high resolution. Surprisingly, FSDs according to the invention can be applied to inexact models of protein structure, including those produced by current state-of-the-art tertiary structure prediction algorithms. Furthermore, the results described in this example further support the application of FSDs in the scaled-up analysis of complete genomes. In the $M.$ $jannaschii$ genome, the organism's known disulfide oxidoreductase was correctly identified and five other proteins predicted to have structures of at least a portion of which satisfied the constraints of the disulfide oxidoreductase FSD. In the $H.$ $influenzae$ genome, five likely true positive sequences were identified, a sixth possible sequence was missed, and a seventh sequence labeled as a thioredoxin was probably incorrectly characterized in the genome database. Furthermore, an additional 11 proteins in this genome were predicted to exhibit oxidoreductase activity. The data presented herein demonstrate that the approach described herein yields more, and more accurate, information than conventional sequence alignment approaches. In fact, a sequence alignment approach by itself can be misleading. For example, as described above, HI159 was identified by BLAST as aligning with thioredoxin-like proteins. However, the protein contains no cysteines; thus, the protein would not be expected to exhibit disulfide oxidoreductase activity. Such results demonstrate the need for applying functional screens to sequence alignment data. The data herein also demonstrate that application of the inventors' FSD approach yields more information than application of local motif databases such as Prosite, Prints, and Blocks.

As those in the art will appreciate, FSDs can be applied to any three-dimensional structure, whether it is an atomic resolution structure or an inexact, predicted model. Thus, libraries of FSDs will be useful for the massive structure-determination projects required in connection with genome sequencing projects, for example. In this way, in one application FSDs can be used to significantly narrow down the number of ORFs that might encode a particular active site. Moreover, this procedure can be automated.

In the application of FSDs to protein models built from ORFs found in genome sequence databases, not only can the biological activity(ies) of one or more proteins be determined, but the functional site(s) correlated with such activity(ies) can also be identified. Topological cousins, proteins with similar global folds, but different sequences and functions, can be distinguished from related proteins exhibiting similar activities.

Example 5

BASIC—A New Homology-Modeling Method (a) Summary

For 38% of the entire genome of $M.$ $genitalium,$ sequence similarity to a protein with a known structure can be recognized using the sequence alignment algorithm described in this example. When comparing genomes of $M.$ $genitalium$ and $E.$ $coli,$ over 80% of $M.$ $genitalium$ proteins have a significant sequence similarity to a protein in $E.$ $coli$ with over 40 examples that were not recognized before.

For all cases of proteins with significant profile similarities, there are strong analogies in their functions, if the functions of both proteins are known. As a result, tentative functional assignments for over 50 previously uncharacterized proteins can be made, including such intriguing cases as the putative β-lactam antibiotic resistance protein in $M.$ $genitalium.$ (b) Introduction Protein function and structure prediction by homology to already characterized proteins is known. Several programs, such as BLAST or FASTA, are geared toward recognition of protein homology by analysis of sequence similarities. Unfortunately, all such programs fail to recognize unrelated proteins having three-dimensional structures similar to an already known protein. They also fail for distantly related proteins when the sequence similarity drops to the level of random similarity between unrelated proteins. Different sets of tools have been developed in an attempt to address these two seemingly different problems. Superseding and/or enhancing the sequence/sequence similarity by sequence/structure compatibility allowed searching for unrelated proteins with similar structures. Utilizing additional information from multiple alignments of already identified homologous proteins extended the application of sequence alignment tools to recognize distantly related proteins.

The first approach i.e., threading, matches an amino acid sequence to a structure, targeting proteins with a similar three-dimensional structure with or without any homology between them. The second approach uses sequences of closely related proteins to estimate the patterns of mutations along the sequence and to create (a) position-specific mutation matrix. The objective of this approach is the same as in conventional sequence alignment methods—to identify homologies between families. In principle, threading has a much wider application than the profile, or any other sequence-only type approach. On the other hand, sequence-based methods can achieve more than structure prediction. If a protein can be placed into the already characterized family of homologous proteins, other features such as function, activity, mechanism of action, cofactors necessary in their activity and general patterns of interactions with other molecules, are often shared by homologous proteins, depending on the evolutionary distance between them. Indeed, in most known examples of apparently unrelated proteins with similar structures, the proteins in question are actually homologous.

Here, we reexamine the issue using two sequence-only tools, geared by design to recognize homologies between protein families. PSI-BLAST, the newly improved rapid database search algorithm BLAST, is a "state-of-the-art" sequence similarity tool. BASIC (Bilateral Amplified Sequence Information Comparison) is a profile-profile alignment method.

*Mycoplasma genitalium* is a small, pathogenic Gram-positive bacterium associated with pulmonary and urogenital infections in humans. Its close cousin, *Mycoplasma pneumoniae*, causes primary atypical pneumonia. *M. genitalium* is a very simple organism lacking a cell wall and is the smallest known cellular organism capable of independent replication. Its entire genome, composed of 468 predicted open reading frames, was sequenced by "shotgun" sequencing and made available on the WEB site, together with annotations identifying the function of about 67% of all proteins in this genome.

Both PSI-BLAST and BASIC were used in two different tasks. First, structural predictions for proteins from the *Mycoplasma genitalium* genome were made by comparing their sequences against sequences and sequence profiles of proteins with known structures. In this application, both programs were used merely as fold prediction tools. These structure prediction results were then used to assign *M. genitalium* proteins to homologous superfamilies. The same proteins were then compared against proteins from the *E. coli* genome to determine what functional assignments could be transferred between genomes.

(c) Results

Structural predictions. The set of 468 protein sequences from *Mycoplasma genitalium* genome was downloaded from The Institute for Genome Research WEB site. Each of these sequences was compared to a large protein sequence database using the PSI-BLAST algorithm. In the next step, the same sequences were compared to a smaller database containing sequence profiles of a set of proteins representing all currently known protein folds using a profile-profile alignment program BASIC. Technical details about the algorithms, databases and protocols for fold assignments are discussed in the Materials and Methods section at the end of this paper.

For the 468 *M. genitalium* protein sequences, the PSI-BLAST algorithm detected 118 significant (E value lower than 0.1) similarities to proteins with known structures. This constitutes 25% of the entire genome. For comparison, for the same genome, Fischer & Eisenberg reported 75 significant similarities using the older version of the BLAST algorithm and a smaller version of the database of known structures [15].

The BASIC program detected 176 significant (Z-score larger than 10) similarities to proteins with known structures (38%), an almost 50% increase over the PSI-BLAST recognition rate. This was a superset of BLAST predictions, because all the high significance BLAST predictions were independently recognized by the BASIC algorithm. Thus, there BASIC provided 58 additional structural assignments. 28 of these are for hypothetical proteins, and 16 are for proteins of *M. genitalium* whose functions are known. Several other *M. genitalium* proteins, such as Arg, Phe, Cys and Trp-tRNA synthetases, uridine kinase, and uracil phosphoribosyltransferase, have obvious functional similarities to the proteins identified by the BASIC algorithm.

Some Functional Predictions. The BASIC algorithm povides several new insights into the metabolism and other processes in *M. genitalium*. For instance:

A second enzyme involved in amino acid metabolism was identified by homology with glycine methyltransferase.

Additional enzymes involved in the synthesis of nucleic acid components were identified by homology of two hypothetical proteins and GMP synthetase.

An intriguing homology was found between two hypothetical proteins and β-lactamase. *M. genitalium* is not sensitive to penicillin or other β-lactam containing ntibiotics (it lacks a cell wall) and no penicillin binding proteins have been found in Mycoplasma [28], the problem of antibiotic resistance in multi-organism infection is not well understood. As an opportunistic pathogen, *M. genitalium* could degrade antibiotics as a part of symbiotic relation with other pathogens.

To study how many distant relations could be recognized, a database of protein profiles was prepared for all proteins from the *Escherichia coli* genome. Of the 468 proteins from the *M. genitalium* genome, 96 were found to lack homology to any known proteins. 56 proteins were similar to other proteins with unknown function and, therefore, were described as hypothetical proteins; 317 proteins had assigned function based on homology to an already characterized protein family.

In the group of proteins with no known function, 25 could be matched to other proteins from *E. coli*, 11 using PSI-BLAST and 25 using the BASIC algorithm. As before, BASIC recognition is completely inclusive of the BLAST recognition, with the BASIC algorithm identifying 14 new proteins. Of these 25 proteins, 9 were matched with hypothetical proteins, and no functional prediction was made. For the remaining 16 proteins (6 from the group identified by both algorithms and 10 from the group identified entirely by BASIC), tentative functional assignments were made based on their classification into an already characterized homologous family.

For 56 hypothetical proteins from the *M. genitalium* genome, 14 were assigned to *E. coli* proteins with known function, with 12 of them assigned by PSI-BLAST. There were also three proteins whose functions were known in *M. genitalium* that were homologous to hypothetical proteins from *E. coli*. In the latter case, all pairs are recognized both by PSI-BLAST and the BASIC algorithm.

The identification of distant evolutionary relationships is a reliable structure and function prediction tool. The position-specific iterative BLAST algorithm represents sensitive, conventional algorithm for such identification. For instance, it was shown here that this algorithm can assign folds to 25% of *M. genitalium* proteins. The BASIC (Bilateral Amplified Sequence Information Comparison) algorithm enabled 56 additional homologies between proteins from the *Mycoplasma genitalium* and well characterized protein families to be identified, bringing the total number of fold assignments to 176, or 38% of the entire *M. genitalium* genome.

Since both PSI-BLAST and BASIC algorithms do not use information about protein structure, both can be applied to search for homologues among proteins with known functions, but without known structures. To compare both algorithms in this task, the proteins from *M. genitalium* genome were compared to those from the *E. coli* genome. When compared to annotations available from the *M. genitalium* WEB site at the TIGR, 40 additional homologues were identified, with 16 of them recognized only by the BASIC algorithm. 26 proteins without known homologues were assigned to *E. coli* families and for 16 of them, function assignment could be made. In addition, for 14 hypothetical proteins with only known homologues coming from the uncharacterized ORF from other genomes, homologies to already characterized protein families were found.

(c) Materials and Methods

PSI-BLAST and the sequence database. The position specific iterative BLAST algorithm [16] is the newest version of the de facto standard of database protein similarity search algorithms. This algorithm addresses the principal shortcoming of the previous BLAST algorithm: its inability to introduce gaps in the alignment. In addition, the PSI-BLAST algorithm allows the iterative building of a sequence profile from the multiple alignment of sequences of homologous protein identified in the first pass of the algorithm. The PSI-BLAST program was downloaded from the NIH WEB site and used following the guidelines in the manual. The sequence database used by the PSI-BLAST algorithm contains a non-redundant compilation of sequences available from SWISSPROT and PIR databases, as well as translated DNA sequences from EMBL and NCBI nucleotide sequence databases and sequences of all proteins deposited in the Brookhaven PDB database. The version used in this work was compiled in November 1997.

Profile sequence preparation. Profiles were generated automatically using the multiple alignment of homologous sequences as generated by the PSI-BLAST algorithm. The same procedure was followed for the target proteins as well as for all proteins contained in the databases being searched.

Databases of sequence profiles. Two databases were constructed for the work described here. The first database of 1151 representative protein structures was prepared on the basis of a non-redundant set of protein structures included in the FSSP database as available from the DALI server at EBI. This database was used for fold prediction. The second database consists of sequence profiles for all proteins from the E. coli genome, as available on the E. coli WEB site at U. Wisconsin Genome Center.

The BASIC profile-to-profile alignment algorithm. Two sequence profiles were compared in the same way as two sequences using a local-local version of a Smith-Waterman dynamic programming algorithm [30]. All parameters were optimized for a fold recognition benchmark, as described below.

The BASIC algorithm was optimized to recognize the maximal number of structurally similar proteins on benchmarks customized for fold prediction algorithms. A particular benchmark available from the WEB server at UCLA was used during the development of a BASIC algorithm. This benchmark consists of 68 target proteins for which the correct template (structurally similar protein) has to be found in a database of ca. 300 examples. Scores of individual profile-profile comparisons were corrected for size of the proteins being compared [30, 31] and used to calculate the distributions of scores for a given prediction target. The standard deviation of the distribution is calculated and used to rescale the distribution. Re-scaled scores can be easily recalculated into the probability of the score happening by chance, which would then be equivalent to the p-value reported by BLAST.

The estimation of the reliability of the prediction was based on a Z-score statistic. A conservative cutoff of 10 standard deviations above the mean score was used in this work. The biggest Z-score for a false positive in the UCLA benchmark described above was equal to 5.2. However, bigger database sizes increase the chance of high scoring alignments of random protein pairs.

Those skilled in the art will readily appreciate that the present invention is well adapted to carry out the objects and obtain the ends and advantages mentioned, as well as those inherent therein. The functional site descriptors, and the methods for making and using the same described herein are presently representative, preferred embodiments, are exemplary, and are not intended as limitations on the scope of the invention. Changes and modifications to functional site descriptors, and methods of making and using the same, will occur to those skilled in the art upon reading this specification. It is understood that any and all of such changes and modifications are encompassed within the scope of the invention.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method of identifying a protein as having a particular biological function, the method comprising:

(a) applying a functional site descriptor that correlates with the particular biological function to a structure of a protein, wherein said functional site defines a functional site corresponding to a function of a protein or family of proteins, other than a divalent metal ion binding site, the functional site descriptor being defined using at least one atom from each of about fifteen or fewer amino acid residues used to define said functional site and comprising:

(i) an amino acid residue identity constraint for each amino acid residue used to define said functional site, wherein said amino acid residue identity constraint for each amino acid residue is a single amino acid residue identity or two or more alternative amino acid residue identities;

(ii) one or more geometric constraints for at least three different atoms, wherein at least three of said different atoms are in different amino acid residues of the protein used to define said functional site and at least one of said atoms is selected from the group consisting of a backbone amide nitrogen, an alpha-carbon, a backbone carbonyl carbon, a backbone carbonyl oxygen, and a pseudoatom comprised of two or more of a backbone amide nitrogen, an alpha-carbon, a backbone carbonyl carbon, and a backbone carbonyl oxygen; and, (iii) each geometric constraint is associated with a variance in order to provide a degree of relaxation for each said geometric constraint; and (b) identifying the protein as having the biological function if application of the functional site descriptor reveals that a portion of the structure of the protein matches the constraints of the functional site descriptor.

2. A method according to claim 1 wherein the structure of the protein is a high resolution structure.

3. A method according to claim 2 wherein the structure of the protein has been determined by x-ray crystallography or nuclear magnetic resonance.

4. A method according to claim 1 wherein the structure of the protein is a predicted structure.

5. A method according to claim 4 wherein the predicted structure is an inexact model of the structure of the protein.

6. A method according to claim 5 wherein the inexact model of the structure of the protein is produced by a computer running a computer program selected from the group consisting of an ab initio folding program, a threading program, and a homology modeling program.

7. A method according to claim 1 wherein the protein is an animal protein.

8. A method according to claim 7 wherein the animal protein is a mammalian protein.

9. A method according to claim 8 wherein the mammalian protein is a protein derived from a mammal selected from the group consisting of bovine, canine, equine, feline, ovine, and porcine animals.

10. A method according to claim 1 wherein the protein is a human protein.

11. A method according to claim 1 wherein the protein is a plant protein.

12. A method according to claim 1 wherein the protein is a prokaryotic protein.

13. A method according to claim 1 wherein the protein is a viral protein.

14. A method according to claim 1 wherein a plurality of functional site descriptors is applied to the structure of the protein.

15. A method according to claim 1 wherein the functional site descriptor is applied to a plurality of structures of the protein.

16. A method according to claim 1 wherein the functional site descriptor is applied to a structure of a plurality of proteins.

17. A method according to claim 1 wherein the functional site descriptor is applied to a plurality of structures for a plurality of proteins.

18. The method of claim 1, wherein said amino acid residues used to define said functional site are selected from the group consisting of Ala, Arg, Asn, Asp, Cys, Gln, Glu, Gly, His, Ile, Leu, Lys, Met, Phe, Pro, Ser, Thr, Trp, Tyr and Val.

19. The method of claim 1, wherein each geometric constraint within said one or more geometric constraints is selected from the group consisting of an atomic position specified by a set of three dimensional coordinates, an interatomic distance, and an interatomic angle.

20. The method of claim 19, wherein at least one member of said one or more geometric constraints is an atomic position specified by a set of three dimensional coordinates, and said three dimensional coordinates are associated with a preselected root mean square deviation variance.

21. The method of claim 19, wherein at least one member of said one or more geometric constraints is an interatomic distance.

22. The method of claim 19, wherein at least one member of said one or more geometric constraints is an interatomic angle.

23. The method of claim 1, wherein said functional site descriptor further comprises a conformational constraint.

24. The method of claim 1, wherein all of the atoms for which geometric constraints are provided are selected from the group consisting of protein backbone $\alpha$-carbons, amide nitrogens, carbonyl carbons and carbonyl oxygens.

25. The method of claim 1, wherein at least one of said one or more atoms in said amino acids used to define said functional site is a pseudoatom.

26. The method of claim 25, wherein the pseudoatom is a center of mass with respect to at least two atoms selected from at least two amino acid residues used to define said functional site.

27. The method of claim 1, wherein the functional site descriptor defines a functional site of a protein corresponding to a function selected from the group consisting of disulfide oxidoreductase activity, $\alpha/\beta$ hydrolase activity, phospholipase activity, and T1 ribonuclease activity.

28. The method of claim 1, wherein the functional site descriptor defines a function selected from the group consisting of an enzyme active site, a ligand binding domain, and a protein-protein interaction domain.

29. The method of claim 28, wherein said ligand binding domain binds a ligand selected from the group consisting of a substrate, a co-factor, and an antigen.

30. The method of claim 1, wherein the functional site descriptor defines a chemical modification site.

31. The method of claim 1 wherein said functional site descriptor is contained within a computer program product comprising a computer readable medium having executable instructions representing a computer program recorded thereon.

32. The method of claim 31 wherein said computer program product further comprises executable instructions comprising a computer program for application of a functional site descriptor to a protein structure.

33. The method of claim 32 wherein said computer program product further comprises program code for causing a computer to output the results of method to a storage device or a display device.

34. The method of claim 1, wherein said set of geometric constraints further comprises one or more geometric constraints with respect to one or more atoms or pseudoatoms of one or more amino acid residues that are adjacent to an amino acid residue used to define said functional site.

35. The method of claim 1 wherein the method is carried out using a computer system, comprising:

(a) a processor; and (b) a computer program product for application of a functional site descriptor to a protein structure.

36. The method of claim 1, wherein the functional site descriptor defines a functional site of a protein corresponding to a function selected from the group consisting of protein kinase activity, phosphorylase kinase activity, protein-tyrosine kinase activity, serine/threonine specific protein phosphatase activity, protein-tyrosine-phosphatase activity, chymotrypsin activity, trypsin activity, and thrombin activity.

37. The method of claim 1, wherein the functional site descriptor is a three atom functional site descriptor.

38. The method of claim 1, wherein the functional site descriptor is a six atom functional site descriptor.

39. The method of claim 1, wherein the functional site descriptor is a nine atom functional site descriptor.

40. The method of claim 1, wherein the functional site descriptor is a twelve atom functional site descriptor.

41. The method of claim 1 wherein at least two of said three different atoms are selected from the group consisting of a backbone amide nitrogen, an alpha-carbon, a backbone carbonyl carbon, a backbone carbonyl oxygen, and a pseudoatom comprised of two or more of a backbone amide nitrogen, an alpha-carbon, a backbone carbonyl carbon, and a backbone carbonyl oxygen.

42. The method of claim 1 wherein three of said three different atoms are selected from the group consisting of a backbone amide nitrogen, an alpha-carbon, a backbone carbonyl carbon, a backbone carbonyl oxygen, and a pseudoatom comprised of two or more of a backbone amide nitrogen, an alpha-carbon, a backbone carbonyl carbon, and a backbone carbonyl oxygen.

43. The method of claim 1, wherein the functional site descriptor is selected from the group consisting of a three atom functional site descriptor, a four atom functional site descriptor, a five atom functional site descriptor, a six atom functional site descriptor, a seven atom functional site descriptor, an eight atom functional site descriptor, a nine atom functional site descriptor, a ten atom functional site descriptor, an eleven atom functional site descriptor, a twelve atom functional site descriptor, a thirteen atom functional site descriptor, a fourteen atom functional site descriptor, and a fifteen atom functional site descriptor.

44. The method of claim 20, wherein the atomic position varies within a root mean square deviation of less than about 3 Å.

45. The method of claim 1 which further comprises applying one or more additional functional site descriptors to said protein structure.

46. The method of claim 1, which further comprises applying at least two functional site descriptors for one or more functions of a protein or family of proteins.

47. The method of claim 1, wherein said functional site is a protein active site, said amino acid residue identity constraint comprises three amino acids used to define said protein active site, and said one or more geometric constraints comprises nine distances between the α-carbons of said three amino acids and the α-carbons of the amino acids adjacent to each of said three amino acids.

* * * * *